US011136548B2

(12) United States Patent
Muffat et al.

(10) Patent No.: US 11,136,548 B2
(45) Date of Patent: Oct. 5, 2021

(54) CULTURE MEDIUM FOR GENERATING MICROGLIA FROM PLURIPOTENT STEM CELLS AND RELATED METHODS

(71) Applicant: Whitehead Institute for Biomedical Research, Cambridge, MA (US)

(72) Inventors: Julien Muffat, Cambridge, MA (US); Yun Li, Cambridge, MA (US); Rudolf Jaenisch, Cambridge, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 15/738,247

(22) PCT Filed: Jun. 24, 2016

(86) PCT No.: PCT/US2016/039336
§ 371 (c)(1),
(2) Date: Dec. 20, 2017

(87) PCT Pub. No.: WO2016/210313
PCT Pub. Date: Dec. 29, 2016

(65) Prior Publication Data
US 2018/0179494 A1 Jun. 28, 2018

Related U.S. Application Data

(60) Provisional application No. 62/350,086, filed on Jun. 14, 2016, provisional application No. 62/184,084, filed on Jun. 24, 2015.

(51) Int. Cl.
| | | |
|---|---|---|
| C12N 5/079 | (2010.01) | |
| C12N 5/00 | (2006.01) | |
| C12N 5/0793 | (2010.01) | |
| G01N 33/50 | (2006.01) | |

(52) U.S. Cl.
CPC ......... *C12N 5/0622* (2013.01); *C12N 5/0025* (2013.01); *C12N 5/0618* (2013.01); *C12N 5/0619* (2013.01); *G01N 33/5058* (2013.01); *C12N 2500/05* (2013.01); *C12N 2500/24* (2013.01); *C12N 2500/32* (2013.01); *C12N 2500/34* (2013.01); *C12N 2500/38* (2013.01); *C12N 2500/60* (2013.01); *C12N 2502/081* (2013.01); *C12N 2502/086* (2013.01); *C12N 2506/02* (2013.01); *C12N 2506/03* (2013.01); *C12N 2506/45* (2013.01)

(58) Field of Classification Search
CPC .. C12N 5/0622; C12N 5/0025; C12N 5/0619; C12N 5/0618; C12N 2506/02; C12N 2500/05; C12N 2506/45; C12N 2500/24; C12N 2502/081; C12N 2502/086; C12N 2506/03; C12N 2500/32; C12N 2500/34; C12N 2500/38; C12N 2500/60; G01N 33/5058
See application file for complete search history.

(56) References Cited

U.S. PATENT DOCUMENTS

2012/0107898 A1\* 5/2012 Neumann ............ C12N 5/0622
435/173.9
2014/0273205 A1 9/2014 Price et al.

FOREIGN PATENT DOCUMENTS

| WO | WO2008065381 | \* | 6/2008 |
| WO | WO-2014/145975 A2 | | 9/2014 |
| WO | WO-2015/056258 A2 | | 4/2015 |

OTHER PUBLICATIONS

Lee et al. Neural Stem Cells, Document # 29019, Version 5.0.0, STEMCELL Technologies, published online Apr. 2015 Retrieved from:<https://www.stemcell.com/neural-stem-cells-lp.html> Retrieved on Apr. 12, 2019.\*
Lampe et al. Biotechnol Bioeng. 130(6):1214-1223, Aug. 2009.\*
Wang et al., Nature Immunology, 13(8)753-760, Aug. 2012.\*
Kim et al., Stem Cell Rev and Rep., 10:761-771, 2014.\*
Zheng et al., Frontiers in Cellular Neuroscience, vol. 12, Article 239, Aug. 2018 (Year: 2018).\*
Gemini Bio Products, Gem21 NeuroPlexTM product information [online] Retrieved from: < https://www.gembio.com/product/gem21-neuroplextm-serum-free-supplement>. Retrieved on Nov. 20, 2019 (Year: 2019).\*
Shin et al., Stem Cells 24:125-138, 2006 (Year: 2006).\*
Chen et al., Stem Cells and Dev., 19(11):1781-92, 2010 (Year: 2010).\*
Ma, et al. Neurosci Lett. 2012; 529: 86-91 (Year: 2012).\*
Noisa et al. Stem Cells International, vol. 2015, Article ID 647437, Epub Apr. 30, 2015 (Year: 2015).\*
Andersson et al., "Lactate induces tumour necrosis factor-alpha, interleukin-6 and interleukin-1 beta release in microglial- and astroglial-enriched primary cultures," J Neurochem, 93(5):1327-1333 (2005).
International Preliminary Report on Patentability for International Application No. PCT/US2016/039336 dated Dec. 26, 2017.
International Search Report and Written Opinion for International Application No. PCT/US2016/039336 dated Oct. 9, 2016.

(Continued)

*Primary Examiner* — Christina M Borgeest
*Assistant Examiner* — Stacey N MacFarlane
(74) *Attorney, Agent, or Firm* — Foley Hoag LLP

(57) ABSTRACT

Described herein are cell culture media useful for the differentiation of human pluripotent stem cells into microglia. The methods described herein relate to in vitro generation of expandable, bankable, microglial cells by directed differentiation from human pluripotent stem cells (induced or embryonic). Using only defined cell culture media, differentiation of pluripotent stem cells is directed down a mesodermal path, in a rapid and scalable fashion, to generate cells adopting signatures of their in vivo counterparts, including gene expression, protein marker expression and functionality.

12 Claims, 46 Drawing Sheets

(56) References Cited

OTHER PUBLICATIONS

Noto et al., "Development of a culture system to induce microglia-like cells from haematopoietic cells," Neuropathol Appl Neurobiol, 40(6):697-713 (2014).
Brewer et al., "Optimized Survival of Hippocampal Neurons in B27-Supplemented Neurobasal™, a New Serum-free Medium combination," J Neurosci Res, 35: 567-576 (1993).

* cited by examiner

CULTURE MEDIUM FOR GENERATING MICROGLIA FROM PLURIPOTENT STEM CELLS AND RELATED METHODS

CROSS-REFERENCES TO RELATED APPLICATIONS

This application is the U.S. national stage of International Patent Application No. PCT/US2016/039336, filed Jun. 24, 2016, which claims the benefit of priority to U.S. Provisional Patent Application No. 62/184,084, filed Jun. 24, 2015 and U.S. Provisional Patent Application No. 62/350,086, filed Jun. 14, 2016 the contents of both of which are hereby incorporated by reference in their entireties.

BACKGROUND

Microglial cells are the resident immune cells of the central nervous system. Their role in maintenance of brain integrity is an emerging field of study. Microglia can elicit overt degeneration of neurons and glia, and are normally involved in the maintenance of the brain's homeostasis, clearing cellular debris, pruning synapses, eliminating aggregates. They are crucial in the early establishment of the nervous system. Genome-wide association studies link innate immunity with Alzheimer's disease, Parkinson's disease, amyotrophic lateral sclerosis (Lou Gherig's disease), autism and tumorigenesis. The brain is an otherwise immune-privileged tissue, where inflammation can have terminal consequences. Microglial dysfunction can render microglia the primary culprits in developmental or age-related cognitive disorders.

Differentiation of microglia-like cells from human pluripotent stem cells has proven challenging. One older protocol exists that allows for differentiation of microglia-like cells from mouse embryonic stem (ES) cells [1]; however, mouse microglia are not a good surrogate. This protocol follows a routine neural differentiation protocol, using N2 supplements, bFGF and Laminin to neuralize the ES cells. Following growth factor removal, and in an uncontrolled fashion, the authors claim to pick out small clusters of cells they call "ES cell-derived microglial precursors" (ESdMs). The protocol uses GM-CSF, a growth factor not considered to be involved in microglia development, to increase proliferation. The emergence of this population of cells occurs around day 45, in contrast to normal development of mouse microglia, which arise around embryonic day 9. This protocol dates back to 2009, and has been difficult to reproduce.

Generation of human microglial cells from stem cells could have high-impact applications for human health, particularly in disease areas such as disorders of the nervous system (e.g., stroke, cancer, and neurodegenerative diseases, such as Alzheimer's disease and Lou Gherig's disease). Given the potential applications of this technology, there exists a need to develop reliable means of generating human microglial cells from human pluripotent stem cells.

SUMMARY OF THE INVENTION

The invention provides culture media useful for differentiating pluripotent stem cells into microglial cells. Accordingly, in certain embodiments, the invention includes culture media comprising one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof, wherein the osmolarity of the medium is at least 275 mOsm.

The invention also provides methods for differentiating a pluripotent stem cell into a microglial cell. In certain embodiments, such methods comprise a) contacting a pluripotent stem cell with a passaging reagent in the presence of the culture medium of the invention, thereby forming a differentiation culture; and b) incubating the differentiation culture of step a), thereby differentiating the pluripotent stem cell into a microglial cell.

In certain embodiments, the culture medium further comprises dorsomorphin.

The invention also provides methods of culturing a neural progenitor cell from a pluripotent stem cell, comprising: a) contacting a pluripotent stem cell with a culture medium comprising dorsomorphin to form an incubation mixture; and incubating the mixture of step a) to form a neural progenitor cell.

The invention also provides cell culture kits, comprising:
a first one or more containers together comprising a base cell culture composition, comprising one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof; and
a second one or more containers together comprising a cytokine selected from IL-34 and M-CSF, or a combination thereof.

The invention also provides methods for preparing a culture medium of the invention, comprising combining one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof.

Microglia generated by the methods described herein represent an important substrate for patient-specific disease modeling, as well as a substrate to screen for modulators of neurological inflammation. Most disorders of the nervous systems (e.g., stroke, tumor, neurodegeneration) are accompanied by inflammation and altered responses by microglia. Microglial cells can under-perform, in which case they may be unable to get rid of damaging molecules, or they may also over-react, which may result in killing of nearby healthy cells (such as neurons). In some aspects, cells generated using compositions and methods described herein can be used to diagnose a patient's inflammatory potential. They can also be used to screen for drugs that can modulate their function. As immune cells, they are capable of migrating throughout the brain parenchyma, and even across the blood-brain barrier, thus representing a vehicle for therapies (e.g., genetically encoded cargos). Finally, because microglial cells are the active ingredient in cell therapies for a variety of diseases (e.g., adrenoleukodystrophy), the methods described herein represent a new source of these microglial cells, matched to the patients, combined with state-of-the-art genomic repair of mutations.

BRIEF DESCRIPTION OF THE DRAWINGS

FIG. 6A is an image of typical formation of cystic EBs bound by a single cell layer. The lower panel of FIG. 6A is an image of concurrent induction of default pathway neuralized EBs (prominent radial architecture of the compact neuroepithelium). Scale bars: 200 µm. FIG. 6B is an image of typical appearance of endothelial lawns emerging from plated cystic EBs (on PDL coated plastic). Phase panels display the island formations with raised edges (left), and the progressive merger of such edges into raised ropes. Raised structures are positive for VE-Cadherin (green pseudocolor), and c-kit (magenta pseudocolor). Scale Bars: 80 µm. FIG. 6C is an image of higher magnification of raised structures surrounding islands, staining for CD41 (green pseudocolor), and CD235a (magenta pseudocolor). Scale bar: 25 µm. FIG. 6D shows an image demonstrating after 2 weeks in suspension culture, cystic EBs can be plated to PDL coated plastic (left, phase contrast. Scale bar: 200 µm), and large domains stain positive for the nucleus-localized transcription factor PU.1 (right, green pseudocolor). FIG. 6E is an image of delamination of grape-like structures towards the luminal side from YS-EBs (red arrows, top left and right, scale bars: 40 µm and 25 µm, respectively). Putative myeloid cells are seen delaminating outward into the suspension medium (red arrow, bottom left, scale bar: 25 µm). Homogeneous population of round motile cells seen delaminating and spreading away from the source YS-EB (Bottom right, scale bar: 80 µm).

FIG. 7A is a differentiation protocol schematic showing the suspension culture (top row), and the selective adherent conditions (bottom row). FIG. 7B is an image of low magnification view of delaminated lawn after plating. 1st panel: nuclear DAPI (grey scale). 2nd panel: nuclear PU.1 (magenta). 3rd panel: membrane CD11b/Itgam (green pseudocolor). 4th panel: merged PU.1 and CD11b channels. Scale bar: 25 µm. FIG. 7C is a high magnification view of ramified cell in resting culture. 1st panel: phase contrast (grey scale). 2nd panel: nuclear PU.1 (magenta). 3rd panel: cytoplasmic IBA1/AIF1 staining. 4th panel: merged view of PU.1 and IBA1. Scale bar: 5 µm. FIGS. 7D and 7E is an image of FACS scatter plots showing the high homogeneity of harvested PMGLs for IBA1, CD11b and CD45.

FIG. 7F left panel is an image of phagocytosis (fluorescent bead uptake), negative trail left by a single cell on bead lawn and extreme intracellular accumulation (scale bar: 10 µm). Right panel, cotton fiber opsonized by pMGLs (scale bar: 25 µm). FIG. 7G shows progressive rapid uptake of beads by pMGL cells (red arrows). Beads initially make contact with membrane ruffles, and settle in the cytoplasm. Scale bar: 3 µm.

FIG. 8A is an image of phase contrast panels displaying first-order ramified morphologies of pMGLs (either hES or iPS-derived), and absence of fried-egg" macrophage-like cells. Scale bars: 25 µm. FIG. 8B shows high magnification phase pictures highlighting first order branching, and membrane ruffles terminating branches. Mouse primary neonatal microglia (mNMG), human primary fetal microglia (hFMG), human stem cell derived pMGLs. scale bars: 10 µm. FIG. 8C shows that as they mature, pMGLs lose their proliferative potential, as measure by EDU incorporation in DAPI positive nuclei (ratios averaged for 2 biological replicates, at 2 weeks and 2 months, error bars are SEM, TTEST, P<0.05). FIG. 8D shows ramified pMGLs are positive for TMEM119 (green pseudocolor, vesicular and diffuse staining, top row), and FIG. 8E shows P2RY12 (green pseudocolor, vesicular and diffuse staining, bottom row). Nuclei are stained with DAPi (magenta pseudocolor). Scale bars: 10 µm. FIG. 8F shows confocal optical slice of wider field-of-view, showing homogeneous expression of IBA1 (green), TMEM119 (magenta) and CD45 (white).

FIG. 9A shows a baseline cytokine profiler assay from $10^5$ pMGLs conditioning 2 mL of NGD in 24 hours. Top panel: 10' exposure, showing baseline secretion of detectable CCL2, MIP1a/b, CXCL1 and IL8. Lower Panel: profile after stimulation for 24 hours with 100 ng/mL LPS and 20 ng/mL IFNγ. IL6, TNFα, MIP1a/b and CXCL10 display a dramatic increase (highlighted in FIG. 9B). These upregulations can mediate further leukocyte and lymphocyte recruitment and activation in vivo. FIGS. 9C and 9D show qPCR for TNFα and IL6, showing transcriptional upregulation upon stimulation (respectively 3-fold and 30-fold, error bars are SEM from biological replicates, TTEST significance is reported). FIG. 9E shows an example of phenotypic output in isogenic MECP2 mutant and wild-type cells. Average cell spread (surface) and perimeter are significantly lower in MECP2 mutant microglia (TTEST, p<0.05, 2 biological replicates×3 technical replicates).

FIG. 10A shows bar graphs represent normalized expression (arbitrary units from RNAseq data) between pMGLs (black bar), primary human fetal microglia (red bars, hFMG), and differentiated human neural progenitors (red bars, Diff. NPCs). pMGLs express these genes at similar or higher levels than primary fetal cells, while differentiated NPCs (mixtures of neurons, astrocytes, oligodendrocytes) express little of each. Several genes expressed at higher levels in pMGLs are upregulated during postnatal development in the mouse (CST3, P2RY13, TMEM119, OLFML3, SELPLG, TXNIP). Error bars represent SEM calculated on raw reads for each gene, for biological replicates (ES/iPS line). FIG. 10B shows unbiased hierarchical clustering using genes in table 3 comparing pMGLs to FMGs and primary human brain cells. Adult and Fetal microglia cluster with pMGLs (Red, Microglia cluster), while NPCs cluster with neuroectodermal brain cells (Blue, Neural cluster).

FIG. 11A (top) is a schematic representation of transwell culture system exposing pMGLs to conditioned medium from differentiating neuro-glial cultures. Bottom: schematic representation of direct re-aggregation after GFP transduction, as free-floating spheroids or 3D stacks in transwells. FIG. 11B shows principal component analysis of RNAseq profiles. Differentiated neural cultures (N1 and N2, mix of neurons and NPC-derived glia, grey/black circles) cluster away from pMGLs and primary microglia (along PC1 axis). Primary microglia (FMG1/2/3, brown hues) samples line up tightly with pMGLs (pMGL1/2/3, blue/red/green circles) along PC1, away from neural cultures. pMGLs exposed to conditioned medium (NCM) from neural cultures (pMGL1/2/3+NCM; blue, red, green triangles) move along the PC2 axis, towards the primary fetal microglia signature. FIG. 11C shows relative position of labeled pMGLs in 3d culture on transwell, showing non-overlapping GFP domains (tiling, scale bar: 200 μm). FIG. 11D is a representative image of GFP positive pMGLs (grey scale) after 4 weeks in 3D neural stacks (live observation). Second order branching pattern is highly reminiscent of that of in vivo microglia. Scale bars: 10 μm. FIG. 11E is an image of an optical section through fixed 3D neuroglial culture (without embedded pMGLs), highlighting tissue-like density, mature dendritic arborization (neuronal MAP2, green) and presence of mature astrocytes (GFAP positivity, magenta). Scale bar: 50 μm. FIG. 11F shows maximum projection (scale bar: 2 μm) pointing to rapidly extending (yellow arrows) and retracting (red arrow) protrusions in the 3D neuroglial cultures. FIG. 11G shows branch movements over 300 s. FIG. 11H shows a response to localized cellular damage in 3D culture, montage of time-lapse images. Yellow arrowhead points to two-photon laser ablation after 5 minutes of acquisition. At t=20', maximum extension (>100 um) of a single process from nearby microglia towards the site of injury, followed by migration of the cell bodies behind the process, ultimately gathered around the wound after 2 hours of observation. Red arrowhead point to microglia-like cells further away from injury, not reacting to the damage.

FIG. 12A is an image of cells seeded on primaria plates (modified polystyrene) to provide attachment for human fetal microglia (hFMG, left panel) and mouse neonatal microglia (mNMG, right panel). Scale bar: 25 μm. FIG. 12B is an image of hMFGs grown in serum-free medium with CSF1 (long/mL) and IL-34 (100 ng/mL) survive for months (left panel) whereas cells detach and die within a few days in complete medium without growth factors (right panel). Scale bar: 25 μm. FIG. 12C shows plating of early EBs (<2 weeks) yields two distinct populations: endothelial lawns from cystic EBs (left panel), and rosette forming neuro-ectoderm from dense neuralized EBs (right panel). Scale bar: left=80 μm, right=200 μm.

FIG. 13A shows high expressions of CD11b, CD45, and IBA1 are expected in many tissue-resident macrophages and, in the brain, exclusively restricted to microglia. FIG. 13B shows an emphasis on 4 disease-related genes absent from neuroectodermal derivatives, whose study require microglia-like cells. APOE, CD33 and TREM2 harbor allelic variants linked with increased risk of sporadic Alzheimer's disease. HEXB is very highly expressed in pMGLs and primary microglia. Error bars represent SEMs using normalized raw reads for the different biological replicates. FIG. 13C shows an example of two genes, GPR56 and BIN1 which are NOT microglia specific in the brain. Rather they are brain-enriched, are high in microglia and virtually absent from peripheral macrophages.

DETAILED DESCRIPTION OF THE INVENTION

I. Formulation of Culture Media

Figure 1A:
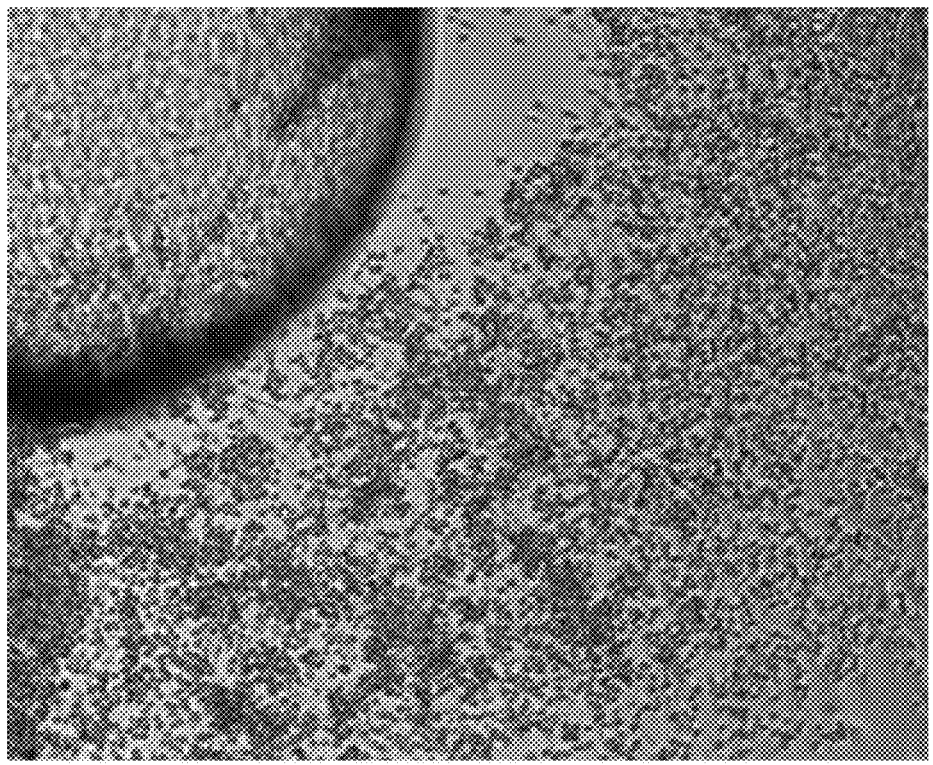
FIG. 1A is an image showing one spherical yolk-sac organoid (YSO) (top left), surrounded by delaminating microglia-like cells.

The present invention is based on the surprising discovery of a culture media useful for differentiating human pluripotent stem cells (e.g., human induced pluripotent stem cells or embryonic stem cells) into human microglial cells.

The present invention relates to methods and compositions for differentiation of pluripotent stem cells, such as embryonic stem cells and iPS cells, or variants thereof, into microglial cells. Accordingly, in certain embodiments, the invention provides a culture medium, comprising: one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof; wherein the osmolarity of the medium is at least 275 mOsm. In certain embodiments, the culture medium of the invention comprises galactose. In certain preferred embodiments, the culture medium of the invention comprises glucose.

The cell culture media of the present invention are aqueous-based (i.e., the media comprise a number of ingredients in a solution of deionized, distilled water). In certain embodiments, the media can be reconstituted from dry powder and/or frozen components.

The term "ingredient" refers to any compound, whether of chemical or biological origin, that can be used in cell culture media to maintain or promote the growth or proliferation of cells. The terms "component," "nutrient" and ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need.

By "cell culture" or "culture" is meant the maintenance of cells in an artificial, in vitro environment. It is to be understood, however, that the term "cell culture" is a generic term and may be used to encompass the cultivation not only of individual cells, but also of tissues, organs, organ systems or whole organisms, for which the terms "tissue culture," "organ culture," "organ system culture" or "organotypic culture" may occasionally be used interchangeably with the term "cell culture."

Protein synthesis precursors include amino acid ingredients. In certain embodiments, the amino acid ingredients which may be included in the media of the present invention include L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine and L-valine. These amino acids may be obtained commercially, for example from Sigma (Saint Louis, Mo.).

Alternatively, in some other embodiments, only essential amino acids are included in the media of the present invention. Certain cells, such as human cells, must have adequate amounts of 9 amino acids to survive. These so called "essential" amino acids cannot be synthesized from other precursors by these cells. However, cysteine can partially meet the need for methionine (they both contain sulfur), and tyrosine can partially substitute for phenylalanine. Such essential amino acids include: Histidine, Isoleucine, Leucine, Lysine, Methionine (and/or cysteine), Phenylalanine (and/or tyrosine), Threonine, Tryptophan, and Valine. In certain embodiments, only Histidine, Isoleucine, Leucine, Lysine, Threonine, Tryptophan, and Valine are included.

In certain embodiments of the culture medium, the one or more amino acids present in the culture medium include one or more amino acids selected from glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, and L-valine.

In certain embodiments, the culture medium of the invention comprises glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, and L-valine.

While not wishing to be bound by any particular theory, antioxidants generally help to quench free-radicals, which are thought to be detrimental to cell growth in general. In certain embodiments, the culture medium of the invention comprises one or more antioxidants, which can include beta-carotene, vitamin E, vitamin C (ascorbic acid), vitamin K3, glutathione (reduced), niacin (or niacinamide), or DTT (dithiothreitol). The antioxidants may optionally be supplemented with trace metals, including Zn, Se, Cr, Cu, Mg, or Mn.

Again, without wishing to be bound by theory, trace minerals may be necessary for the constitution of certain enzymes. For example, glutathione peroxidase uses selenium and glutathione superoxide uses copper as a cofactor. It was postulated that in diseases where there is a large free radical load, there may be deficiencies of these trace elements in particular microenvironments. The presence of trace minerals may be helpful to enzymatic antioxidants (which may have been devoid of the cofactors). Thus the presence of the trace minerals may allow effective use of the enzymatic antioxidants by the host. Since it is known that zinc can up-regulate superoxide dismutase and selenium can up-regulate glutathione peroxidase, increasing trace minerals in a given microenvironment would produce a net increase in enzymatic antioxidants in the microenvironment. A net increase in the enzymatic antioxidants and increasing amphipathic antioxidant would further reduce oxidative damage to tissue or cells, as well as other deleterious effects due to free radicals.

Thus, inorganic salt ingredients, such as cations, ions, and trace metals, that may be included in the media of the present invention include, but are not limited to calcium salts (e.g., $CaCl_2$), copper salts (e.g., $CuSO_4$), iron salts (e.g., $FeSO_4$, $Fe(NO_3)_3$), potassium salts (e.g., KCl), magnesium salts (e.g., $MgCl_2$), sodium salts (e.g., sodium acetate, NaCl, $NaHCO_3$, $Na_2HPO_4$, $Na_2SO_4$), zinc salt (e.g., $ZnSO_4$). Optionally, additional inorganic salt ingredients may include a manganese salt (e.g., $MnCl_2$), silicon, molybdenum, vanadium, nickel, tin, and other trace elements.

These trace elements may be provided in a variety of forms, preferably in the form of salts such as $Na_2SeO_3$, and ZnSO (or $Na_2SiO_3$, $(NH_4)_6Mo_7O_{24}$, $NH_4VO_3$, $NiSO_4$, SnCl for optional salts). These inorganic salts and trace elements may be obtained commercially, for example from Sigma (Saint Louis, Mo.).

In certain embodiments, the one or more inorganic salts present in the culture media of the invention include one or more inorganic salts selected from calcium chloride, ferric nitrate, magnesium chloride, potassium chloride, sodium bicarbonate, sodium chloride, sodium phosphate (monobasic), and zinc sulfate.

In certain embodiments, the culture medium of the invention comprises calcium chloride, ferric nitrate, magnesium chloride, potassium chloride, sodium bicarbonate, sodium chloride, sodium phosphate (monobasic), and zinc sulfate.

In certain embodiments, the one or more vitamins present in the culture media include one or more vitamins selected from choline chloride, D-calcium pantothenate, folic acid, niacinamide, pyridoxal hydrochloride, riboflavin, thiamine hydrochloride, Vitamin B12, and i-inositol.

In certain embodiments, the culture medium of the invention comprises choline chloride, D-calcium pantothenate, folic acid, niacinamide, pyridoxal hydrochloride, riboflavin, thiamine hydrochloride, Vitamin B12, and i-inositol.

In certain embodiments, the culture medium of the invention comprises galactose. In certain preferred embodiments, the culture medium of the invention comprises glucose. In some embodiments, the culture medium of the invention comprises galactose and glucose.

In certain embodiments, the culture medium of the invention comprises glycine, L-alanine, L-arginine hydrochloride, L-asparagine-H2O, L-cysteine, L-histidine hydrochloride-H2O, L-isoleucine, L-leucine, L-lysine hydrochloride, L-methionine, L-phenylalanine, L-proline, L-serine, L-threonine, L-tryptophan, L-tyrosine, L-valine, choline chloride, D-calcium pantothenate, folic acid, niacinamide, pyridoxal hydrochloride, riboflavin, thiamine hydrochloride, vitamin B12, i-inositol, calcium chloride, ferric nitrate, magnesium chloride, potassium chloride, sodium bicarbonate, sodium chloride, sodium phosphate monobasic, zinc sulfate, D-glucose, HEPES, phenol red, and sodium pyruvate. In some embodiments, glucose is not added to (e.g., omitted from) the medium. In some embodiments, the medium is called Neurobasal™ Media.

Although not considered essential, the subject medium may additionally comprise one or more buffering agents, such that a balanced pH is maintained in long-term culture. Frequent, constant or continuous change of culture medium may also help to restore medium pH in fast growing cells. In certain embodiments, the buffering agent of the culture medium is a bicarbonate salt or 2-[4-(2-hydroxyethyl)piperazin-1-yl]ethanesulfonic acid (HEPES). Preferably, the buffering agent is HEPES.

Some or all of the above ingredients, when admixed together in solution, can form a "basal medium." To this basal medium, other components, such as serum albumin, transferrin, glutamine, biotin, ascorbic acid, and/or lactic acid, are added to formulate the complete culture media of the present invention. These latter added components may be added to freshly formulated basal medium, or they may be admixed as in a stock solution stored frozen until being added to basal medium to formulate the complete medium of the present invention. The admixture may also be prepared as a 1-1000×formulation, most preferably as a 1×, 100×, 500× or 1000×formulation, which is then diluted appropriately into culture medium to provide a 1×final formulation in the complete media of the present invention.

In certain embodiments, the serum albumin in the medium of the invention is bovine serum albumin, such as bovine serum albumin fraction V or lipidated bovine serum albumin, or human serum albumin. In certain exemplary embodiments, the serum albumin is Albumax® I or AlbuMAX® II Lipid-Rich BSA.

In certain embodiments, the pyruvate salt in the medium of the invention is sodium pyruvate. Sodium pyruvate can act in the medium as a carbohydrate synthesis and energy metabolism precursor.

In certain embodiments, the concentration of glucose or galactose in the culture medium is from about 5 mM to about 30 mM, from about 5 mM to about 25 mM, from about 5 mM to about 20 mM, from about 5 mM to about 15 mM, from about 5 mM to about 10 nM, about 25 mM, or about 5 mM. Preferably, the culture medium comprises glucose at a concentration of from about 5 mM to about 25 mM. Glucose can similarly function in the medium as a carbohydrate synthesis and energy metabolism precursor.

For any embodiment of the invention in which a value is prefaced by the term "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately". As used herein, "about" includes values that are up to 10% higher or 10% lower than the recited value. In certain embodiments, "about" indicates ±10%, ±9%, ±8%, ±7%, ±6%, ±5%, ±4%, ±3%, ±2%, or ±1%, of the recited value.

In certain embodiments, the culture medium further comprising progesterone, putrescine dihydrochloride, insulin, and sodium selenite.

Many tissue culture media typically contain one or more antibiotics, which are not necessary for cell growth/proliferation per se, but are present to inhibit the growth of other undesirable microbes, such as bacteria and/or fungi.

Antibiotics include natural and synthetic chemical substances of relatively low molecular weight produced by various species of microorganisms, such as bacteria (including *Bacillus* species), actinomycetes (including *Streptomyces*) and fungi, that inhibit growth of or destroy other microorganisms. Substances similar in structure and mode of action to natural antibiotics may be synthesized chemically, or natural compounds may be modified to produce semi-synthetic antibiotics. The major classes of antibiotics are: (1) the β-lactams, including the penicillins, cephalosporins and monobactams; (2) the aminoglycosides, e.g., gentamicin, tobramycin, netilmycin, and amikacin; (3) the tetracyclines; (4) the sulfonamides and trimethoprim; (5) the fluoroquinolones, e.g., ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides.

Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

Thus for convenience and other practical reasons, the culture media of the invention may be additionally supplemented by one or more antibiotics or other substances that inhibit the growth/proliferation of undesirable bacteria, fungi, and/or viruses. In other embodiments, however, the subject medium may be free of any antibiotics. Without wishing to be bound by any theory, omission of antibiotics may help to ensure optimum differentiation of pluripotent stem cells. Extra care should be taken when handling cells growing in antibiotic-free medium in order to avoid possible contamination.

Accordingly, in certain embodiments, the culture medium comprises one or more antibiotics. In certain embodiments, the one or more antibiotics include a penicillin antibiotic. In certain embodiments, the one or more antibiotics include an aminoglycoside antibiotic. In certain embodiments, the one or more antibiotics include benzylpenicillin. In certain embodiments, the one or more antibiotics include streptomycin.

In certain embodiments, the culture medium further comprises benzylpenicillin and streptomycin.

In certain embodiments, the glutamine is provided as L-alanyl-L-glutamine (sold as GlutaMAX™-I by Life Technologies).

In certain embodiments, the glutamine is provided as glycyl-L-glutamine.

In certain embodiments, the medium does not contain free L-glutamine.

In certain embodiments, the lactic acid is supplied as sodium lactate.

In certain embodiments, the medium further comprises L-carnitine, cholesterol, corticosterone, ethanolamine, D(+)-galactose, glutathione (reduced), lecithin, linoleic acid, linolenic acid, phosphatidylcholine, triiodo-I-thyronine, DL-α-Tocopherol and/or DL-α-Tocopherol acetate, catalase, and superoxide dismutase.

In certain embodiments, the medium further comprises biotin, L-carnitine, cholesterol, corticosterone, ethanolamine, D(+)-galactose, glutathione (reduced), lecithin, linoleic acid, linolenic acid, phosphatidylcholine, progesterone, putrescine, sodium selenite, triiodo-I-thyronine, DL-α-Tocopherol and/or DL-α-Tocopherol acetate, albumin, catalase, insulin, superoxide dismutase, and transferrin. The medium can optionally further comprise retinol and/or retinyl acetate.

In connection with any of the above-described embodiments, in certain embodiments, the medium comprises a serum-free medium supplement called Gem21.

In certain such embodiments, Gem21 comprises corticosterone, linoleic acid, linolenic acid, progesterone, DL-α-Tocopherol and/or DL-α-Tocopherol acetate, lipoic acid, L-carnitine HCl, ethanolamine HCl, D-Galactose (anhydrous), putrescine dihydrochloride, sodium selenite, bovine serum albumin (BSA) (low-endotoxin), catalase, glutathione (reduced), insulin, human-holo-transferrin, superoxide dismutase, T$_3$, water, and optionally ethanol. The pH of the medium may be adjusted, e.g., by adding NaOH and/or HCl, adding a buffer, or both. In some embodiments, vitamin A is added the medium. In other embodiments, vitamin A is not added to the medium. In some embodiments, the buffer has a low endotoxin content (e.g., less than 0.5 EU/mg, preferably even less than 0.1 EU/mg).

The BSA used to prepare a medium as described herein may be a BSA preparation with a low endotoxin content (e.g., less than 0.5 EU/mg), although any suitable preparation of BSA may be used, provided that the overall endotoxin content of the medium is suitable for its intended use.

In other certain such embodiments, Gem21 consists essentially of corticosterone, linoleic acid, linolenic acid, progesterone, DL-α-Tocopherol and/or DL-α-Tocopherol acetate, lipoic acid, L-carnitine HCl, ethanolamine HCl, D-Galactose (anhydrous), putrescine dihydrochloride, sodium selenite, bovine serum albumin (BSA) (low-endotoxin), catalase, glutathione (reduced), insulin, human-holo-transferrin, superoxide dismutase, T$_3$, and water. Ethanol may optionally be present, as may pH-adjusting agents (e.g., buffer, NaOH and/or HCl). In some embodiments, vitamin A is added in the medium. In other embodiments, vitamin A is not added to the medium.

In other certain such embodiments, Gem21 consists of corticosterone, linoleic acid, linolenic acid, progesterone, DL-α-Tocopherol and/or DL-α-Tocopherol acetate, lipoic acid, L-carnitine HCl, ethanolamine HCl, D-Galactose (anhydrous), putrescine dihydrochloride, sodium selenite, bovine serum albumin (BSA) (low-endotoxin), catalase, glutathione (reduced), insulin, human-holo-transferrin, superoxide dismutase, T$_3$, water, one or more pH-adjusting agents (e.g., buffer, NaOH, HCl, etc.) and optionally ethanol. In some embodiments, vitamin A is present in the medium. In other embodiments, vitamin A is not present in the medium.

To the extent that one or more components do not substantially affect (e.g., adversely affect) the performance of the medium in terms of supporting microglial differentiation, the subject medium may in certain embodiments include and tolerate the presence of one or more of such components. In certain embodiments, any one or more such components may be expressly excluded from the media of the invention.

In certain embodiments, the osmolarity of the culture medium meets at least the minimum osmolarity requirements needed for human cells on a rapid feeding schedule. Accordingly, in certain embodiments, the osmolarity of the medium is at least 275 mOsm, at least 280 mOsm, at least 285 mOsm, at least 290 mOsm, or at least 295 mOsm. In some embodiments, the osmolarity of the medium is between 275 mOsm, 280 mOsm, 285 mOsm, or 290 mOsm, and 295 mOsm. In some embodiments the osmolarity of the medium is between 275 mOsm, 280 mOsm, 285 mOsm, 290 mOsm, or 295 mOsm and 300 mOsm. In some embodiments the osmolarity of the medium is between 275 mOsm, 280 mOsm, 285 mOsm, 290 mOsm, or 295 mOsm and 305 mOsm. In some embodiments the osmolarity of the medium is between 290 mOsm and 300 mOsm. In certain preferred embodiments, the osmolarity is tuned by supplementation of the medium with sodium chloride.

In some embodiments, the culture medium comprises the serum-free formulation disclosed in Table 1. The formulation in Table 1 reflects component concentrations that approximate those of human cerebrospinal fluid, providing all metabolic substrates necessary for individual cell types to grow in this medium. Ionic concentrations in Table 1 approximate human cerebrospinal fluid osmolality, thus providing extracellular sodium concentrations necessary for proper electrophysiological function. In certain embodiments, iron is not present in simple salt form in the serum-free formulation, but is instead provided as iron-loaded transferrin (in Neurobasal), in order to avoid redox cycling through Fenton chemistry. In certain embodiments, glutamate is omitted to avoid the excitotoxicity of this amino acid in dissociated cultures. Without wishing to be bound by theory, pyruvate and lactic acid serve as energy-providing and neuroprotective substrates in addition to the more canonical oxidative substrates (glucose, galactose and glutamine/glutamax). Biotin and lipid-loaded albumin (Albumax I) support de novo synthesis of lipid bilayers (e.g., axons, myelin sheaths). In some embodiments, the culture medium comprises this base medium, referred herein as NGD (Neuro-Glial Differentiation) medium. In some embodiments, phenol red is present in the NGD medium at a concentration of less than 0.001 mg/ml, less than 0.01 mg/ml, less than 0.1 mg/ml, less than 1 mg/ml, less than 5.0 mg/ml, or less than 8.0 mg/ml. In other embodiments, phenol red is absent from the NGD medium. NGD constitutes a defined serum-free medium allowing culture of multiple neural and glial cell types, as well as other cells of interest. Neural differentiation can be initiated in NGD by addition of a small molecule inhibitor of TGFβ signaling (e.g., dorsomorphin). Neural progenitors can be expanded by addition of a fibroblast growth factor (e.g., FGF2) to the NGD base and differentiation into neurons and glia (e.g., astrocytes, oligodendrocytes) can be subsequently triggered by FGF2 removal. The terms FGF2 and bFDG are used interchangeably herein.

In certain embodiments, the culture medium of the invention comprises a neurobasal culture medium, bovine serum albumin, transferrin, sodium chloride, a pyruvate salt such as sodium pyruvate, one or more antibiotics, L-alanyl-L-glutamine, biotin, ascorbic acid and lactic acid, or a salt thereof.

In certain such embodiments, the culture medium further comprises progesterone, putrescine dihydrochloride, insulin, and sodium selenite.

Exemplary neurobasal media include Neurobasal™ Medium, sold by Life Technologies, which is formulated to meet requirements of neuronal cell culture.

In certain embodiments, the culture medium of the invention comprises Neurobasal medium, Gem 21, bovine serum albumin, transferrin, progesterone, putrescine dihydrochloride, insulin, sodium selenite, sodium chloride, sodium pyruvate, L-alanyl-L-glutamine, biotin, ascorbic acid, and lactic acid.

In further embodiments, the culture medium of the invention comprises:

glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, and L-valine;

choline chloride, D-calcium pantothenate, folic acid, niacinamide, pyridoxal hydrochloride, riboflavin, thiamine hydrochloride, Vitamin B12, and i-inositol;

calcium chloride, ferric nitrate, magnesium chloride, potassium chloride, sodium bicarbonate, sodium chloride, sodium phosphate (monobasic), and zinc sulfate;

glucose;

HEPES;

bovine serum albumin;

transferrin, progesterone, putrescine dihydrochloride, insulin, and sodium selenite;

sodium chloride;

sodium pyruvate;

one or more antibiotics;

L-alanyl-L-glutamine;

biotin;

ascorbic acid; and sodium lactate.

In more particular embodiments, the culture medium comprises:

glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, and L-valine;

choline chloride, D-calcium pantothenate, folic acid, niacinamide, pyridoxal hydrochloride, riboflavin, thiamine hydrochloride, Vitamin B12, and i-inositol;

calcium chloride, ferric nitrate, magnesium chloride, potassium chloride, sodium bicarbonate, sodium chloride, sodium phosphate (monobasic), and zinc sulfate;

glucose, in a concentration of about 25 mM;

HEPES;

bovine serum albumin, in a concentration of about 2.5 g/L;

transferrin, in a concentration of about 5 µg/mL;

progesterone, putrescine dihydrochloride, insulin, and sodium selenite;

sodium chloride;

sodium pyruvate, in a concentration of about 1 mM;

L-alanyl-L-glutamine, in a concentration of about 2 mM;

biotin, in a concentration of about 3.5 µg/L;

ascorbic acid; and lactic acid, or a salt thereof, in a concentration of about 175 µg/L.

In certain embodiments, the cell culture medium of the invention further comprises Interleukin-34 (IL-34). In certain embodiments, the concentration of IL-34 is from about 5 ng/mL to about 100 ng/mL, about 5 ng/mL to about 50 ng/mL, or about 10 ng/mL. In exemplary embodiments, the concentration of IL-34 is from about 5 ng/mL to about 15 ng/mL, about 6 ng/mL to about 14 ng/mL, about 7 ng/mL to about 13 ng/mL, about 8 ng/mL to about 12 ng/mL, about 9 ng/mL to about 11 ng/mL, or about 10 ng/mL.

In certain embodiments, the cell culture medium of the invention further comprises macrophage colony-stimulating factor (M-CSF). In certain embodiments, the concentration of M-CSF is from about 2 ng/mL to about 100 ng/mL, about 2 ng/mL to about 50 ng/mL, or about 5 ng/mL. In exemplary embodiments, the concentration of M-CSF is from about 2 ng/mL to about 12 ng/mL, about 2 ng/mL to about 10 ng/mL, about 2 ng/mL to about 8 ng/mL, about 3 ng/mL to about 7 ng/mL, about 4 ng/mL to about 6 ng/mL, or about 5 ng/mL.

In certain embodiments, the cell culture medium of the invention is substantially free of one or more growth factors typically used for hematopoietic differentiation, such as EGF, FGF, GDF, IGF, PDGF, or VEGF. As used herein, the term "substantially free" means that the composition contains less than 0.5 wt %, for example less than 0.1 wt % or 0.01 wt % of the specified component.

In certain embodiments, the cell culture medium of the invention is substantially free of GM-CSF.

In certain embodiments, the cell culture medium of the invention supports the differentiation of a pluripotent stem cell into a microglial cell.

In certain embodiments, the medium of the invention further comprises a pluripotent stem cell. In certain embodiments, the medium of the invention further comprises one or more pluripotent stem cells. In certain embodiments, the medium of the invention further comprises one or more microglial cells.

It should be understood that the medium of the invention as listed in the examples is merely for illustrative purposes only. Although the medium itself is sufficient for certain intended purposes, especially differentiating microglial cells, not all components listed in these Tables may be necessary or even optimum for their intended purposes. A skilled artisan, partly depending on the particular need for differentiation of pluripotent stem cells to microglial cells, could readily determine if any listed component is necessary and/or optimum by, for example, eliminating one component or changing the concentration of one component at a time and comparing the growth/differentiation of specific type of cultured cells in such a modified medium with the original medium. In certain embodiments, one or more components may also be substituted by other chemicals of similar properties. Such modified medium without one or more non-essential/unnecessary components are within the scope of the invention. Similarly, a skilled artisan could also determine the optimal level of any given component for a particular cell differentiation, by, for example, testing a range of concentrations (e.g., 10%, 25%, 50%, 75%, 100%, 2-, 5-, 10-, 20-, 50-, 100-, 200-, 500-, 1000-fold higher, or 10%, 25%, 50%, 75%, 100%, 2-, 5-, 10-, 20-, 50-, 100-, 200-, 500-, 1000-fold lower) for each listed component based on or starting from the listed concentration of that particular component. Some components have a listed range of concentrations. The proper or optimal concentration for any particular cell differentiation can also be determined similarly starting from the listed concentration. In doing such tests, initial broad-range concentration tests may be narrowed down later based on the outcomes of the initial experiments. For example, for an initial test, the concentration of one component of interest may be changed to $10^{-3}$, $10^{-2}$, $10^{-1}$, 10-fold, 100-fold, and 1000-fold of the concentration listed in Table 1. If the $10^{-2}$ test still supports the desired growth, while $10^{-3}$ fails to, then the 10-fold concentration difference between $10^{-2}$ and $10^{-3}$ may be further explored in the second round of test to pin-point the best ranges. Thus, media so optimized for specific cell types are also within the scope of the instant invention.

As will be readily apparent to one of ordinary skill in the art, the concentration of a given ingredient can be increased or decreased beyond the range disclosed and the effect of the increased or decreased concentration can be determined using only routine experimentation. The optimization of the present media formulations for any specific cell differentiation can be carried out using approaches described by Ham (Ham, *Methods for Preparation of Media, Supplements and Substrata for Serum-Free Animal Culture*, Alan R. Liss, Inc., New York, pp. 3-21, 1984) and Waymouth (Waymouth, C., *Methods for Preparation of Media, Supplements and Substrata for Serum-Free Animal Culture*, Alan R. Liss, Inc., New York, pp. 23-68, 1984). The optimal final concentrations for medium ingredients are typically identified either by empirical studies, in single component titration studies, or by interpretation of historical and current scientific literature. In single component titration studies, using animal cells, the concentration of a single medium component is varied while all other constituents and variables are kept constant and the effect of the single component on viability, growth, or continued health of the animal cells is measured.

It will be understood that certain vitamins or hormones listed herein can exist in different forms, as known in the art (e.g., different naturally occurring or non-naturally occurring forms), and can be used as substitutes for one another. It will also be appreciated that where the instant application discloses a vitamin or hormone, the invention should be understood to encompass embodiments in which any form of such vitamin or hormone having similar biological activity (or compound(s) that can be modified or metabolized in cell culture medium or intracellularly to provide a biologically active form) is used in the inventive media and/or method(s).

The medium ingredients can be dissolved in a liquid carrier or maintained in dry form. If dissolved in a liquid carrier at the preferred concentrations shown above (i.e., a "1×formulation"), the pH of the medium should be adjusted to about 7.0-7.6, preferably about 7.1-7.5, and most preferably about 7.2-7.4. The osmolarity of the medium should also be adjusted to the preferred ranges described above, preferably by supplementation with NaCl. The type of liquid carrier and the method used to dissolve the ingredients into solution vary and can be determined by one of ordinary skill in the art with no more than routine experimentation. Typically, the medium ingredients can be added in any order.

A cell culture medium is composed of a number of ingredients and these ingredients vary from one culture medium to another. A "1×formulation" is meant to refer to any aqueous solution that contains some or all ingredients found in a cell culture medium at working concentrations. The "1×formulation" can refer to, for example, the cell culture medium or to any subgroup of ingredients for that medium. The concentration of an ingredient in a 1×solution is about the same as the concentration of that ingredient found in a cell culture formulation used for maintaining or cultivating cells in vitro. A cell culture medium used for the in vitro cultivation of cells is a 1×formulation by definition. When a number of ingredients are present, each ingredient in a 1×formulation has a concentration about equal to the concentration of those ingredients in a cell culture medium. For example, RPMI-1640 culture medium contains, among other ingredients, 0.2 g/L L-arginine, 0.05 g/L L-asparagine, and 0.02 g/L L-aspartic aced. A "1×formulation" of these amino acids contains about the same concentrations of these ingredients in solution. Thus, when referring to a "1×formulation," it is intended that each ingredient in solution has the same or about the same concentration as that found in the cell culture medium being described. The concentrations of ingredients in a 1×formulation of various cell culture media are well known to those of ordinary skill in the art. See, e.g., Methods For Preparation of Media, Supplements and Substrate For Serum-Free Animal Cell Culture Allen R. Liss, N.Y. (1984), which is incorporated by reference herein in its entirety. The osmolarity and/or pH, however, may differ in a 1×formulation compared to the culture medium, particularly when fewer ingredients are contained in the 1×formulation.

A "10×formulation" is meant to refer to a solution wherein each ingredient in that solution is about 10 times more concentrated than the same ingredient in the cell culture medium. For example, a 10×formulation of RPMI-1640 culture medium may contain, among other ingredients, 2.0 g/L L-arginine, 0.5 g/L L-asparagine, and 0.2 g/L L-aspartic acid (compare 1×formulation, above). A "10×formulation" may contain a number of additional ingredients at a concentration about 10 times that found in the 1×culture medium. As will be readily apparent, "25×formulation," "50×formulation," "100×formulation," "500×formulation," and "1000×formulation" designate solutions that contain ingredients at about 25-, 50-, 100-, 500-, or 1000-fold concentrations, respectively, as compared to a 1×cell culture medium. Again, the osmolarity and pH of the media formulation and concentrated solution may vary.

Preferably, the solutions comprising ingredients are more concentrated than the concentration of the same ingredients in a 1×media formulation. The ingredients can be 10-fold more concentrated (10×formulation), 25-fold more concentrated (25×formulation), 50-fold more concentrated (50× concentration), or 100-fold more concentrated (100×formulation). More highly concentrated formulations can be made, provided that the ingredients remain soluble and stable. See U.S. Pat. No. 5,474,931 (entire contents incorporated herein by reference), which is directed to methods of solubilizing culture media components at high concentrations.

If the media ingredients are prepared as separate concentrated solutions, an appropriate (sufficient) amount of each concentrate is combined with a diluent to produce a 1×medium formulation. Typically, the diluent used is water but other solutions including aqueous buffers, aqueous saline solution, or other aqueous solutions may be used according to the invention.

The culture media of the present invention are typically sterilized to prevent unwanted contamination. Sterilization may be accomplished, for example, by filtration through a low protein-binding membrane filter of about 0.1-1.0 μm pore size (available commercially, for example, from Millipore, Bedford, Mass.) after admixing the concentrated ingredients to produce a sterile culture medium. Alternatively, concentrated subgroups of ingredients may be filter-sterilized and stored as sterile solutions. These sterile concentrates can then be mixed under aseptic conditions with a sterile diluent to produce a concentrated 1×sterile medium formulation. Autoclaving or other elevated temperature-based methods of sterilization are not favored, since many of the components of the present culture media are heat labile and will be irreversibly degraded by temperatures such as those achieved during most heat sterilization methods.

As will be readily apparent to one of ordinary skill in the art, each of the components of the culture medium may react with one or more other components in the solution. Thus, the present invention encompasses the formulations disclosed (e.g., Table 1), supplemented as described above, as well as any reaction mixture which forms after these ingredients are combined.

The medium of the instant invention can be made from individual components separately purchased from various chemical venders. Alternatively, certain commercial medium may be conveniently mixed and supplemented by additional components for make the subject medium. For example, in one embodiment, the subject medium may comprise Neurobasal medium, supplemented with progesterone, putrescine dihydrochloride, insulin, sodium selenite, transferrin, BSA, pyruvate, one or more antibiotics, glutamine, biotin, ascorbic acid, and lactic acid, to approximately their corresponding concentrations as listed in the examples. The invention thus provides methods of making a cell culture medium by supplementing a commercially available cell culture medium by adding one or more of the components disclosed herein. For example, in some embodiments, the subject method may comprise combining Neurobasal, Gem 21, and Neuroplex N2 together with glutamine (e.g., a dipeptide comprising glutamine), biotin, ascorbic acid, lactic acid, and sodium pyruvate at approximately to the corresponding concentrations listed in Table 1.

Accordingly, in certain embodiments, the invention provides methods of making the cell culture media described herein comprising combining one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof.

In certain embodiments, the step of combining further comprises progesterone, putrescine dihydrochloride, insulin, and sodium selenite.

In certain embodiments, the step of combining further comprises one or more antibiotics.

The invention also encompasses embodiments in which any one or more of the components of such medium listed (e.g. at least 5, 6, 7, 8, 9, 10, at least 90% or all of the components) are added in the listed concentrations (or in amounts independently ranging from 0.1 to 10 times, or 0.3 to 3 times of the listed concentration), to a medium having the composition of Neurobasal™ medium. The medium may be used, without limitation, for any of the purposes and in any of the methods described herein.

The invention encompasses embodiments in which any 1, 2, 3, 4, or 5 component(s) is/are not added to the medium.

Unless otherwise indicated, as used herein, variation by up to X % means variation by ±X % with respect to the listed value. For example, if the listed value is 100 ng/ml, variation by 25% means that the value can range between 75 ng/ml and 125 ng/ml (i.e., 75-125 ng/ml). Unless otherwise indicated, where a range of values is disclosed, endpoints are included within the range. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate to any intervening value or range defined by any two values in the series, where the lowest value may be taken as a minimum and the greatest value may be taken as a maximum.

It will be appreciated that certain of the components may be provided as salts, esters, biologically active metabolites or derivatives, or as precursors that are metabolized, processed, or broken down by the cell or in the medium to yield a biologically active form of certain of the components disclosed herein. "Biologically active" in this context refers to the ability of the component to exert its desired effect on a cell when present in a cell culture medium.

In certain embodiments, the invention provides a cell culture kit, comprising: a first one or more containers together comprising a base cell culture composition, comprising:
one or more amino acids;
one or more vitamins;
one or more inorganic salts;
glucose or galactose;
buffering agent;
serum albumin;
transferrin;
sodium chloride;
a pyruvate salt;
glutamine;
biotin;
ascorbic acid; and
lactic acid, or a salt thereof; and
a second one or more containers together comprising a cytokine selected from IL-34 and M-CSF, or a combination thereof.

In certain embodiments, the first one or more containers together comprise:
glycine, L-alanine, L-arginine, L-asparagine, L-cysteine, L-histidine, L-isoleucine, L-leucine, L-lysine, L-methionine, L-phenylalanine, L-proline, L-serine, L-threonine, L-tryptophan, L-tyrosine, and L-valine;
choline chloride, D-calcium pantothenate, folic acid, niacinamide, pyridoxal hydrochloride, riboflavin, thiamine hydrochloride, Vitamin B12, and i-inositol;
calcium chloride, ferric nitrate, magnesium chloride, potassium chloride, sodium bicarbonate, sodium chloride, sodium phosphate (monobasic), and zinc sulfate;
glucose;
HEPES;
bovine serum albumin;
transferrin, optionally formulated with progesterone, putrescine dihydrochloride, insulin, and sodium selenite;
sodium chloride;
a pyruvate salt, such as sodium pyruvate;
one or more antibiotics;
L-alanyl-L-glutamine;
biotin;
ascorbic acid; and
lactic acid, or a salt thereof.

In certain embodiments, the base cell culture composition is refrigerated.

In certain embodiments, combining the contents of the first one or more containers and second one or more containers results in a culture medium wherein the cytokine is present at a concentration of about 2 ng/mL to about 100 ng/mL.

In certain embodiments, the kit further comprises instructions for using the culture medium to differentiate pluripotent stem cells into microglial cells.

The medium of the instant invention may be liquid or solid powder, or a combination of both. The liquid form may be a complete medium, which contains all the components sufficient to support the differentiation of pluripotent stem cells to microglial cells. Alternatively, the liquid media may be stored as separate packages, such that each individual package may be stored at its appropriate conditions (temperature, humidity, etc.). For example, most of the components listed in the tables (or Examples), if desired to be in a medium of the instant invention, can be pre-dissolved in a single solution and stored at appropriate conditions (e.g. 4° C. in a dark and dry place, etc.). Other components, which could be unstable at the storage conditions for the other components, or which could react slowly with other components, or which is otherwise better kept as a separate stock, may be stored under a different set of conditions (e.g. −20° C. or −80° C., etc.). It is only shortly or immediately before use are these separately stored components brought together to constitute the whole medium. Each separate package may be marketed or sold separately, or as different concentrated stocks (e.g. 2×, 5×, 10×, 100×, 1000×, etc.). In some embodiments, a medium of the instant invention is marketed or sold together with one or more cell lines (e.g., one or more cell line(s) disclosed herein, for whose culture said medium is suitable.

Similarly, the complete medium or individual components, packages thereof could be in the form of dry powder, which, upon reconstitution with an aqueous solution (such as water), will yield the desired medium, or its concentrated stocks (2×, 5×, or 10×, etc.).

Components that can be, or better kept as separate stocks just prior to use include: hormones (e.g., insulin), enzymes/proteins (e.g., transferrin), vitamins (Vitamins A, $B_{12}$, $K_3$), pH indicators (e.g., phenol red), one or more buffer components (e.g., sodium biocarbonate, HEPES), etc.

In certain embodiments, at least some or all components of the medium is in liquid/aqueous form. In other embodiments, at least some or all components of the medium is in solid/powder form.

II. Methods of Use

Another aspect of the invention relates to the use of the subject medium for differentiating a pluripotent stem cell into a microglial cell.

The term "pluripotent", as used herein, refers to a cell with the capacity, under different conditions, to differentiate to cell types characteristic of all three germ cell layers (i.e., endoderm, mesoderm, and ectoderm). Pluripotent cells are characterized primarily by their ability to differentiate to cell types of all three germ layers, using, for example, a nude mouse teratoma formation assay. Pluripotency is also evidenced by the expression of embryonic stem (ES) cell markers, although the preferred test for pluripotency is the demonstration of the capacity to differentiate into a cells of each of the three germ layers. Reprogrammed pluripotent cells (e.g., iPS cells, as that term is defined herein) also have the characteristic of the capacity of extended passaging without loss of growth potential, relative to primary cell parents, which generally have capacity for only a limited number of divisions in culture.

As used herein, the terms "iPS cell" and "induced pluripotent stem cell" are used interchangeably and refer to a pluripotent stem cell artificially derived (e.g., induced or by complete reversal) from a non-pluripotent cell, typically an adult somatic cell, for example, by inducing a forced expression of one or more genes, which may be referred to herein as "reprogramming factors." Exemplary reprogramming factors can include Oct-3/4, Sox family, Klf family, Myc family, Nanog, LIN28, and Glis1 genes.

In certain embodiments, iPS cells can be generated using vectors (e.g., viral vectors) to introduce genes encoding one or more of the reprogramming factors into a non-pluripotent cell. In certain embodiments, iPS cells are generated with the introduction of translatable modified mRNA encoding one or more of the reprogramming factors into non-pluripotent cells. In certain embodiments, small molecules can substitute for exogenous introduction of one or more reprogramming factors. In some embodiments, a non-integrating (episomal) vector may be used. Useful viral vectors include, e.g., those based on lentivirus, adenovirus, and Sendai virus. In some embodiments, an integrated vector may be excised after generation of iPS cells.

In certain embodiments, iPS cells are derived from fibroblasts or keratinocytes.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stem cells, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art.

The term "reprogramming" as used herein refers to a process that alters or reverses the differentiation state of a somatic cell. The cell can either be partially or terminally differentiated prior to the reprogramming. Reprogramming encompasses complete reversion of the differentiation state of a somatic cell to a pluripotent cell. Such complete reversal of differentiation produces an induced pluripotent (iPS) cell. Reprogramming as used herein also encompasses partial reversion of a cells differentiation state, for example to a multipotent state or to a somatic cell that is neither pluripotent or multipotent, but is a cell that has lost one or more specific characteristics of the differentiated cell from which it arises, e.g., direct reprogramming of a differentiated cell to a different somatic cell type. Reprogramming generally involves alteration, e.g., reversal, of at least some of the heritable patterns of nucleic acid modification (e.g., methylation), chromatin condensation, epigenetic changes, genomic imprinting, etc., that occur during cellular differentiation as a zygote develops into an adult.

The term "embryonic stem cell" is used to refer to pluripotent stem cells derived from the inner cell mass of the embryonic blastocyst (see U.S. Pat. Nos. 5,843,780, 6,200,806). Such cells can similarly be obtained from the inner cell mass of blastocysts derived from somatic cell nuclear transfer (see, for example, U.S. Pat. Nos. 5,945,577, 5,994,619, 6,235,970). Embryonic stem cells can also be derived from earlier stages of the embryo, e.g., from a morula. The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

Numerous human ES and human iPS cells are known in the art. The methods described herein can be applied to generate microglia from such known cells.

In certain embodiments, the invention includes methods of differentiating a pluripotent stem cell into a microglial cell, comprising:
a) contacting a pluripotent stem cell with a passaging reagent in the presence of a culture medium of the invention, thereby forming a differentiation culture; and
b) incubating the differentiation culture of step a);
thereby differentiating the pluripotent stem cell into a microglial cell.

In certain embodiments, the pluripotent stem cell is an embryonic stem cell. In certain embodiments, the pluripotent stem cell is an induced pluripotent stem cell. Preferably, the pluripotent stem cell is a human stem cell.

The passaging reagent may be collagenase IV, trypsin, dispase, or accutase. Preferably, it is collagenase IV.

In certain embodiments, the culture medium further comprises dorsomorphin.

In certain such embodiments, the culture medium further comprises a pluripotent stem cell.

The invention also provides methods for deriving a neural progenitor cell from a pluripotent stem cell, comprising:
a) contacting a pluripotent stem cell with the culture medium of the invention, further comprising dorsomorphin, to form an incubation mixture; and b) incubating the mixture of step a) to form a neural progenitor cell.

Most traditional culture cell container surfaces are negatively charged (see the numerous —COOH groups below, which, at neutral pH, tend to slightly dissociated and assume a negative (anionic) charge). This leads to poor attachment of the cells to the container surfaces, and thus preferably should not be used. Suitable tissue culture container with mixed charges include both positive (see the —NH$_2$ groups, which may protonate and assume a positive charge (cationic) at neutral pH) and negative charges (see the —COOH groups and above). BD Primaria™ Cultureware (BD Biosciences) manufactures such mixed-charge tissue culture containers.

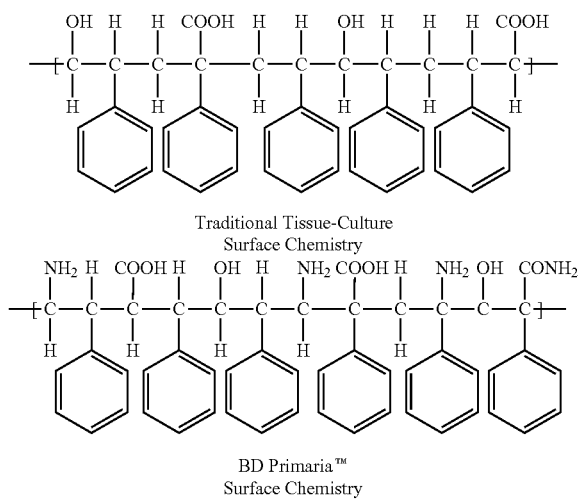

Traditional Tissue-Culture Surface Chemistry

BD Primaria™ Surface Chemistry

An alternative method is to coat the cell culture surface with BD Matrigel™ matrix (BD Biosciences), a solubilized basement membrane preparation extracted from EHS mouse sarcoma, a tumor rich in ECM proteins. Its major component is laminin, followed by collagen IV, heparan sulfate proteoglycans, and entactin. Other Matrigel™ equivalents may also be used.

Certain methods of the invention include differentiating a pluripotent stem cell into a microglial cell using a culture medium described herein. In certain of these methods, pluripotent stem cells (e.g., embryonic stem cells, or induced pluripotent stem cells) are cultured on a suitable surface (e.g., BD Primaria™) for a suitable time (e.g., 2-14 days, 5-12 days, or 7-10 days). The stem cells can then be dissociated from the culture surface by first treating the container with a passaging reagent (e.g., collagenase IV or trypsin). This passaging step generates embryoid bodies, which are then further cultured, allowing microglial-like cells to shed from the embryoid bodies. The embryoid bodies may also be triturated to shed additional microglial-like cells. The term "differentiation culture" as used herein, includes the embryoid bodies. Such process can be repeated in order to shed further microglial-like cells. The microglial cells may be maintained in a microglial maturation medium. In certain embodiments, the microglial maturation medium comprises one or more amino acids, one or more vitamins, one or more inorganic salts, glucose or galactose, buffering agent, serum albumin, transferrin, sodium chloride, a pyruvate salt, glutamine, biotin, ascorbic acid, and lactic acid, or a salt thereof; and further comprises about 100 ng/mL IL34 and about 5 ng/mL MCSF. MCSF and CSF1 are used interchangeably herein.

In certain embodiments, the microglial cells are derived from pluripotent stem cells, or are maintained, in culture conditions of from about 0.5% to about 10% $O_2$. In certain embodiments, the microglial cells are derived from pluripotent stem cells, or are maintained, in culture conditions of from about 1% to about 9%, about 1% to about 8%, about 2% to about 7%, about 2% to about 6%, about 2% to about 5%, about 2% to about 4%, about 2% to about 3%, about 3% to about 8%, about 3% to about 7%, about 3% to about 6%, about 3% to about 5%, or about 3% to about 4% $O_2$. In certain embodiments, the microglial cells are derived from pluripotent stem cells, or are maintained, in culture conditions of from about about 1% to about 5%, about 1% to about 4%, about 2%, or about 3% $O_2$.

Disclosed herein are methods for preparing a co-culture of microglial cells, neurons, and glia, comprising (a) contacting a population of microglial cells (e.g., pluripotent stem cell-derived microglia-like cells (pMGLs)) with differentiated neural cells (e.g., neurons, astrocytes, and/or oligodendrocytes), and (b) co-culturing the cells on a solid support to promote the formation of clusters having microglial cells embedded in clusters of neurons and glia. In some embodiments, the microglial cells may be prepared by differentiating a pluripotent stem cell into a microglial cell (e.g., contacting a pluripotent stem cell with a passaging reagent (e.g., collagenase IV, trypsin, dispase, or accutase) in the presence of the culture medium as disclosed herein, and incubating the differentiation culture, thereby differentiating the pluripotent stem cell into a microglial cell), or by any other suitable method, including those disclosed herein. The pluripotent stem cell may be cultured in a medium (such as a culture medium as described herein) on a solid support (e.g., a primaria plastic plate). The pluripotent stem cell may be, for example, an embryonic stem cell, induced pluripotent stem cell, or a human stem cell.

Also disclosed herein are methods of preparing a substantially uniform population of pluripotent stem cell-derived microglia-like cells (pMGLs). A "substantially uniform population" refers to a population of cells in which at least 80% of the cells are of the indicated type, preferably at least 90%, 95%, or even 98% or more. In some embodiments, the pMGLs may be prepared by differentiating a pluripotent stem cell into a pMGL (e.g., contacting a pluripotent stem cell with a passaging reagent (e.g., collagenase IV, trypsin, dispase, or accutase) in the presence of the culture medium as disclosed herein, and incubating the differentiation culture, thereby differentiating the pluripotent stem cell into a pMGL, e.g., by any of the methods described herein. The pluripotent stem cell may be cultured in a medium on a solid support (e.g., a primaria plastic plate). The pluripotent stem cell may be an embryonic stem cell, induced pluripotent stem cell, or a human stem cell.

In a recent comparison of mouse primary microglia generated from an earlier method [1], ES cell-derived microglial precursors (ESdMs) did not express many of the canonical markers of microglial identity. Conversely, human counterpart precursors generated from hES and hIPS cells using the culture media and methods described herein follow a much clearer differentiation path, and adopt microglial identity. By comparison, the protocol described herein allows production of these cells in 4-8 weeks, from human cells, matching embryonic development. These cells are generated in a single optimized serum free medium, directly from the pluripotent state. The protocol of the invention is highly scalable at the onset, and allows routine production of large quantities of cells amenable to further study or other uses. In the context of xeno-free cultures, these microglia have potential for application as a therapeutic vehicle for transplantation into patients.

The invention described herein has numerous therapeutic applications. In particular, remitting/relapsing multiple sclerosis courses may depend on pro- and anti-inflammatory profiles from key players, especially microglia. Similarly, Lou Gherig's disease (ALS), a disorder of motor neurons, is currently primarily modeled through astrocyte/neuron co-cultures, though microglia and oligodendrocytes deserve more attention. In Alzheimer's disease, genome-wide association studies are highlighting microglial genes such as TREM2 and CD33. Microglia are capable of clearing amyloid, and/or causing cell death. These genes are ideal targets for isogenic modeling using genome engineering methods. Such methods may be applied to any gene expressed in microglia, e.g., genes identified in genome-wide association studies or other genetic studies as being implicated in one or more diseases or disorders. Furthermore, because microglia are life-long residents of the nervous system, highly oxidative, and crucial to the brain's homeostasis, microglia are a prime target for a host of age-related dysfunctions.

Furthermore, differentiation of microglial cells from iPS cells that have been derived from a patient can be used in therapeutic applications in personalized medicine. For example, iPS cells (e.g., iPS cells having a selected genetic modification) can be generated, differentiated into microglia, and the microglia can then be used as a therapy for a disease or disorder, e.g., in the patient from whom the iPS cells were derived.

In certain embodiments, microglia derived using the methods of the invention are used in the treatment of diseases or disorders such as neuroinflammation (e.g., chronic neuroinflammation), neurodegeneration, Alzheimer's disease, Prion disease, schizophrenia, Parkinson's disease, Nasu-Hakola disease (also referred to polycystic lipomembranous osteodysplasia with sclerosing leukoencephalopathy), cardiovascular disease such as myocardial infarction, human immunodeficiency virus infection, herpes simplex virus infection, bacterial infections, viral infections, stroke, traumatic brain or spinal cord injury.

In some embodiments, the microglia, neural progenitor, neuron, or macroglial (e.g., an astrocyte) derived cell obtained or cultured as described herein are used to identify agents for treatment or prevention of a viral infection. In some embodiments, the culture medium composition comprises a virus and the culture medium described herein. In some such embodiments, the virus is capable of infecting a microglia, neuron, and/or macroglial cell (e.g., astrocytes, oligodendrocytes). In some embodiments, the virus is from the Retroviridae family of viruses (e.g., a lentivirus, such as human T-lymphotropic virus-1 (HTLV-1) or HIV). In some embodiments, the virus is from the Herpesviridae family of viruses (e.g., herpes simplex virus (HSV), varicella zoster virus (VZV), Epstein Barr virus (EBV), cytomegalovirus (CMV), or human herpes virus-6 (HHV-6). In some embodiments, the virus is from the Picornaviridae family of viruses (e.g., nonpolio enterovirus, poliovirus, human parechovirus). In some embodiments, the virus is from the Paramyxoviridae family of viruses (e.g., measles virus, mumps virus). In some embodiments, the virus is from the Rhabdoviridae family of viruses (e.g., rabies virus). In some embodiments, the virus is from the Flaviridae family of viruses (e.g., Zika virus, dengue virus, West Nile Virus, Yellow Fever, or Japanese Encephalitis virus, Togaviridae (e.g., Eastern equine encephalitis virus, chikungunya virus). In some embodiments, the methods of the invention are used to screen for an agent that inhibits the release of one or more inflammatory mediators (e.g., TNF-alpha, IL-6, IL-1beta) by microglial-like cells that have been infected by a virus or exposed to an activating stimulus (e.g., an endotoxin). In some embodiments, the agent is a small molecule. In some embodiments, the microglia, neural progenitor, neuron, or macroglial (e.g., an astrocyte) derived cell is contacted with a virus prior to contact with an agent. In some embodiments, the time between virus contact with the cell and agent contact with the cell is at least 1 minute, 5 minutes, 10 minutes, 20 minutes, 30 minutes, 45 minutes, 1 hour, 2 hours, 3 hours, 4 hours, 5 hours, 10 hours, 15 hours, 20 hours, 24 hours, or 48 hours. In some embodiments, the microglia, neural progenitor, neuron, or macroglial (e.g., an astrocyte) derived cell is contacted with a virus at the same time as being contacted with an agent; in other embodiments, the microglia, neural progenitor, neuron, or macroglial (e.g., an astrocyte) derived cell is contacted with a virus after contact with an agent. In some embodiments, the time between virus contact with the cell and agent contact with the cell is at least 1 minute, 5 minutes, 10 minutes, 20 minutes, 30 minutes, 45 minutes, 1 hour, 2 hours, 3 hours, 4 hours, 5 hours, 10 hours, 15 hours, 20 hours, 24 hours, or 48 hours.

In certain embodiments microglia derived using methods of the invention are administered to a mammalian subject, e.g., to the central nervous system of a mammalian subject. In certain embodiments microglial cells are administered to the brain. In certain embodiments microglial cells are administered by introducing them into an artery, vein, ventricle of the brain, brain parenchyma, or the spinal canal. In certain embodiments the subject is a non-human mammal. In certain embodiments the non-human mammal serves as an animal model for a disease or disorder that affects humans.

In certain embodiments, microglia derived using methods of the invention are used as models for one or more diseases or disorders. Such models can be used for a variety of purposes. For example, they may be used to study the pathogenesis of the disease or disorder and/or may be used to identify candidate therapeutic agents for treating the disease or disorder. In certain embodiments, microglia derived using methods of the invention are used to evaluate the potential response of a patient from whom such microglia are derived to a therapeutic agent. For example, microglial cells derived from a particular patient and/or harboring a particular mutation could be used for drug screenings to find agents (e.g., small molecules) which specifically reverse or inhibit disease-associated phenotypes.

In some embodiments iPS cells are derived from a patient whose genome harbors a particular mutation that causes or contributes to a disease or disorder. In some embodiments, iPS cells derived from a patient are genetically modified to "correct" a mutant sequence to a normal sequence prior to generation of microglial cells. In some embodiments, iPS cells derived from the patient are genetically modified to alter a mutant sequence to a normal sequence prior to generation of microglial cells. In some embodiments, iPS cells derived from the patient are genetically modified to introduce a transgene of interest or generate a mutation of interest. Microglial cells derived from such iPS cells can then be used to assess the effect of the transgene or mutation on any one or more microglial phenotypes or functions.

One of ordinary skill in the art is aware of suitable methods that can be used to produce genetic modifications in mammalian cells, e.g., in pluripotent human stem cells. In some embodiments, for example, targetable nucleases such as zinc fingers, transcription activator-like effector nucleases (TALENs), or RNA-guided nucleases such as Cas9 may be used to introduce one or more breaks (e.g., double-stranded break) in genomic DNA at or near a selected location. Such breaks can be repaired by nonhomologous end joining, which can create small deletions to produce targeted gene disruption or via the homology-directed DNA repair pathway using an ectopically provided donor DNA as a template. Depending on the donor design, this repair reaction can be used to generate large-scale deletions, gene disruptions, DNA addition' or single nucleotide changes. In some embodiments, the genetic modification comprises introducing a nucleic acid that encodes a protein or RNA of interest into an iPS cell, which is then used to generate microglial cells as described herein. In certain embodiments CRISPR-Cas technology is used to produce a genetic modification of interest in a pluripotent human stem cell, which is then used to generate microglial cells as described herein.

EXAMPLES

The following examples are for illustrative purposes only, and should not be construed to be limiting in any respect of the claimed invention.

Example 1: Neuro-Glial Differentiation Protocol

Media Considerations:

Given the complexity of the cellular interactions to model, a lot of efforts have been dedicated to obtaining the proper cell types, and identifying substrate and media allowing long term culture of these cells, preferably in a single basal condition for co-culture. In particular, these different cell types require specific metabolic substrates. We made sure the basal medium would include fatty acids (Albumax II and Gem21), along with the necessary biotin and L-carnitine crucial for their metabolism. The lower glucose content of DMEM/F12, was detrimental to most cell types, thus we favoured a high glucose solution. Lactic acid is thought to be a major energy substrate for neurons, along with glutamine and pyruvate, those were added. Unconjugated iron and iron salts are redox-active and deleterious to various cells through Fenton chemistry, thus we opted for iron delivery through holo-transferrin supplementation alone (NS21). In the end, neurobasal proved to be a good all-purpose medium, however it yielded osmolarities in the 250 mOsm range, much lower than what is needed with rapid feeding schedules, for human cells. Thus we supplemented the medium with sodium chloride, in amounts compatible with CSF concentration, to raise the osmolarity to 300 mOsm. Finally, the cells were usually generated and kept in 5% oxygen, to mimic the tissue environment, and limit the effects of oxidative processes which may mask some of the disease phenotypes.

|  | for 500 mL NBm | for 500 mL NBd |
|---|---|---|
| Gem21 | 10 mL | 5 |
| Albumax II 20% |  | 5 |
| Neuroplex N2 | 5 mL | 2.5 |
| NaCl 5M | 5 mL | 5 |
| pyruvate 100x | 5 mL | 5 |
| Pen/Strep | 5 mL | 5 |
| Glutamax | 5 mL | 5 |

|  | for 500 mL NBm | for 500 mL NBd |
|---|---|---|
| Biotin (5 mg/mL in 1M NaOH) | 0.35 uL | 0.35 uL |
| ascorbic (100 mM stock) | 50 uL | 50 uL |
| lactic syrup (85%) | 100 uL | 100 uL |

Neuralization:

pluripotent cultures maintained on feeders are single-cell dissociated in PBS (w/o $Ca^{2+}$ and $Mg^{2+}$), and plated on matrigel in mTesR at a density of 200 k/cm² (day 0). After 24 hours, the medium is changed to a neurobasal-based medium supplemented with pyruvate (1 mM), glutamax 1×, lactate, ascorbic acid, biotin, Albumax 0.2%, N2 0.5× and Gem21 (−VitA) 0.5×, adjusted to an osmolarity of 300 mOsm with NaCl (NBd). On Day 2, NBd is supplemented with 2.5 uM Dorsomorphin, providing TGFb inhibition, forcing neuro-ectodermal differentiation at the expense of other lineages. Medium is changed daily, and feeding routinely done with up to 10 mL of medium in a 35 mm dish: cells at this stage have very high metabolic needs resulting in lactic acidosis. At day 4, neural rosette structures emerge in the layers of differentiated cells covering the original pluripotent monolayer. By day 7-10, rosettes are confluent in the well, and Pax6+ cells represent >90% of the culture. These early neural progenitor cells are dissociated in PBS (⁻/_), avoiding complete dissociation, in order to maintain seeding of rosettes structures. Rho-kinase inhibition is necessary during the first two passages to prevent massive cell loss by apoptosis. Dorsomorphin is also removed at that stage. These first passages follow a split ratio of no more than 1:2. Low density passage allows the emergence of neural crest stem cells delaminating between the rosette clusters. Around day 15, the base medium can be switched to a maintenance medium starting from the NBd base, adjusting to 1×N2 and NS21 supplements, along with 10 ng/mL bFGF (NBm). Neural progenitors (NPCs) obtained through this method are FGF-dependent only and are multipotent.

Neuronal Differentiation:

NPCs maintained in NBm medium can differentiate readily into neurons when FGF is removed, and insulin is lowered, without retinoic acid addition. $2*10^7$ cells are plated on 1% matrigel in a T75, fed 15 mL of NBd every 2-3 days. After 4 weeks, neurons are evident in the culture and a final dissociation is performed. Dissociation beyond that stage will be more damaging to neurons as they mature. The culture is dissociated by incubation with accutase for 30' at 37 C with gentle agitation (bacterial rotator), in the presence of 0.05% DNaseI, re-suspended in chilled HBSS/0.1% BSA, filtered through a 40 uM mesh before being centrifuged through a cushion of 4% BSA to remove debris. Cells are re-plated around at 100-500 k/cm^2 on 0.1% PEI-coated plastic or glass. PEI provides strong and long lasting attachment for neurons and neurites, guaranteeing cell dispersal, preventing clumping. Within a week of replating, cells will have re-extended a complex network of neurites. These neurites are either MAP2+ (dendritic arbors), or Tuj1+ (throughout). After 6 weeks, synaptic puncta are seen, and electrical activity is measurable. A secondary burst of glial differentiation from progenitors can be prevented using anti-mitotic agents such as Ara-C. Most cells are glutamatergic cells, with few Gaba-ergic neurons by default. Further lineage fating can be performed if need be (for example caudalization and ventralization using retinoic acid and Shh will yield spinal motor neurons).

Glial Expansion:

glial differentiation is obtained from the NPC stage by keeping the original medium, without dorsomorphin, and plating the cells at 500 k/cm² on matrigel coated dishes. After 2 weeks without splitting, neuronal processes are apparent in the dish, along with mitotic foci of multipotent precursors (in particular glial-restricted progenitors). At that point, glial-restricted progenitors already constitute 20% of the culture, while neurogenesis is taking place. The culture is dissociated by incubation with accutase for 30' at 37 C with gentle agitation (Bacterial rotator), in the presence of 0.05% DNaseI, re-suspended in HBSS/0.1% BSA, filtered through a 40 uM mesh before being centrifuged through a cushion of 4% BSA to remove debris. At that point, PSA-NCAM−/A2B5+ cells are magnetically sorted according to the manufacturer's instruction (Miltenyi MACS): incubation with anti-PSA-NCAM antibody-conjugated microbeads yields a negative flow-through fraction on an AutoMACS separator. These cells are spun down and re-suspended with anti-A2B5 antibody-conjugated microbeads. The retained PSA-NCAM−/A2B5+ cells are eluted and plated at low density on matrigel (100 k/cm²), and correspond to glial progenitors (GPC) with the potential to differentiate into oligodendrocytes or astrocytes.

Figure 6:
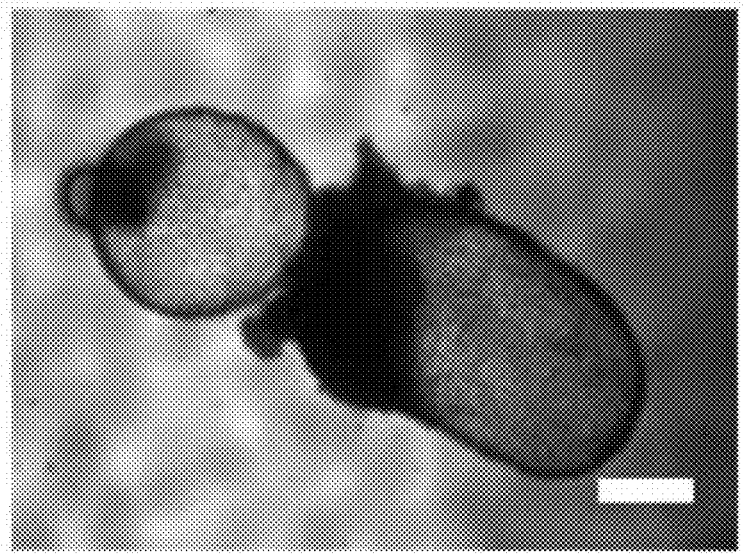
FIG. 6 shows induction of primitive myelogenesis from human pluripotent stem cells.
Figure 6:
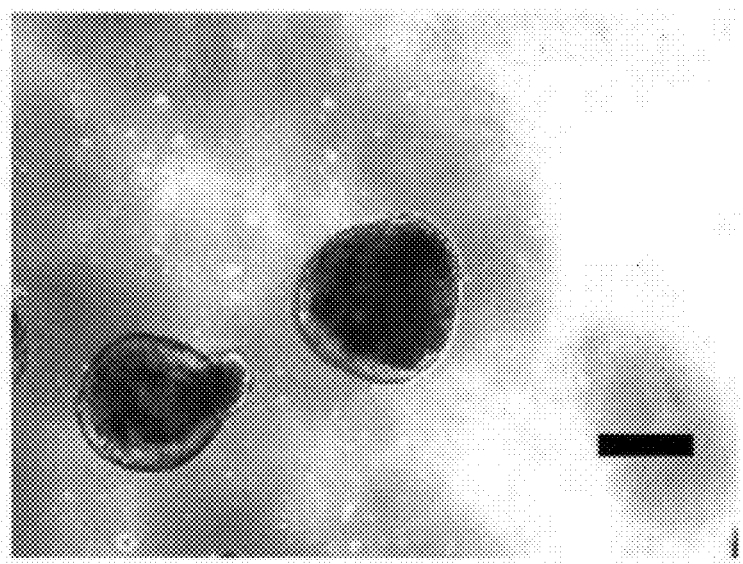
Figure 6:
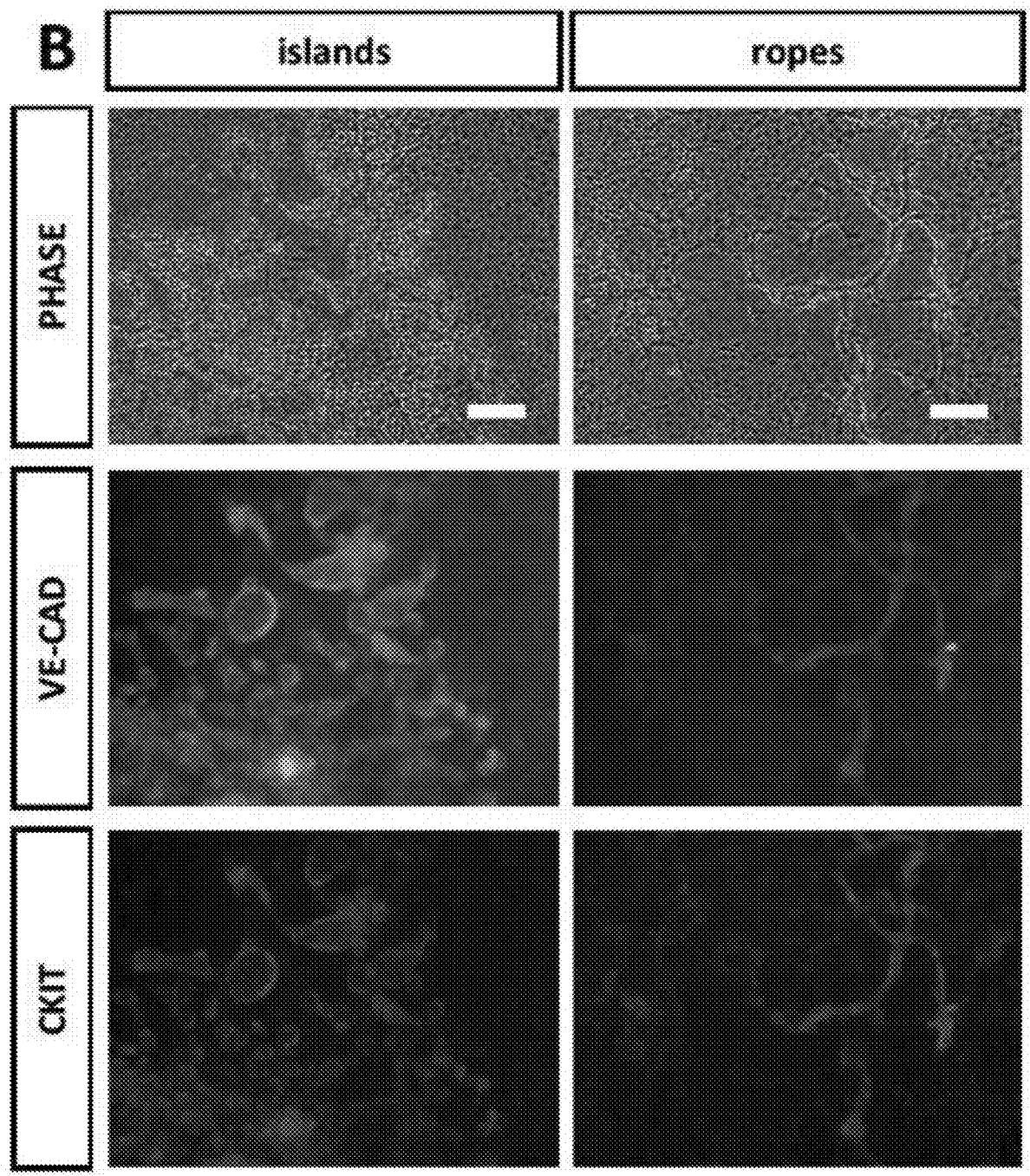
Figure 6:
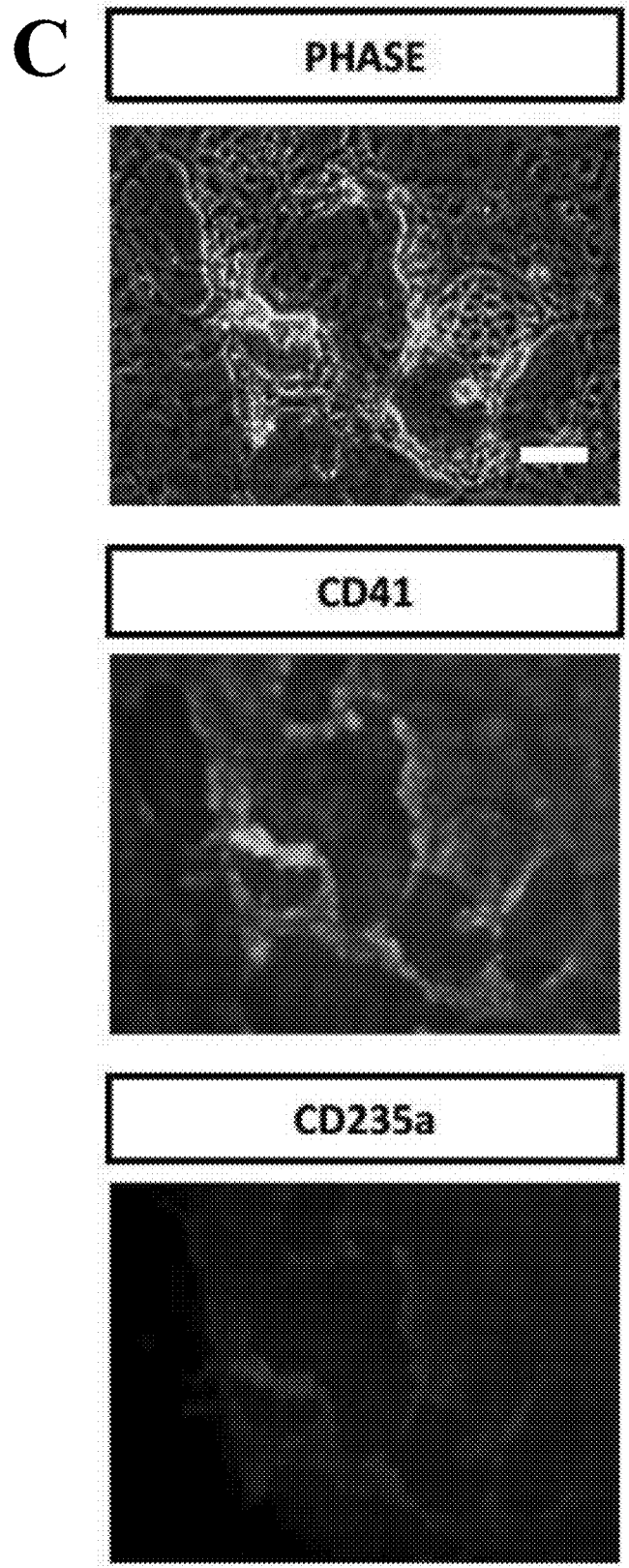
Figure 6:
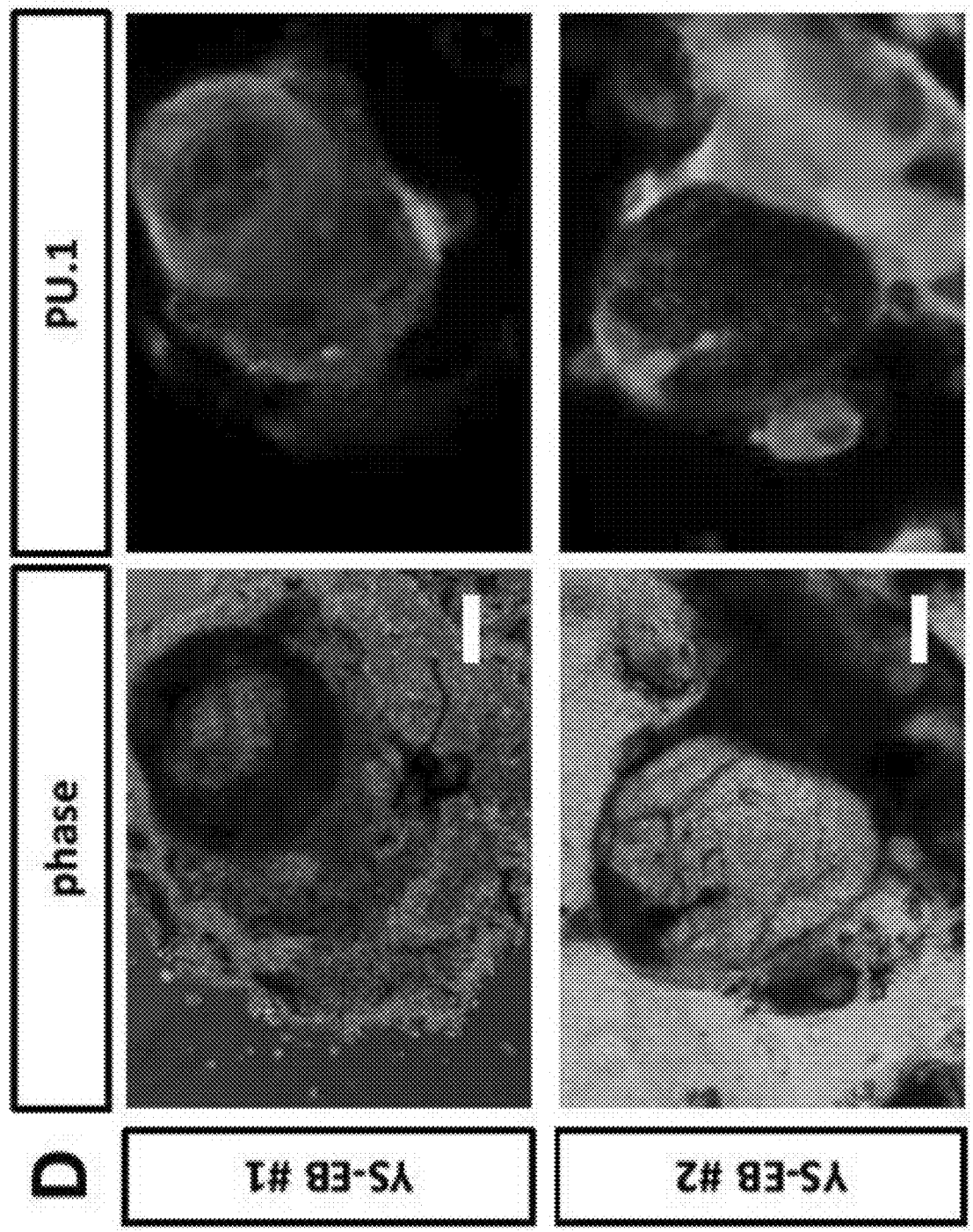
Figure 6:
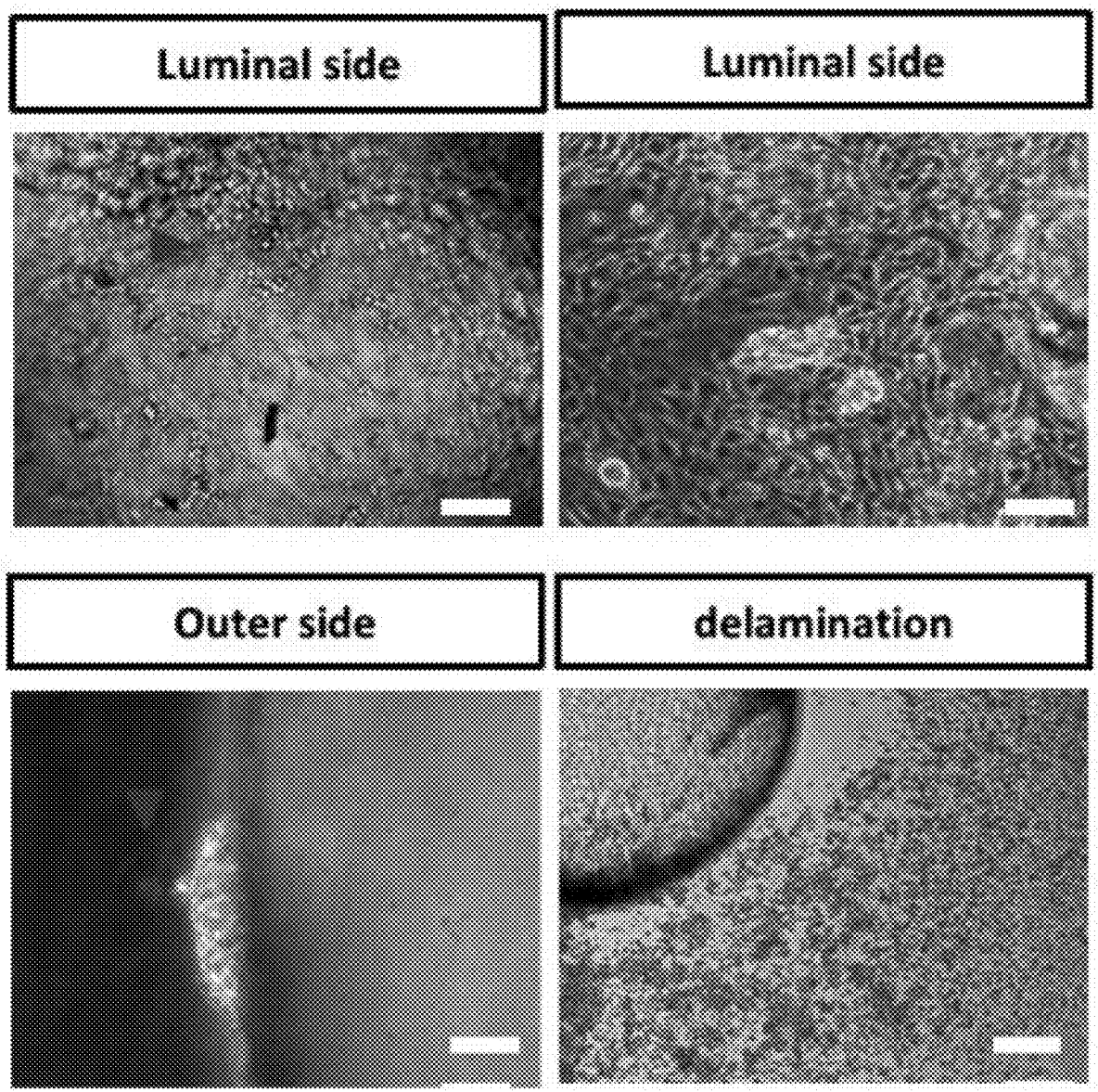

Astrocytic Differentiation:

GPCs are grown on 1% matrigel, in neural medium containing 1×N2 (No Gem21 to avoid T3 induced oligodendrocyte fates), 10 ng/mL EGF and FGF (NBAm). Between day 30 and 60, the cells adopt characteristic astrocytic morphology, with large prominent nuclei and wide-spread cytoplasmic veils, reaching monolayer confluency on matrigel. These cells are mitotic, can be passaged when confluent, and express both S100b (FIG. 6) and CD44. They can be sorted as astrocytic progenitors using the CD44 epitope. Maturation into GFAP astrocytes occurs after removal of EGF and FGF, and addition of 10 ng/mL CNTF and/or 10 ng/mL BMP4 to the base medium (NBAd). Alternatively, 2% FBS supplement can be used.

Oligodendrocyte Differentiation:

A2B5+ GPCs are grown in NBm supplemented with 10 ng/mL PDGF and 50 ng/mL T3 (NBOm). When confluent they may spontaneously form spheres which can be maintained as such (oligospheres). Plated on 1% matrigel-coated plastic, they will grow as adherent cultures of phase-bright bipolar cells. Additional sorting for CD140a can be used to select cells with myelinating potential, although the presence of PDGF has naturally expanded the PDGFR+ subpopulation. Upon removal of PDGF and FGF, the cells will begin to differentiate in NBd supplemented with 50 ng/mL of T3. Some become astrocytic, however over the following months most will adopt an oligodendroglial fate and progressively express antigens such as O4, followed by O1 and MBP. As this differentiation progresses, branching increases markedly, and O1/MBP positive cells extend myelin veils on the matrigel surface. Lipids necessary for oligodendroglial differentiation are provided by Albumax II and Gem21, supplemented with biotin. Most of the iron present in the system comes from the holotransferrin in NS21.

Example 2: Microglial Differentiation Protocol hiPS or hES Cells are grown on mouse IMR90 feeders until confluent, with minimal differentiation. Cultures are grown grow in hES medium with 15% FBS, 5% KSR in DMEM/F12 (FGF 4 ng/mL, +bME/NEAA) on gelatinized MEF plates at 40 k cells/cm$^2$. Cells are kept in 5% $O_2$/5% $CO_2$ atmosphere. They can alternatively be grown in serum free conditions (including mTesR medium, or E8 medium)
Reagents:
  Primaria 6 well plates from Corning/BD
  ULA plates from Corning/BD
  Neuroplex N2 supplement from Gemini Bio
  Gem21—VitA supplement from Gemini Bio
  rhIL34 from preprotech
  rhMCSF from preprotech
  TGFb from preprotech
  Albumax II (life)
  Pyruvate (100×, life)
  NaCL 5M (ambion/life)
  Glutamax
  Biotin (sigma)
  Ascorbic acid (sigma)
  Lactic syrup (sigma)
  bFGF from life technologies
  For conditioned medium: astrocytes derived from ES or iPS, or primary human astrocytes, and NPCs derived from ES or iPS cells.
1) at t=−1 Day:
  hES medium is replaced with NBd+IL34 (10 ng/mL)+MCSF (5 ng/mL): this is the microglial differentiation medium (MdM). NBd is matched to the osmolarity and main component of the hES medium, thus allowing direct transition. This may need to be adapted to other culture systems. We have had success starting from feeder-free cells in mTesR1. Other concentrations, from 5 to 100 ng/mL, can also be used and favor proliferation of the cells of interest.

|  | for 500 mL NBm | for 500 mL NBd |
| --- | --- | --- |
| Gem21 |  | 10 mL | 5 |
| Albumax II 20% |  | 5 |
| Neuroplex N2 | 5 mL | 2.5 |
| NaCl 5M | 5 mL | 5 |
| pyruvate 100x | 5 mL | 5 |
| Pen/Strep | 5 mL | 5 |
| Glutamax | 5 mL | 5 |
| Biotin (5 mg/mL in 1M NaOH) | 0.35 uL | 0.35 uL |
| Ascorbic acid (100 mM stock) | 50 uL | 50 uL |
| lactic syrup (85%) | 100 uL | 100 uL |

2) At t=0 Day
Colonies are treated with collagenase IV (1.5 mg/mL) and mildly triturated to form a suspension of clumps, grown in 5 mL MdM, in ultra-low attachment plates. From a healthy culture, 2 confluent wells (~1×10^6 cells) can be pooled into one suspension well. Alternatively, aggregates of a specific cell number can be generated using 10000 to 100000 cells per aggregate.

These embryoid bodies are monitored for appearance of two main identifiable groups. The first group is composed of compact phase-bright neuralized spheroids, classically seen in neural differentiation protocols. While they may influence differentiation they are not the origin of the cells of interest.

The second group are large, expanding, cystic bodies, which we termed yolk-sac organoids (YSO), recapitulating some features and expressing markers of early yolk sac embryogenesis (e.g.: PU.1 staining).

These distinctions are clear as early as day 10 of suspension culture, but may vary between cell lines.

From those yolk-sac organoids, we eventually observe obvious delamination of mitotically active cells that stain for macrophage markers (pu.1, lectins, etc.) and eventually adopt microglia-like characteristics. Healthy culture will make EBs with minimal shedding, and should transition very easily. Heavy shedding in the first couple of days should be cleared by resuspension.

3) At t=7 Days
  a) pipette the whole 5 mL of medium and YSOs, triturate at slow speed 5 times into a 15 mL falcon tube
  b) let YSOs settle and move the supernatant containing loose cells to a new tube.
  c) Take the YSO pellet and resuspend in fresh MdM, place back into the ULA plate for further differentiation and production.
  d) UNDERLAY 5% BSA/HBSS solution as a cushion below the supernatant from step b) (use Pasteur pipette)
  e) Spin cells through the cushion, at 300 g for 5' at 4 C, to remove cellular debris
  f) Vacuum away supernatant including BSA cushion/gradient.
  g) Resuspend pellet into 2 mL of MdM, plate into one well of a primaria plate
  h) Let cells attach 6 hours (to overnight), and replace with fresh MdM.
  i) Feed attached cells every 3-5 days depending on density, and monitor for attachment of microglia-like cells.

4) At t=12 Days, 17 d, 22 d, 27 d Etc. . . .
Every 5 days, gentle trituration sheds cells of interest from the organoids.

Figure 1B:
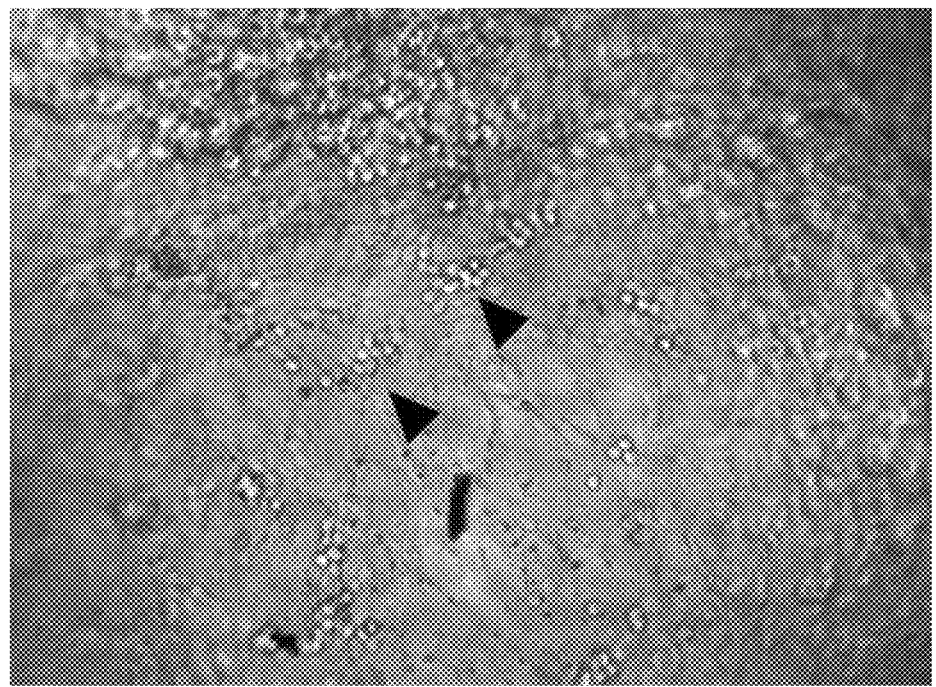
FIG. 1B is an image showing the phase contrast of the lumen of the embryoid body (EB). The cells are budding (arrowheads), rounding up from the wall of the EB: this is reminiscent of EMP formation in yolk sac blood islands and endothelial budding of HSCs.

The process is repeated. The cells of interest coincide with the presence and expansion of these YSOs, which become very large (3-5 mm). The delaminating cells can be seen shedding into the suspension, often on the INNER surface of the YSOs, as seen by phase contrast (FIG. 1A and FIG. 1B).

The trituration is thus intended to open up the YSOs, evaginate them, and release the cells of interest. They YSOs subsequently reform and re-pressurize.

More rarely, despite the ULA coating, some cells of interest attach to the plastic, especially if the surface is scratched. This can be a convenient way to monitor progress, as the only cells managing to anchor themselves appear to be microglia-like.

Figure 2:
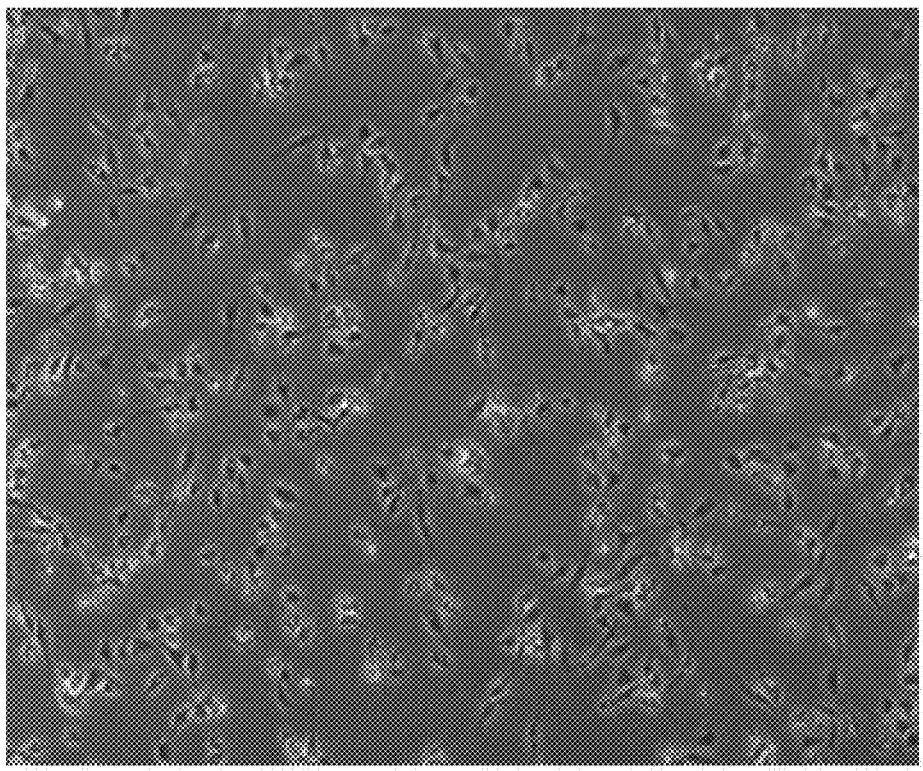
FIG. 2 is an image in which purified microglia-like cells can be readily identified. They are migratory, with a phase dark condensed nucleus, cytoplasmic granules and vacuoles. They cycle very slowly, and become more ramified as they mature. Some may be very phase bright, and loosely adherent.

Of note, the PRIMARIA surface is the only one tested which allows good discrimination of microglia-like cells from any other neuro-glial contaminants, and allows them to have a canonical morphology for label-free identification (FIG. 2).

Embryonic bodies (EBs) and YSOs should grow throughout the procedure, and their numbers should not decrease. Depletion would most likely be due to poor culture conditions of the pluripotent cells, improper adaptation to the new medium, genomic abnormalities preventing differentiation and/or occult contaminations.

One primaria plate allows collection of 6 "timepoints", covering a month of YSO shedding. This has been sufficient for most of the lines, although some can require longer periods of differentiation (up to 2 months). The production peaks after a few weeks, and declines.

Wells should not contain contaminants, except for occasional large foam cells, macrophages, which do not grow and can be eliminated by scratching with a pipette tip. Microglia like cells loosen their adherence and care must be taken when changing medium to keep the cells in suspension. Replate such supernatants on fresh primaria (B samples), floating cells will adhere to the new substrate.

The cells of interest do not proliferate much once isolated but are long lived (several months in culture). The production was pooled from 3 time points. Pooling should be done so as to achieve 50% confluency in a new vessel, and no more. Passaging should be done with accutase, or PBS-EDTA whenever confluency exceeds 60% if cell division occurs. Microglia-like cells tile and separate from each other by at least one cell diameter. Thus the maximum density is usually 50000 cells/cm$^2$.

If other cell type contaminants compete in the culture, microglia-like cells can usually be selectively passaged mechanically. Magnetic bead sorting for CD11b or CX3CR1 can be used instead.

Figure 3:
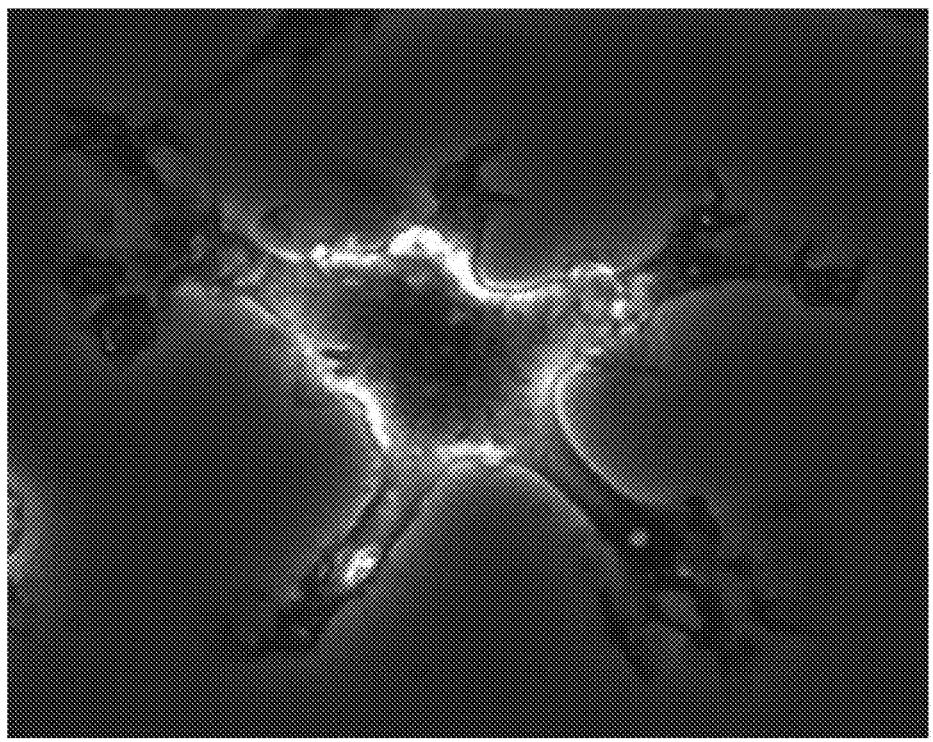
FIG. 3 is a high magnification image of a ramified microglia-like cell. The cell body is static, but the processes are highly motile, with readily observable movements of veils, filopodia, membrane ruffles and phagocytic cups.
Figure 4:
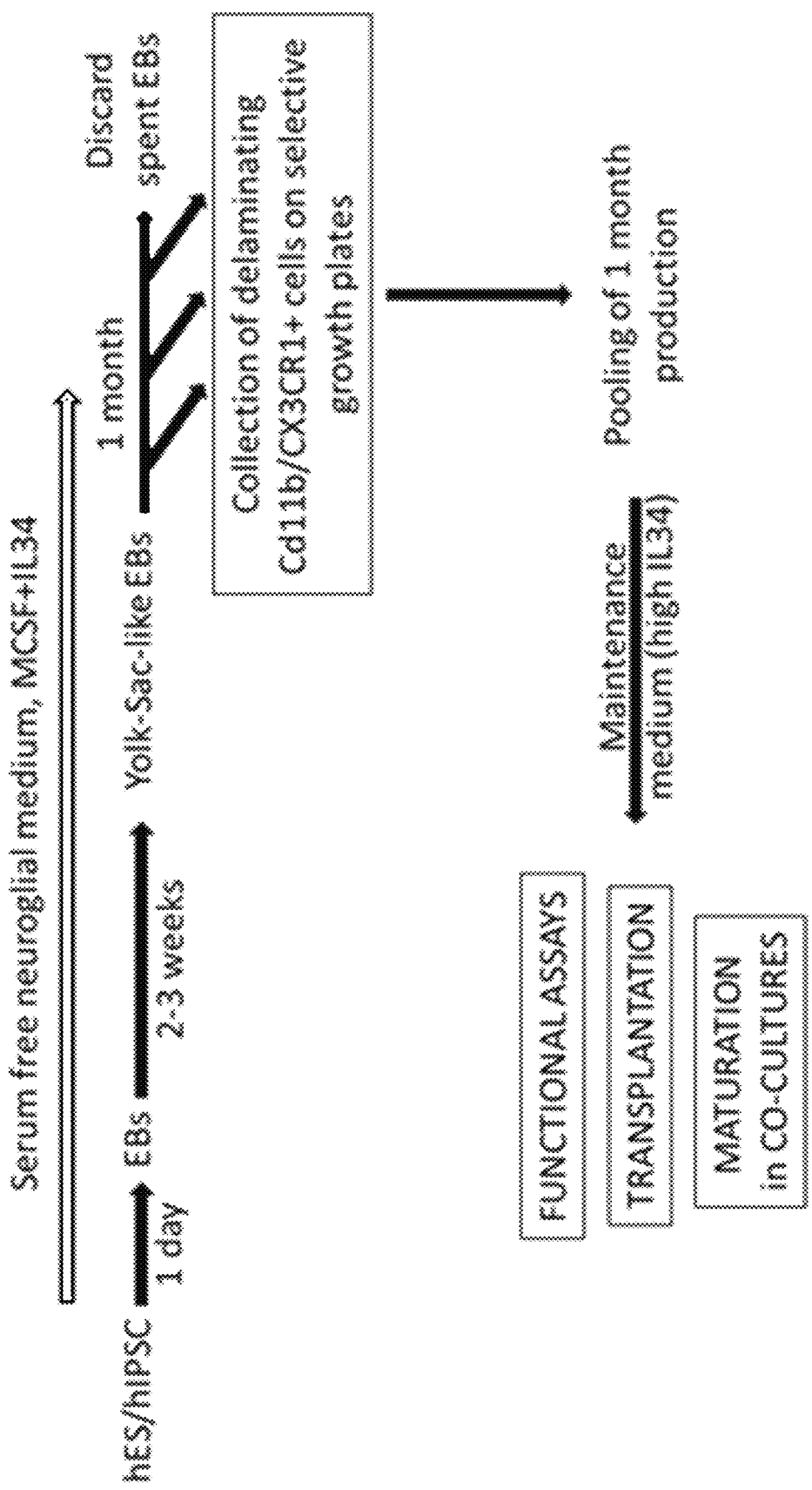
FIG. 4 shows a schematic of the timeline of an exemplary differentiation protocol, over about two months. 2 million embryonic stem (ES) or induced pluripotent stem (iPS) cells can give rise to 1 million microglia-like cells. The embryoid body (EB) stage in suspension is scalable in spinning flasks. The first delaminating cells may correspond to A1/A2 populations, while the EBs may contain the erythromyeloid progenitor (EMP) equivalents.
Figure 5A:
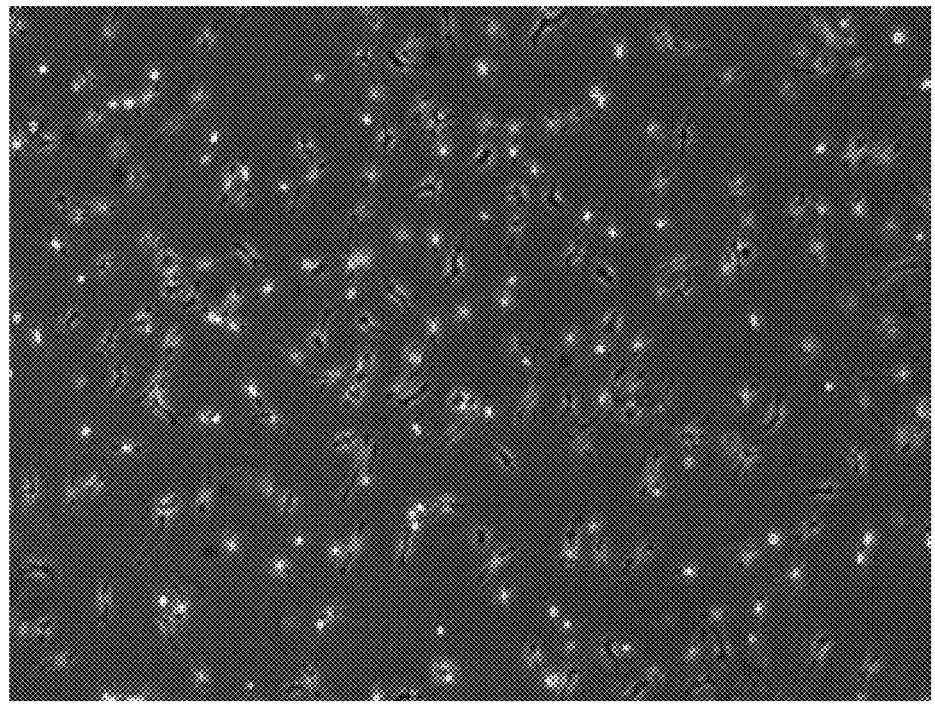
FIG. 5A is an image that shows that culture in high IL-34 medium leads to more ramified morphology.
Figure 5B:
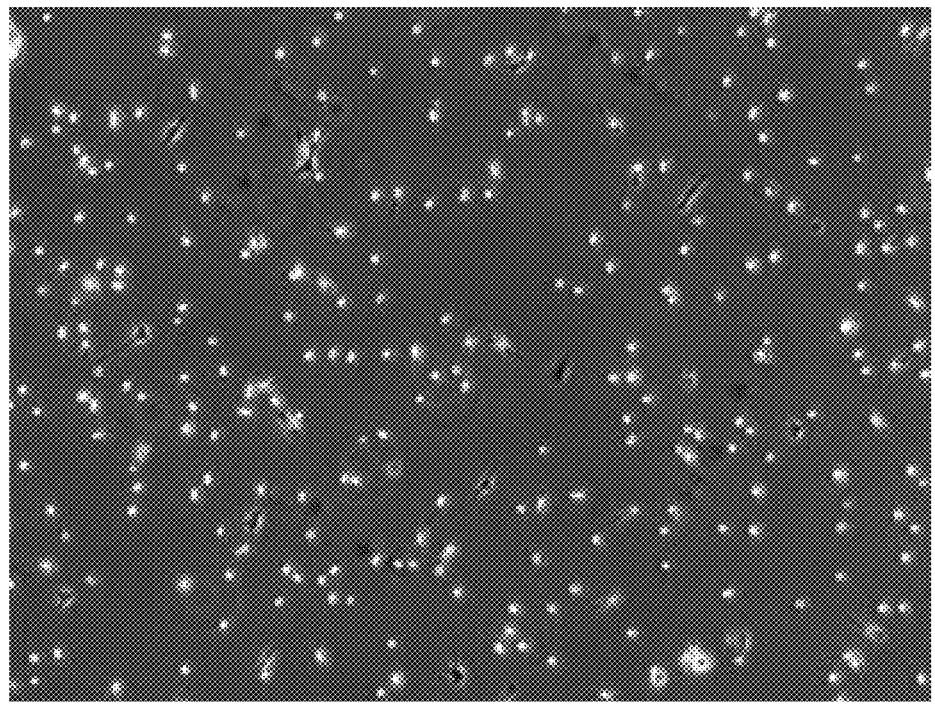
FIG. 5B is an image that shows culture with MCSF, or LPS, trigger rounding up/amoeboid morphology.

Upon passaging, morphology will usually change to amoeboid. Leaving the cells in the medium without disturbance for a few days allows them to adopt a more ramified morphology (FIG. 3).

Maintenance of the slowly dividing population should be done in microglia maturation medium (MM), which consists of NBdiff+100 ng/mL IL34+5 ng/mL MCSF. For studies of activation status, a baseline without MCSF is desirable, and increases the "resting" phenotype of these cells. Removal of IL34 altogether compromises cell viability.

Addition of TGFb1 in concentration ranging from 5 to 100 ng/mL may be used to modulate activation status. The same is true for fractalkine (CX3CL1), and the antibiotic minocycline.

Conditioned medium from astrocytes or neural progenitor cells can be used to mimic the in vivo surroundings and enhance microglial identity. Direct co-culture is also possible, and forms the basis for assays of function in non-cell-autonomous interactions.

These microglia-like cells are extremely sensitive to contamination, simple cell debris, and media changes. Once triggered, activation can wipe out an entire well overnight.

The differentiation should be rapid (one month in general), and produce about 1×10^6 microglia-like cells per initial 1×10^6 million hES or hIPS cells. Scaling must be done at the onset, as the proliferation potential of these cells is low, as expected for microglial cells. In agreement with their in vivo counterpart, a monocytic colony forming cell of origin was not isolated. These cells appear to be straight differentiated from the pluripotent state in a neuralized setting, after formation of a yolk sac structure which may contain bona fide EMPs (erythromyeloid progenitors). The protocol only requires exposure to IL34 and low MCSF, without a need for any of the factors routinely used for hematopoietic differentiation. Of note, the medium composition allows for survival of these cells for several months with care, reflecting the long life and slow turnover of microglia in vivo.

Functional characterizations can be performed on these cells to screen for patient-specific characteristics (diagnostic power) or to monitor the effects of pharmacological or genetic treatments (screening tool). These functional assays include, but are not limited to, motility assays (speed, range of motion), phagocytosis assays (of fluorescent latex beads, labeled bacteria, or relevant protein aggregates), cytotoxicity (in direct contact with other cell types such as neurons, or separate in compartmentalized cultures), and assessment of secretions (metabolites, cytokines, growth factors, freely or in exosomal packaging).

Example 3: A Basal Medium for the Maintenance of Human and Murine Fetal Microglia Serum-based media have been the mainstay of microglial isolation techniques over the years but these undefined culture conditions may unpredictably alter their characteristics. The serum-free formulation described in Table 1 comprises adjusted component concentrations to match those of human cerebrospinal fluid, providing all metabolic substrates necessary for individual cell types growing in the absence of others. Ionic concentrations were chosen to match human cerebrospinal fluid osmolality, thus providing extracellular sodium concentrations necessary for proper electrophysiological function. Iron salts were excluded, instead using iron loaded transferrin in Neurobasal, in order to avoid dangerous redox cycling through Fenton chemistry. Glutamate was omitted to avoid the excitotoxicity of this amino-acid in dissociated cultures. Additional pyruvate and lactic acid were included as energy-providing and neuro-protective substrates in addition to the more canonical oxidative substrates (glucose, galactose and glutamine/glutamax). Biotin and lipid-loaded albumin (Albumax I) were added to support de novo synthesis lipid bilayers (e.g. axons, myelin sheaths). Experiments in examples 3, 4, 5, 6, 7, and 8 were performed using this base, referred herein as NGD (Neuro-Glial Differentiation). NGD constitutes a single defined serum-free medium allowing culture of multiple neural and glial cell types, as well as other cells of interest. Neural differentiation can be initiated in NGD by addition of a small molecule inhibitor of TGFβ signaling (dorsomorphin). Neural progenitor cells can be expanded by addition of FGF2 to the NGD base and differentiation into neurons and glia can be subsequently triggered by FGF2 removal.

Figure 12:
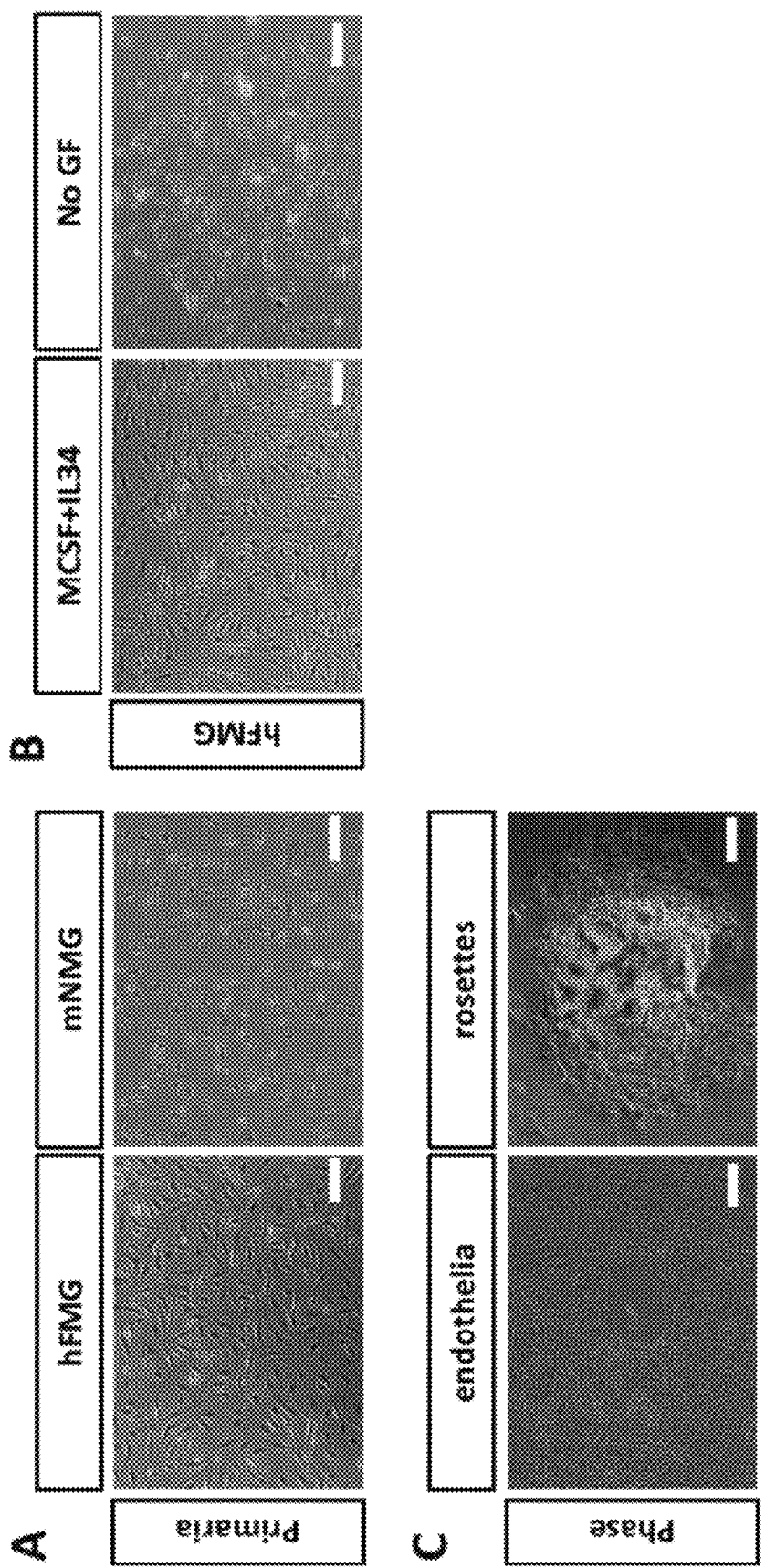
FIG. 12 shows primary human and mouse microglia growth conditions.

To culture selectively microglia, at the exclusion of other cell types, commercially available modified polystyrene (Primaria) plates were used to allow adherent maintenance of mouse neonatal microglia and human fetal microglia (respectively mNMG and hFMG), while maintaining the possibility of enzymatic passaging (FIG. 12A). In contrast, neuroglial derivatives from NPCs are poorly adherent, and thus selected against on this substrate (not shown). IL-34 and CSF1 have been shown to be important for microglia differentiation and maintenance in vivo and were added to the medium. As shown in FIG. 12A, 12B, both hFMGs and mNMGs died in the absence of any CSF1R agonist, with hFMGs adopting a more ramified morphology in the presence of high concentrations of IL-34. Primary cells could be maintained in this medium for more than a month without passaging suggesting this formulation may be generally useful for primary myeloid cultures.

Example 4: Induction of Primitive Microglia in Human Pluripotent Cells

Human ES or iPS cells were grown on feeder layers of murine embryonic fibroblasts as previously described. Following enzymatic passaging, uniform cell clusters, free of single cells, were used for initial embryoid body seeding. These clusters were re-suspended directly in NGD without stepwise adaptation, containing 10 ng/mL CSF1 and IL-34 (microglial differentiation medium, MGdM) in Corning ultra-low adherence plates. After one week, the formation of two types of structures were observed: dense neuralized spheroids, alongside embryoid bodies forming cystic structures, bound by a single cell layer (FIG. 6A). When plated at these early stages on poly-D-lysine, the neuralized EBs flattened into typical rosette-forming neuroepithelium, while the small cystic EBs flattened into cell lawns reminiscent of endothelial cells (FIG. 12C). Islands whorls could be seen giving rise to three-dimensional clusters of round cells at their borders, organizing themselves in ropes (FIG. 6B). Proliferation and growth of these structures after attachment is CSF1R-ligand dependent, as they arrested and devolved in absence of the combination of CSF1 and IL-34 (not shown). The cells at the island borders and in the three-dimensional ropes were positive for VE-Cadherin (FIG. 6B, green), for c-kit (FIG. 6B, magenta) and for both CD41 and CD235a (FIG. 6C, respectively green and magenta). All these markers have been identified in the mouse as markers of the first wave of myelogenesis in the yolk sac, before the establishment of circulation in the embryo (<E8.5), and before definitive hematopoiesis. This immuno-histochemical panel is consistent with these cells representing the in vitro counterparts of early hemogenic endothelia. Therefore, the cells in the cystic EBs express several markers of early yolk sac myelopoiesis, and thus referred to them thereafter as Yolk Sac-EBs (YS-EBs). Large domains of the YS-EBs were positive for the master myeloid transcription factor PU.1 (FIG. 6D), which is necessary for microglial differentiation and maintenance and can induce macrophages from fibroblasts.

Figure 7:
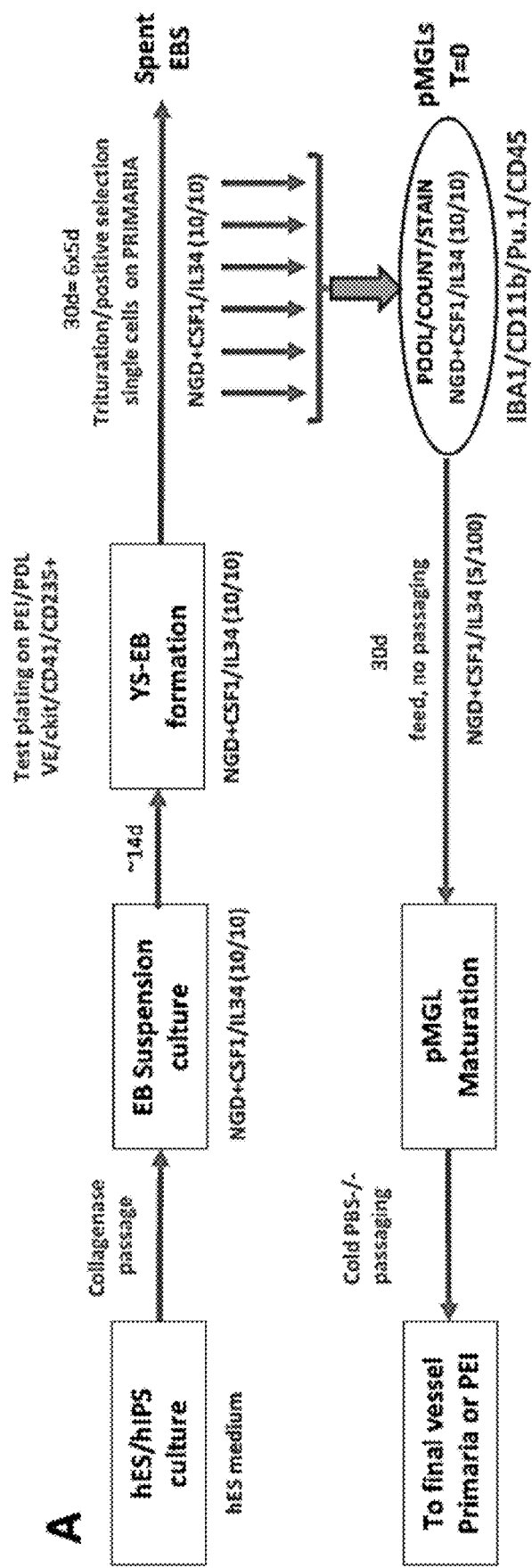
FIG. 7 shows characterization of phagocytes delaminating from cystic YS-EBs.
Figure 7:
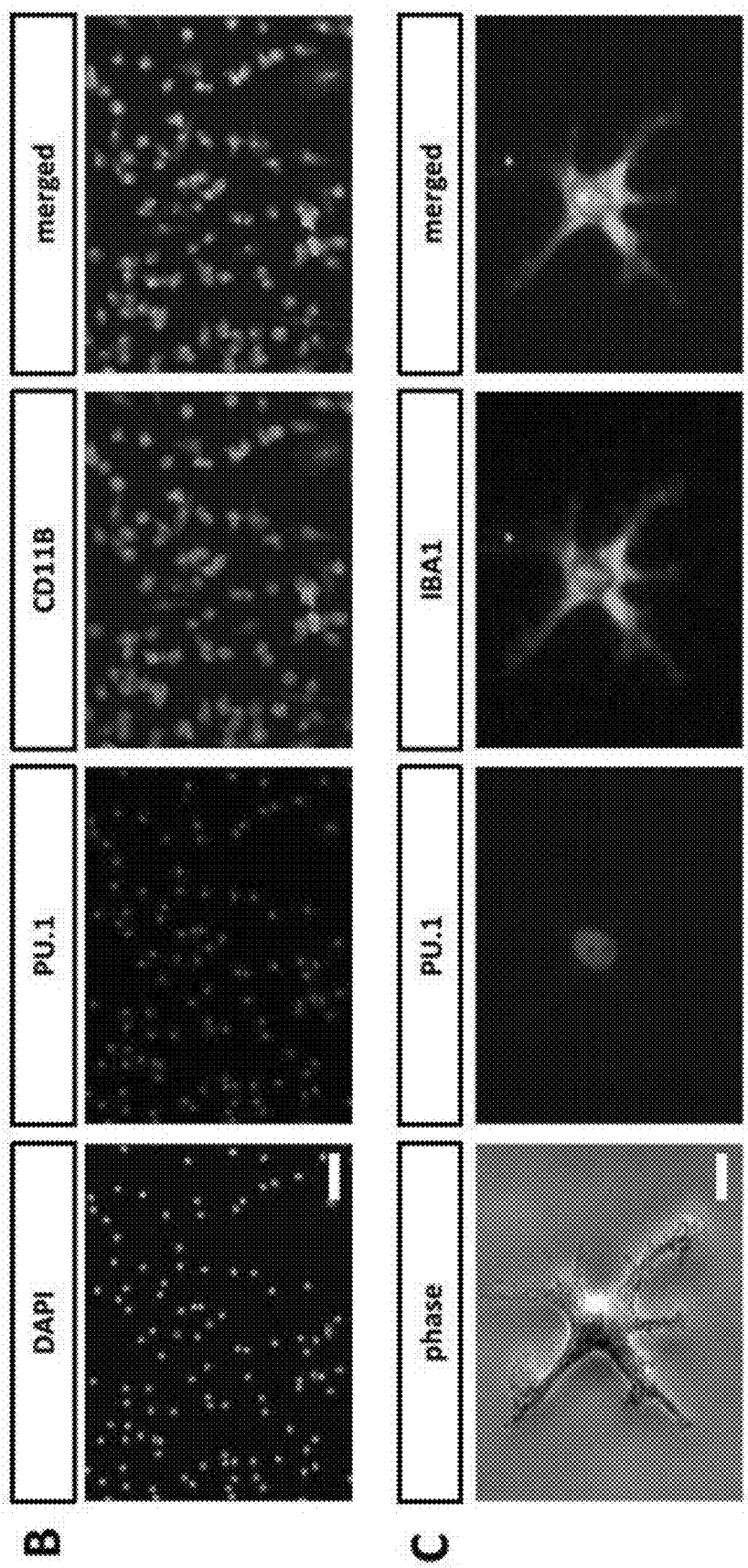
Figure 7:
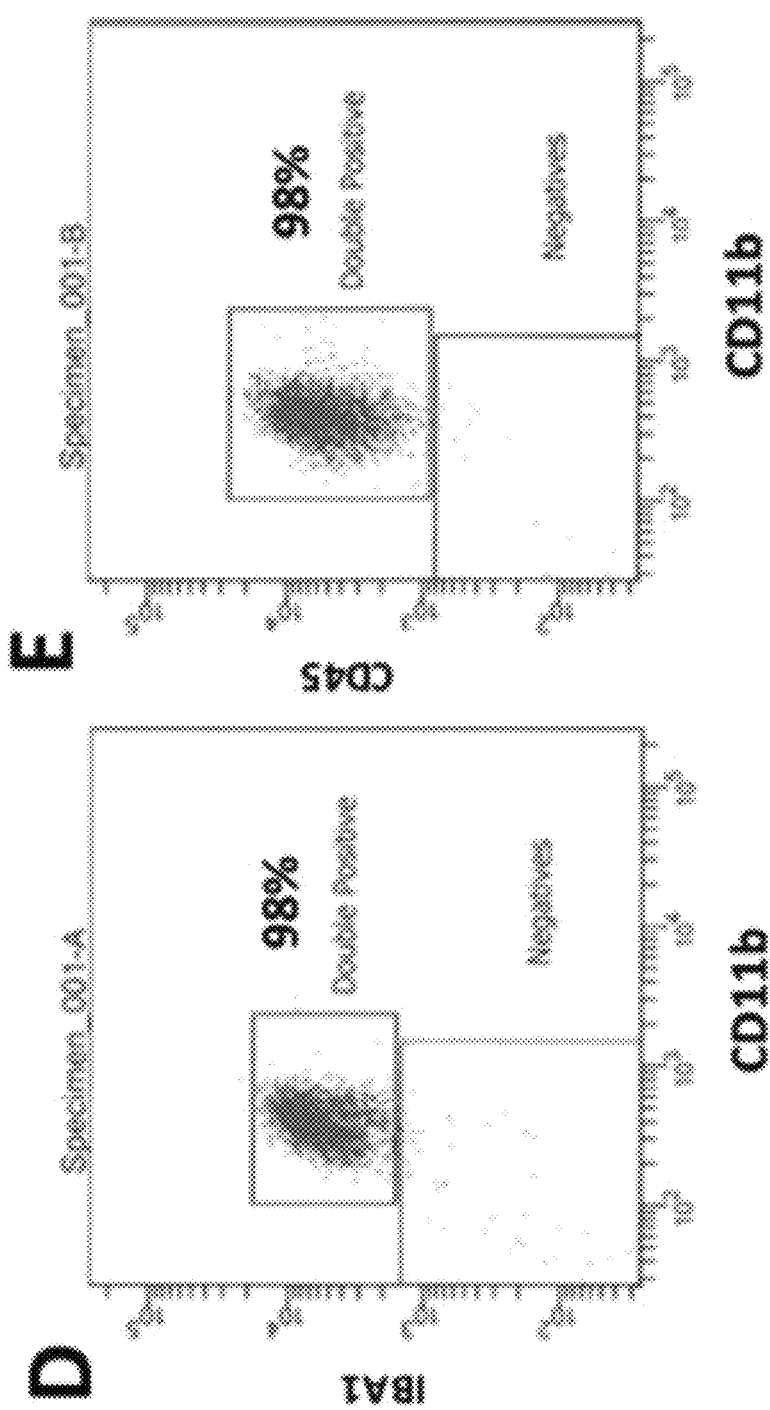
Figure 7:
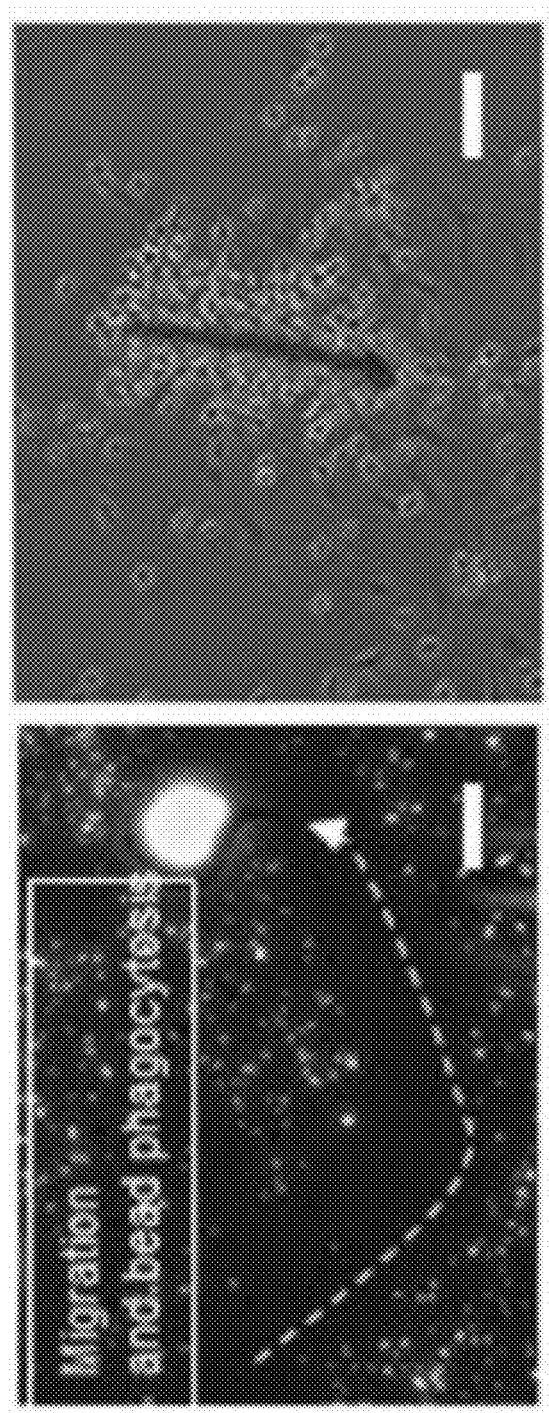
Figure 7:
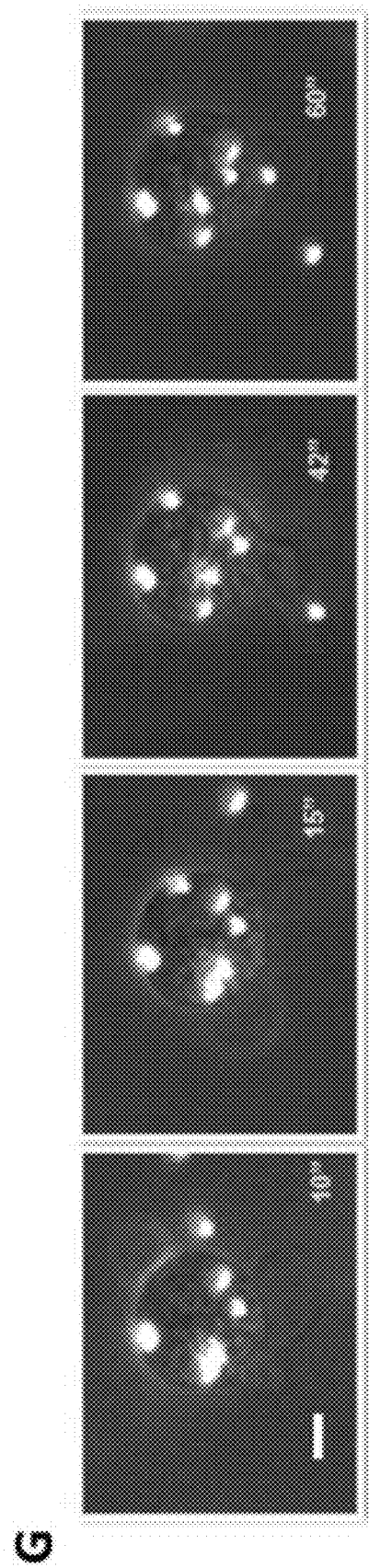

When observed in phase-contrast microscopy, clusters of cells were seen to delaminate towards the lumen of the cysts (FIG. 6E) as well as directly into the outer medium or on the plastic culture surface. When harvested and plated separately on Primaria, the cells that attach to the surface are vacuolated, round and motile cells (FIG. 7). They are positive for PU.1, as well as CD11b and IBA1 (AIF1) (FIG. 7B and FIG. 7C). These markers have all been extensively used to label or define microglia in various systems. These cells can be further sorted by FACS and are homogeneously positive for IBA1, CD45 and CD11b (FIG. 7D and FIG. 7E), with the majority of cells, physically selected by the growth conditions, positive for all markers. Further characterization of these immature cells and their progeny, referred to as pluripotent stem cell-derived microglia-like cells (pMGLs), is in FIG. 7A, which summarizes the protocol and the timeline to generate pMGLs from human ES and iPS cells. Removal of either IL-34 or CSF1 from pMGLs culture rapidly leads to cell death (not shown). EDU incorporation is seen in 60% of nuclei from early pMGLs (2 weeks from onset of production). After 2 months in culture, EdU incorporation shows that less than 5% of pMGLs kept in MGdM are mitotic within a 24-hour period (FIG. 7B). Importantly, both primary fetal microglia and pMGLs can be maintained for several months in culture despite ultimately limited renewal potential, demonstrating their longevity. The immature pMGLs initially delaminating from YS-EBs are round yet already highly phagocytic, as observed by the uptake of fluorescent latex beads (FIG. 7F, FIG. 7G) and extend filopodia and membrane ruffles, allowing the capture of nearby corpuscles, such as inert plastic beads. The cells are highly motile and will readily tax to and encapsulate foreign bodies such as fibers present in the well (FIG. 7F) as expected of professional phagocytes such as microglia.

To assess the reproducibility of the differentiation protocol, microglia were induced from 20 different ES and iPS cell lines representing a panel of normal and disease genotypes. Table 2 demonstrates successful induction of microglia-like cells from all cell lines with time and quality of the microglia varying between the different donor cells. As described earlier, the cells generated through this protocol are homogeneously positive for the canonical markers used in microglial isolation techniques. Table 2 reports quantitative output at an early cutoff of 4 weeks, matching the cutoff for NPCs. The cumulative yields are significantly higher. For example, after 8 weeks of differentiation, hES-wibr1, iPS-wt1, iPS-wt4, iPS-ALD4 and iPS-ALD1 respectively generated $1\times10^6$, $1\times10^6$, $3\times10^6$, $2\times10^6$, and $8\times10^6$ microglia-like cells, from $2\times10^6$ pluripotent stem cells at the onset. Therefore, the differentiation protocol is efficient and robust, though the genetic background of the pluripotent donor affects the kinetics and yield of the microglia-like cells.

Example 5: Phenotypic and Functional Characterization of pMGLs

Figure 8:
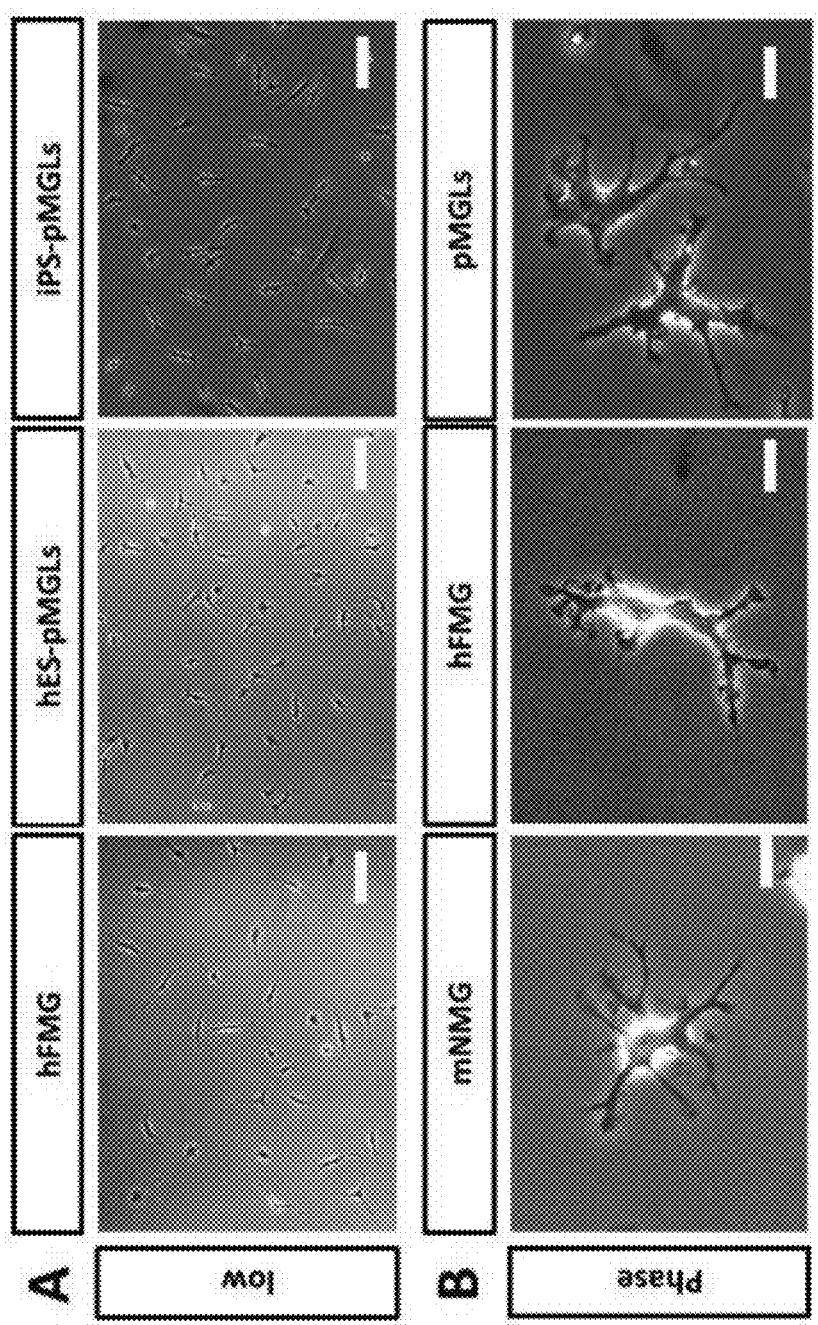
FIG. 8 shows pMGLs adopt ramified morphologies over time and express specific markers of microglia.
Figure 8:
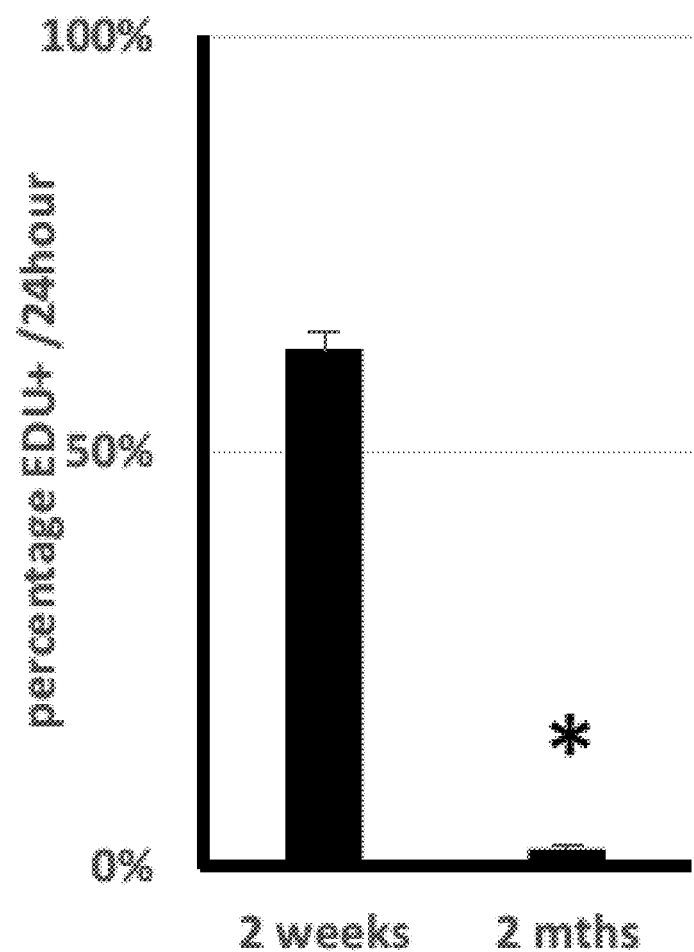
Figure 8:
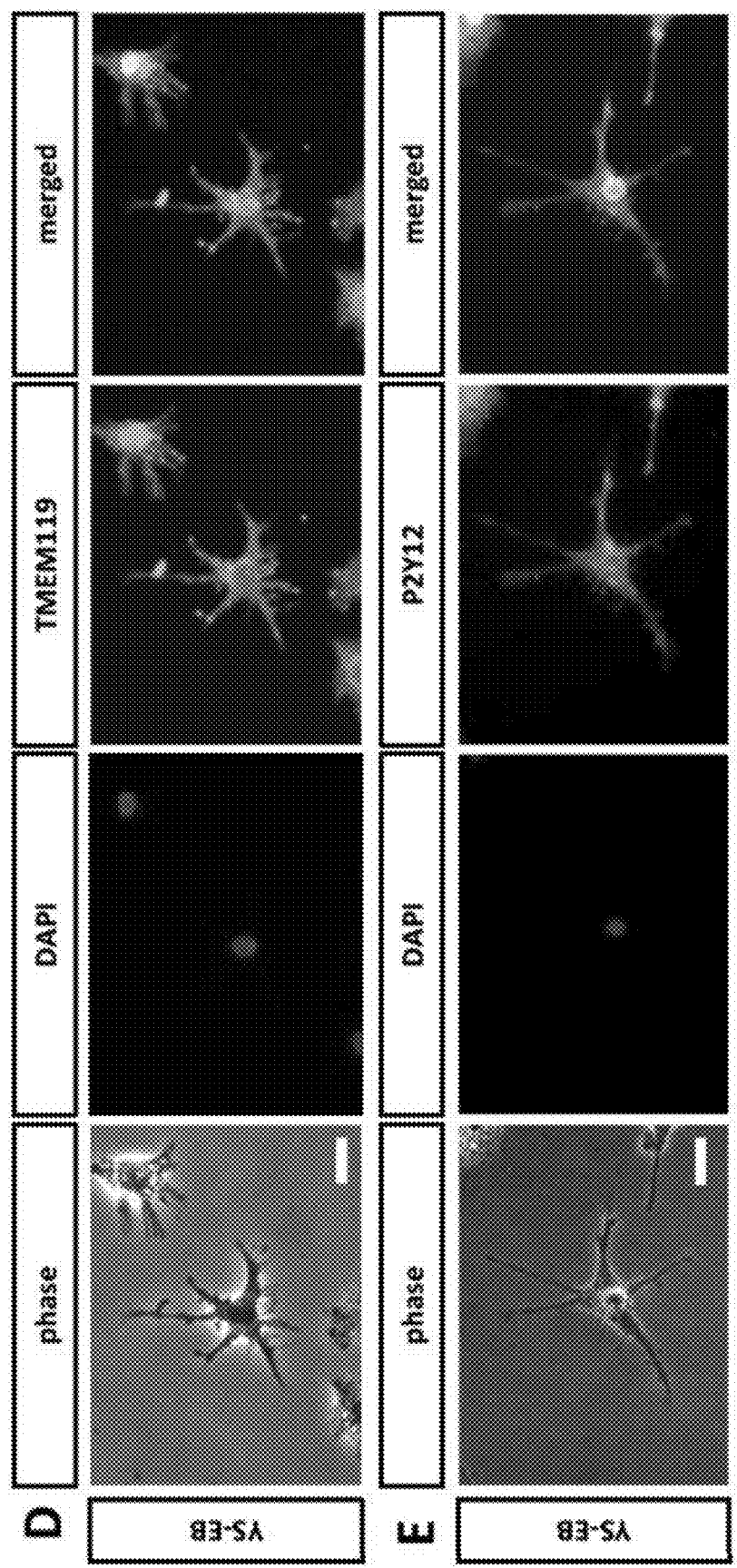
Figure 8:
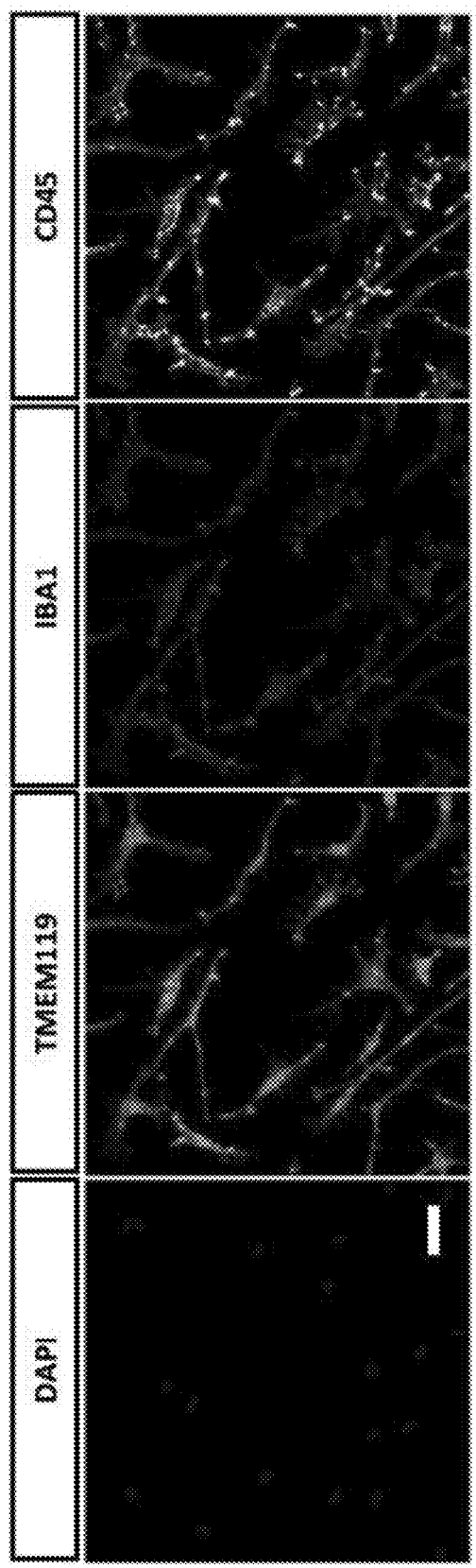

In culture, monocyte-derived macrophages adopt either a "fried-egg" morphology, or an axial bipolar spread reflecting the macrophage polarization and activation status. In contrast, a typical characteristic of microglia is to become highly ramified in vivo. To assess the phenotypic characteristics of the cells, pMGLs were cultured in a maintenance medium containing high concentrations of IL-34 (100 ng/mL) and low concentration of CSF1 (5 ng/mL), in NGD base. As shown in FIG. 8A, primary human FMGs and pMGLs derived from hES or hiPS cells adopted an identical morphology, characterized by multiple thin first-order branching terminated by actively motile membrane ruffles, around an immobile soma.

To assess whether the pMGLs were positive for proteins characteristic of microglia, the cells were stained for TMEM119 and P2RY12, two markers known to be expressed in murine and human microglia. FIG. 8C and FIG. 8D show that pMGLs were positive for both TMEM119 and P2RY12, displaying a broad membrane and punctate vesicular expression pattern, which is consistent with their roles as part of the microglial sensome. Importantly, an overwhelming majority of cells plated at this stage are positive for TMEM119 and IBA1, as exemplified in FIG. 8E.

Figure 9:
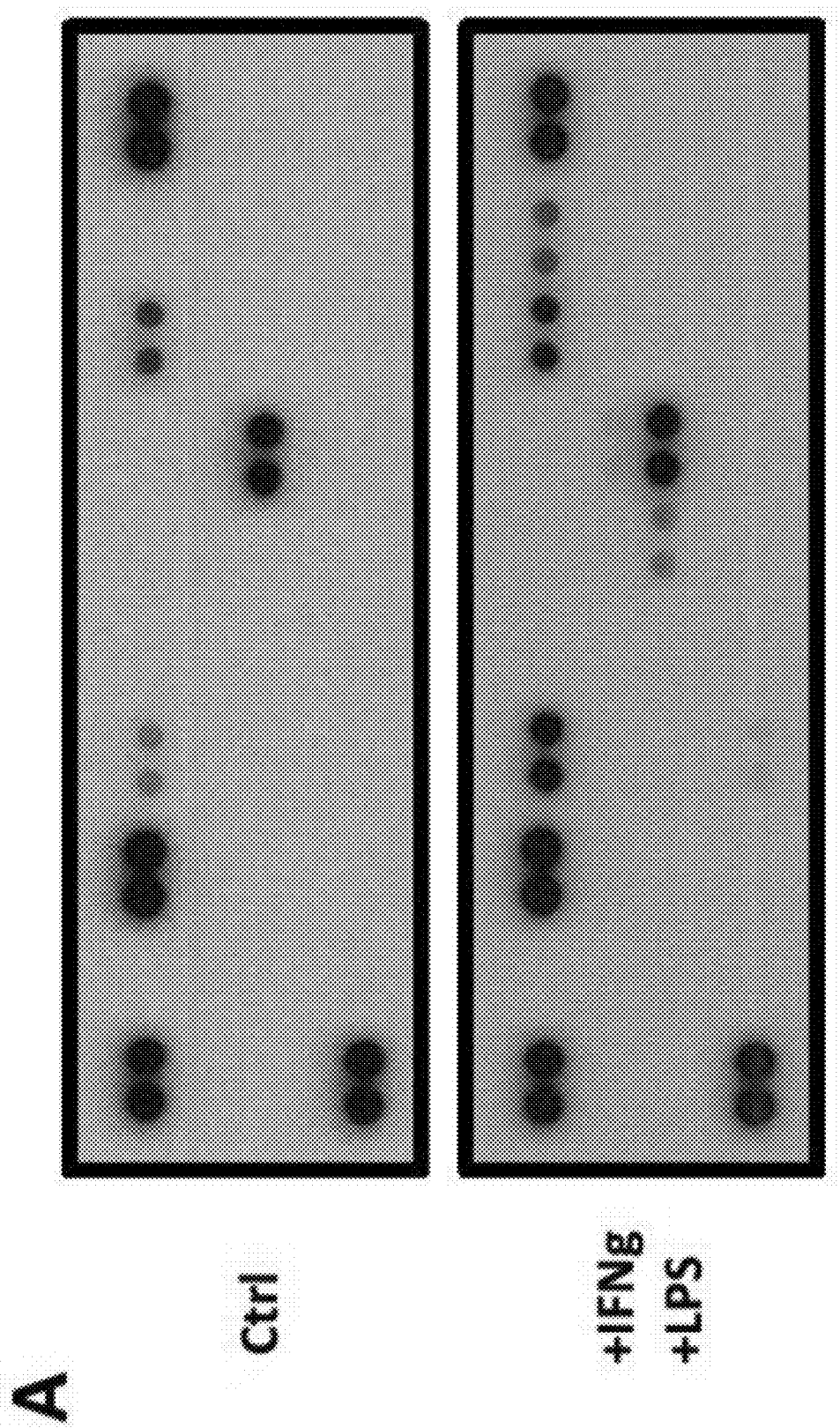
FIG. 9 shows pMGLs can display reactivity to endotoxin challenge, and disease-relevant morphological changes.
Figure 9:
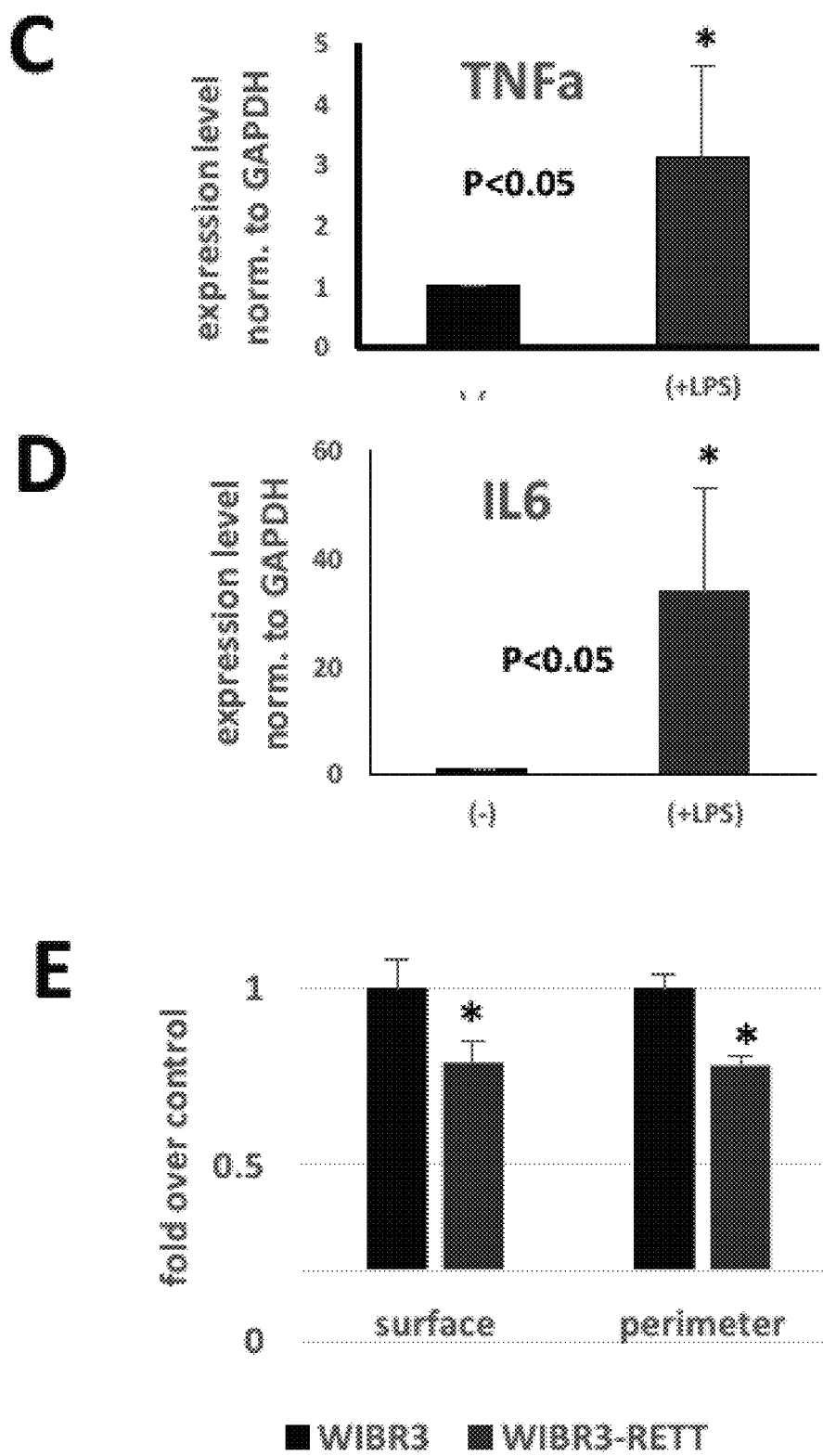

The microglial secretome is a complex set of chemokines and cytokines, which are important for maintenance of tissue steady state, or establishment of an inflammatory reaction. Cytokine and chemokine profiles released in the supernatant of pMGL cultures were assessed. Unstimulated pMGLs secreted detectable levels of various cytokines and chemokines, including IL-8, CXCL1 or CCL2 (FIG. 9A). As innate immune cells, microglia react to a variety of stimuli. For example, the presence of IFNγ and endotoxin (LPS) triggers the release of chemokine and cytokines above baseline (FIGS. 9A-D). In particular, CXCL10, MIP1a, IL-6 and TNFα were increased more than 2-fold within the dynamic range of this assay. This effect was detectable at the transcriptional level, with an increase in mRNA of IL-6 and TNFα (FIG. 9C and FIG. 9D). Other phenotypic changes may be readily observable in the morphological features of microglia. Prior data had previously shown that isogenic MECP2 wild type and mutant human ES-derived neural cells recapitulate features found in patients (such as small neuronal somatic size and lower dendritic complexity), and allowed discovery of novel aspects of Rett syndrome cellular biology. Microglia was missing from these analyses, yet have become in recent year the focus of great interest, following controversial findings that transplanted wild-type phagocytes derived from bone marrow could rescue features of Rett syndrome. pMGLs have the potential to clarify some of the cell autonomous and non cell autonomous aspects of Rett microglial biology. FIG. 9E shows derived pMGLS from isogenic male wild-type and MECP2 mutant cells, and show that mutant cells are significantly smaller than the wild-type cells. This may contribute to one of the phenotypes of Rett syndrome patients (smaller head circumference), and is likely to underlie functional differences in Rett microglia, with therapeutic implications. These results indicate that monocultures of pMGLs can be a substrate to study the functional and morphological changes in microglia, derived from isogenic parental cells, and to screen for modulators of inflammation.

Example 6: pMGLs Resemble Primary Human Microglia, and Differ from Peripheral Macrophages The molecular signature specific of microglia, which is distinct from other macrophages, was used to compare the transcriptome of pMGLs with bona fide primary human microglia. Isolated human fetal microglia and pMGLs were grown in the same maintenance medium for a week (MGM). This comparison is relevant since pMGLs are directly isolated from differentiating pluripotent stem cell cultures and grown in serum-free neuroglial-compatible conditions. The results demonstrate that pMGLs display a signature strikingly resembling that of fetal human microglia kept in the same conditions. Table 3 shows that the top GO categories coincide between both cell types, and include antigen processing and presentation through WICK ATP and purinergic metabolic processes, phagocytosis and positive regulation of cytokine production. One observation was that pMGLs differ in the enrichment of gene categories related to the establishment and modulation of the extracellular matrix (ECM). Upon looking at the top 200 genes overexpressed in pMGLs compared to primary microglia (Table 4), the ECM binding came up as the most enriched and highly significant molecular functions (Table 5). The differentially expressed genes between primary cells and in vitro derived pMGLs did not include any of the canonical myeloid ontology terms, supporting their use as surrogate for human microglia. Several individual genes were highly expressed in primary human fetal microglia and pMGLs, consistent with their myeloid identity (FIG. 13A). Among those genes were CD11b (ITGAM), ITGB2, CSF1R, CD45, IBA1, ADORA3 or LGMN. In addition, pMGLs highly expressed genes relevant to nervous system disorders such as APOE, CD33 and TREM2 (FIG. 13B). None of those are significantly expressed in neurons. CD33 and TREM2 are exclusive to microglia in the CNS, while APOE is also found in astrocytes, but is not highly expressed in macrophages.

Figure 10:
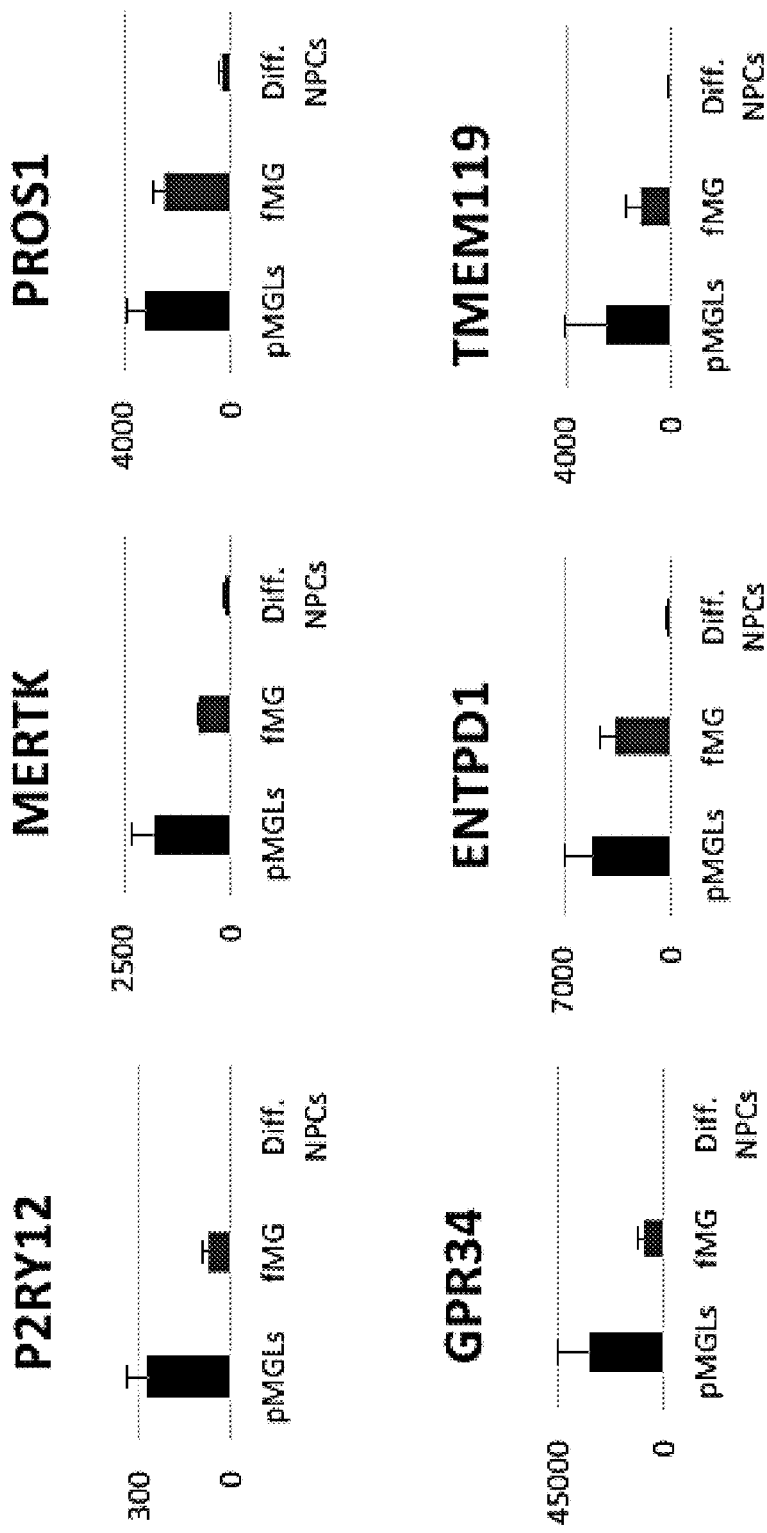
FIG. 10 shows pMGLs recapitulate the consensus signature distinguishing primary microglia from other macrophages.
Figure 10:
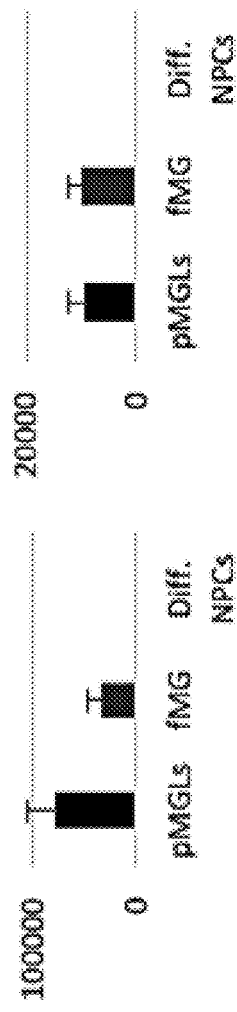
Figure 10:
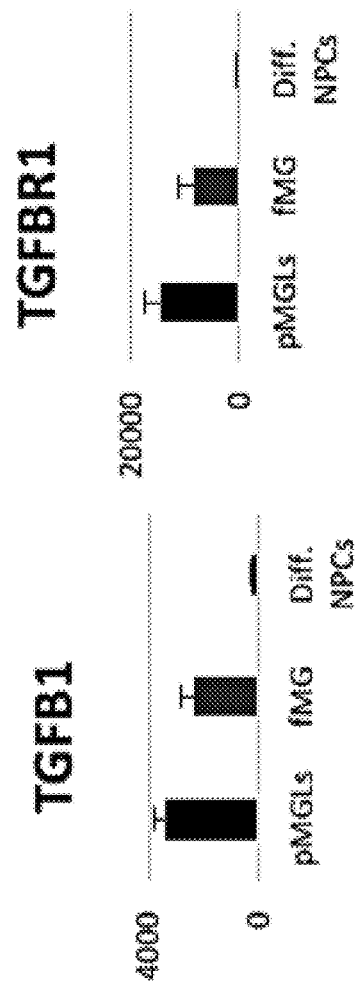
Figure 10:
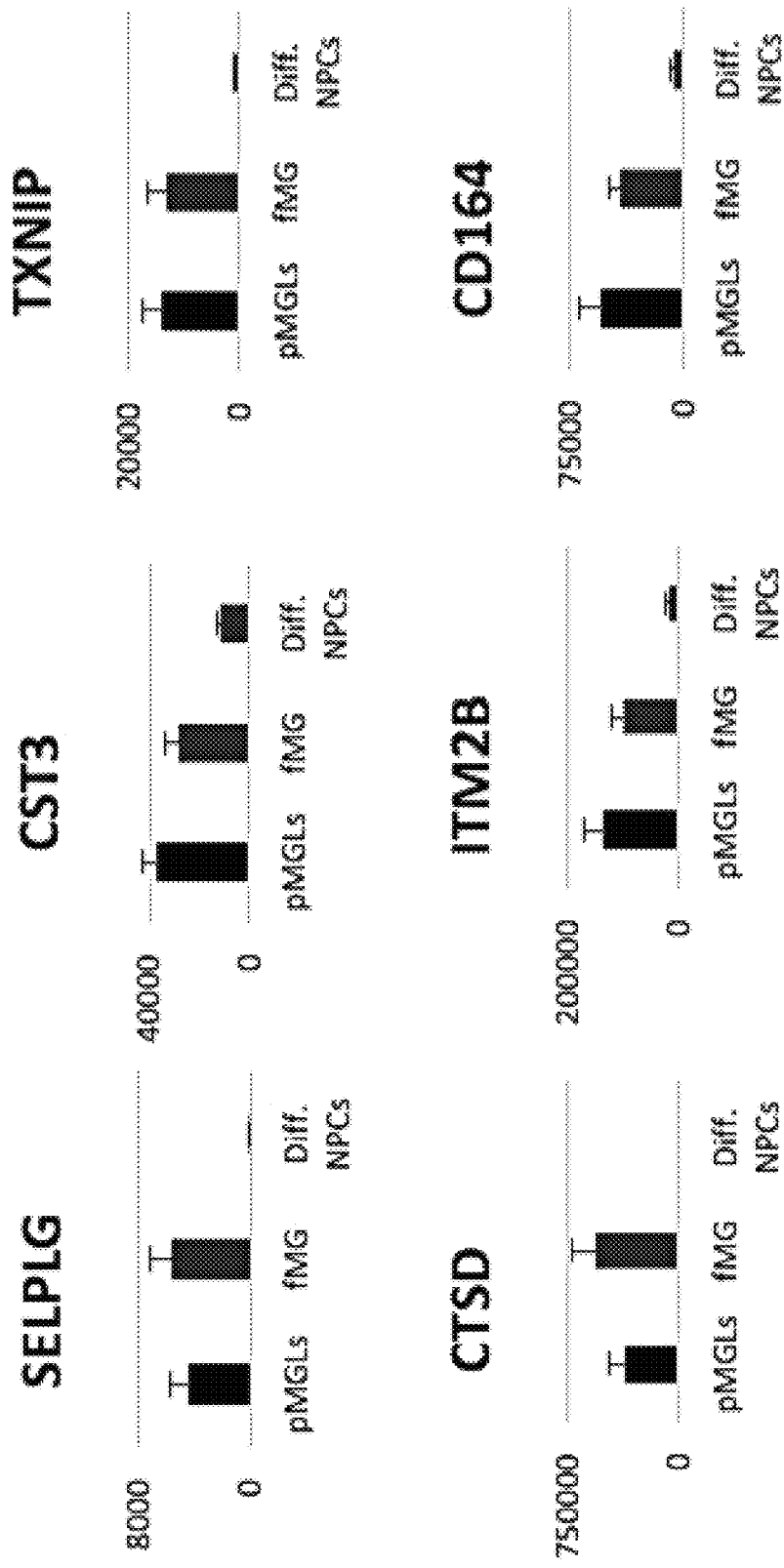
Figure 10:
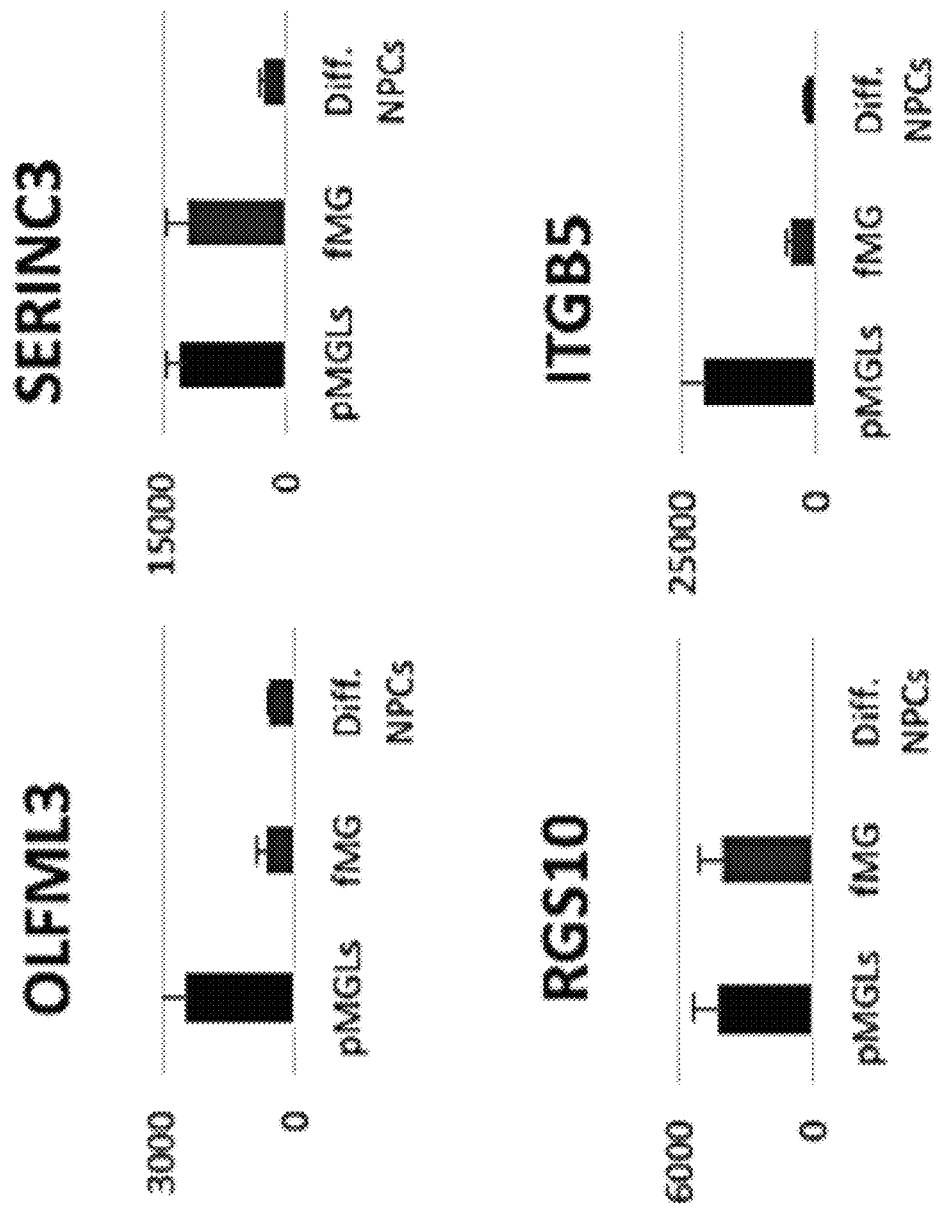
Figure 10:
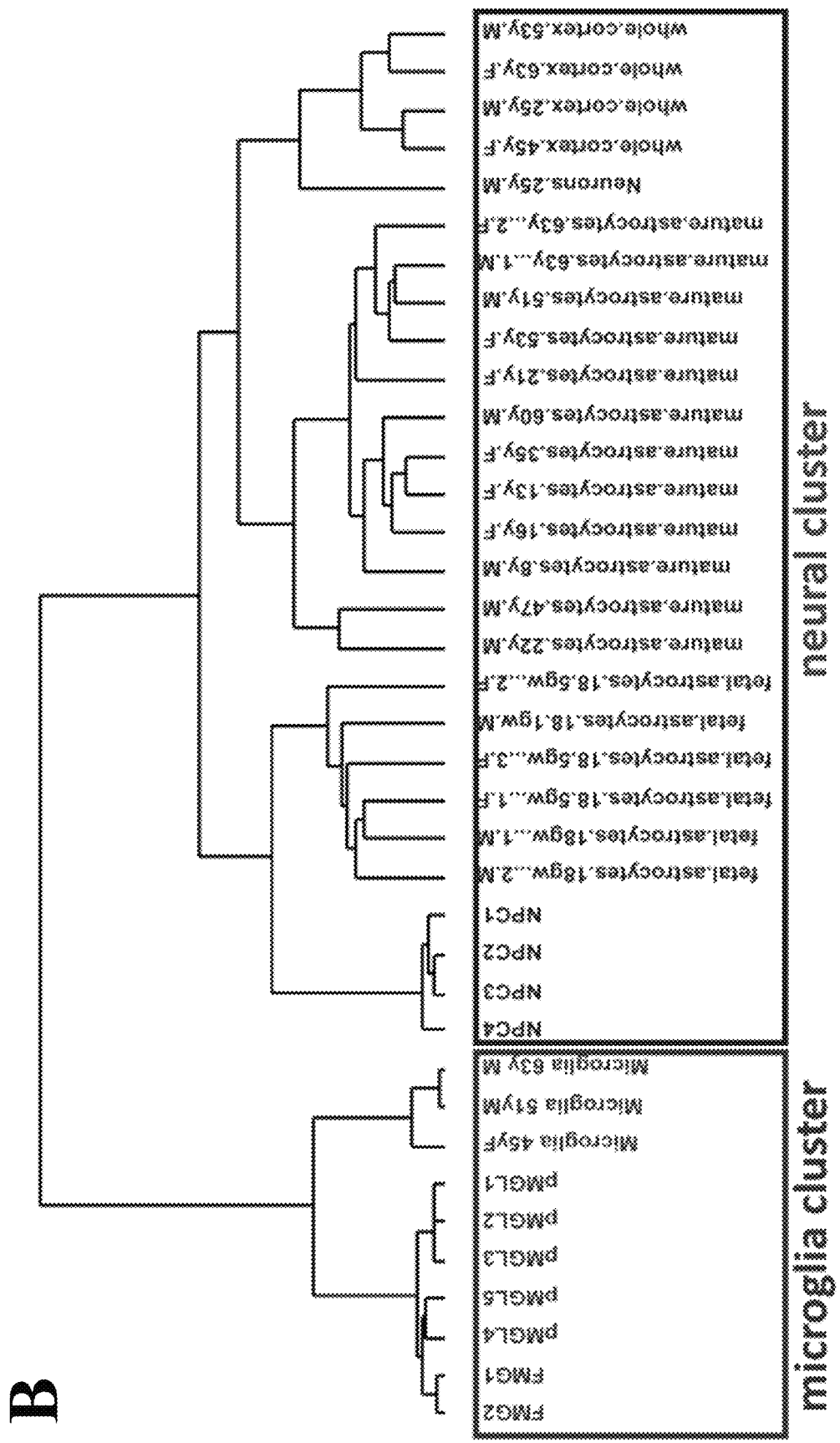
Figure 11:
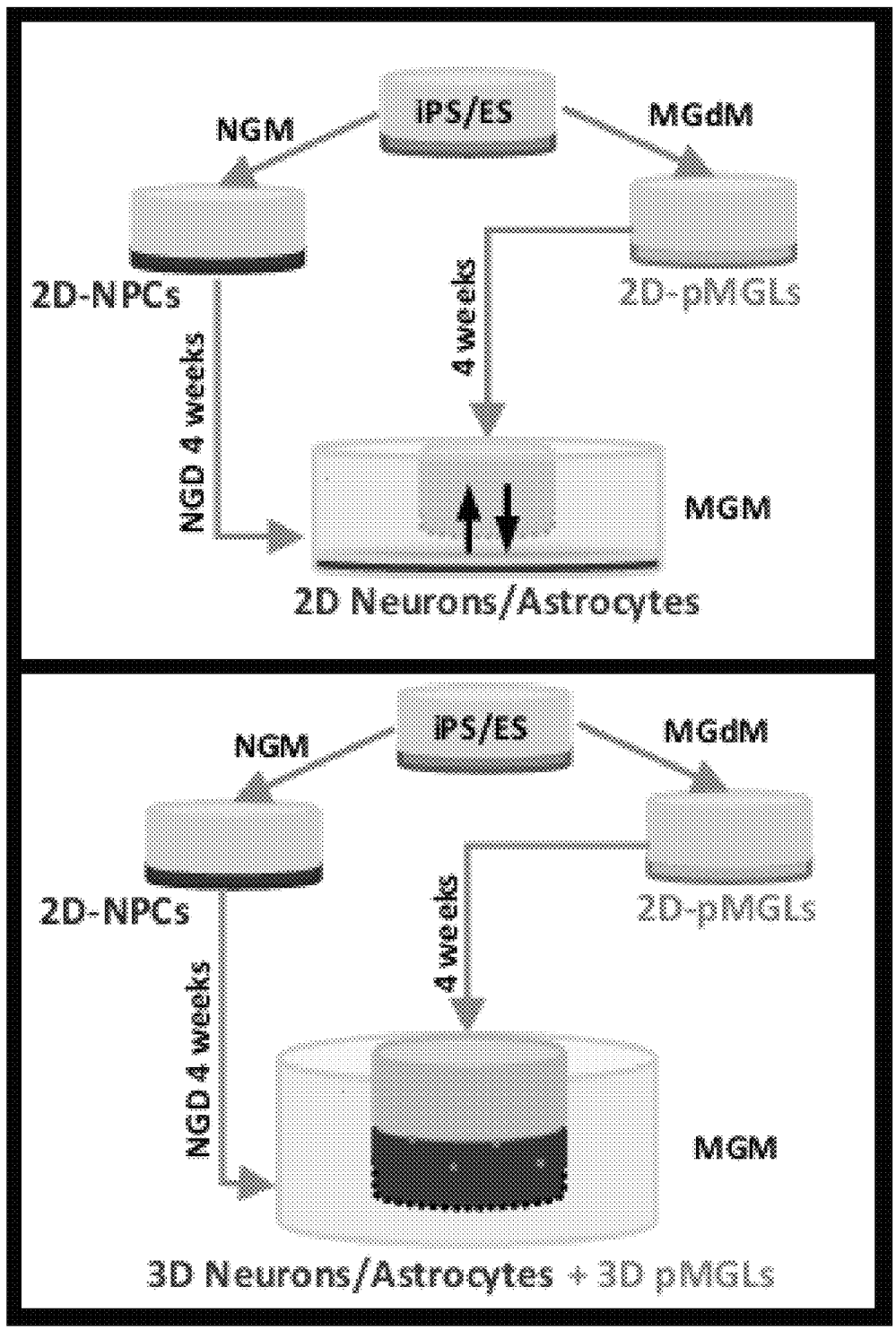
FIG. 11 shows neural co-cultures enhance the microglial signature of pMGLs.
Figure 11:
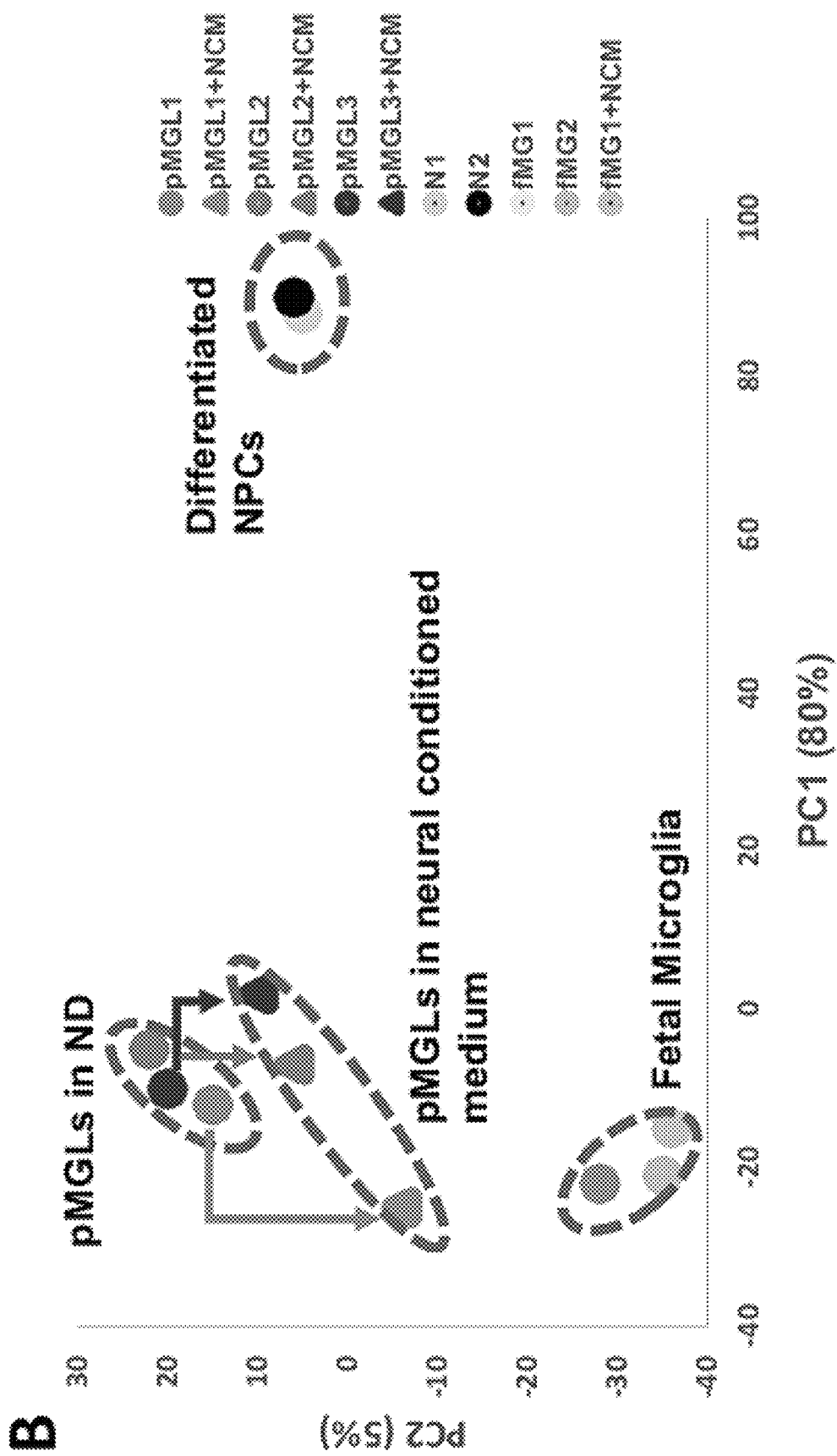
Figure 11:
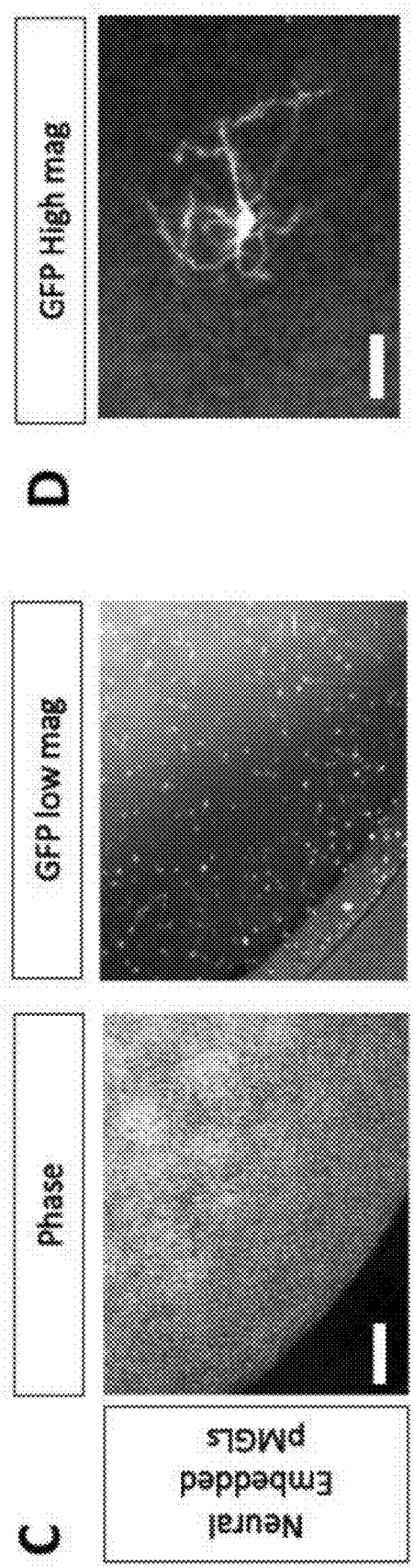
Figure 11:
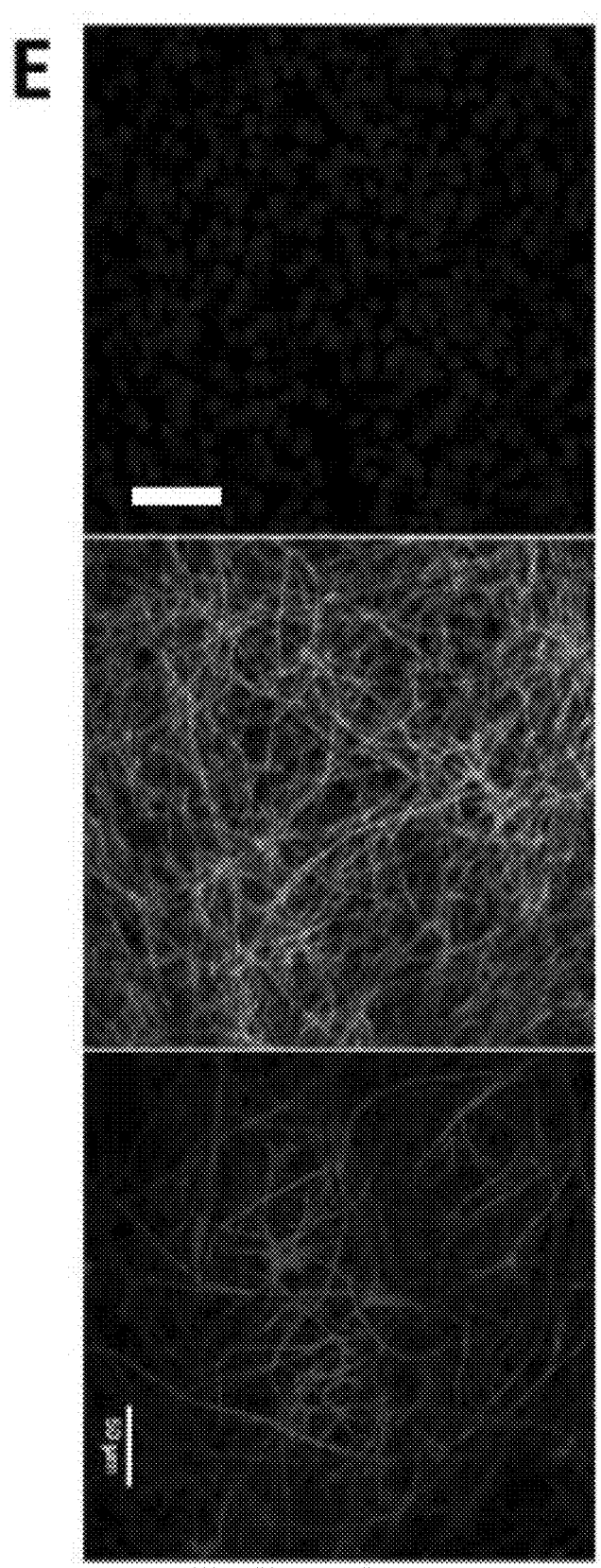
Figure 11:
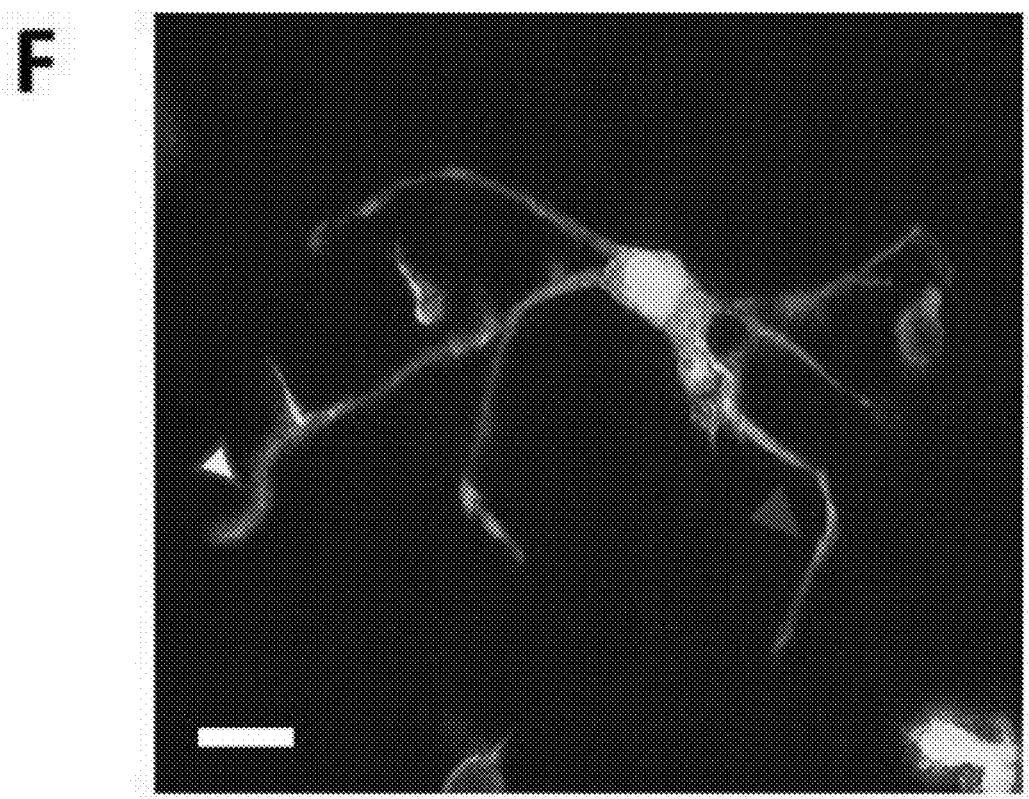
Figure 11:
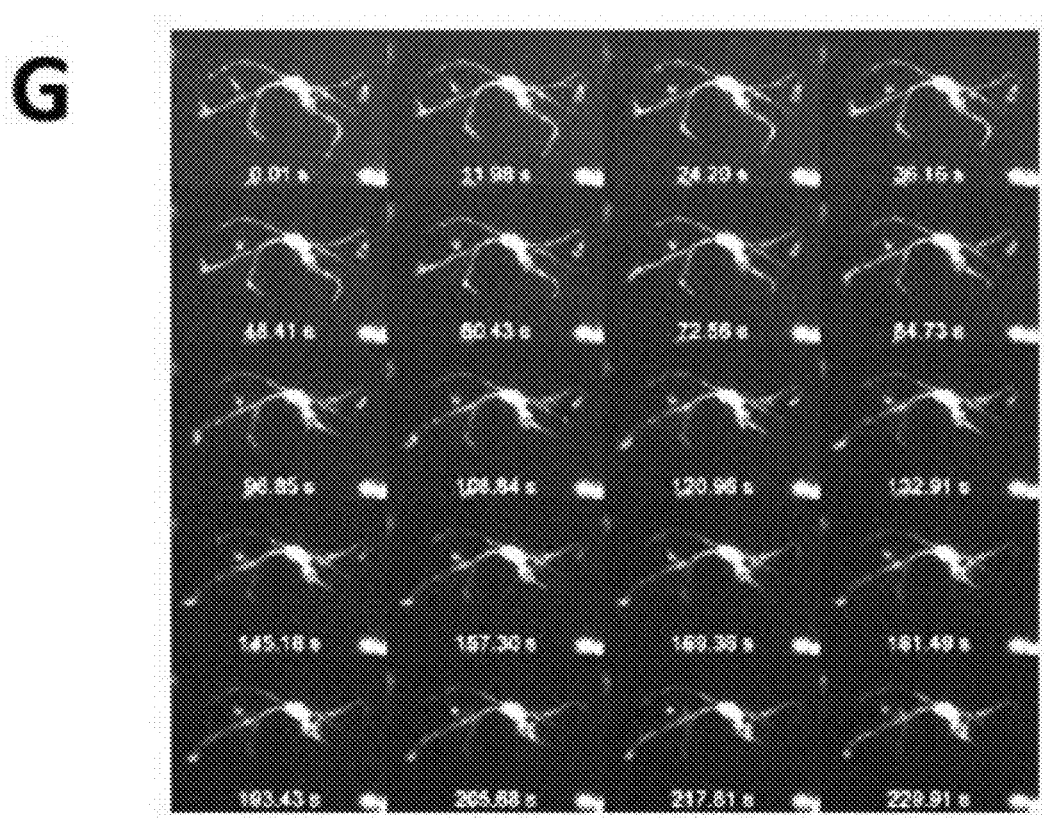
Figure 11:
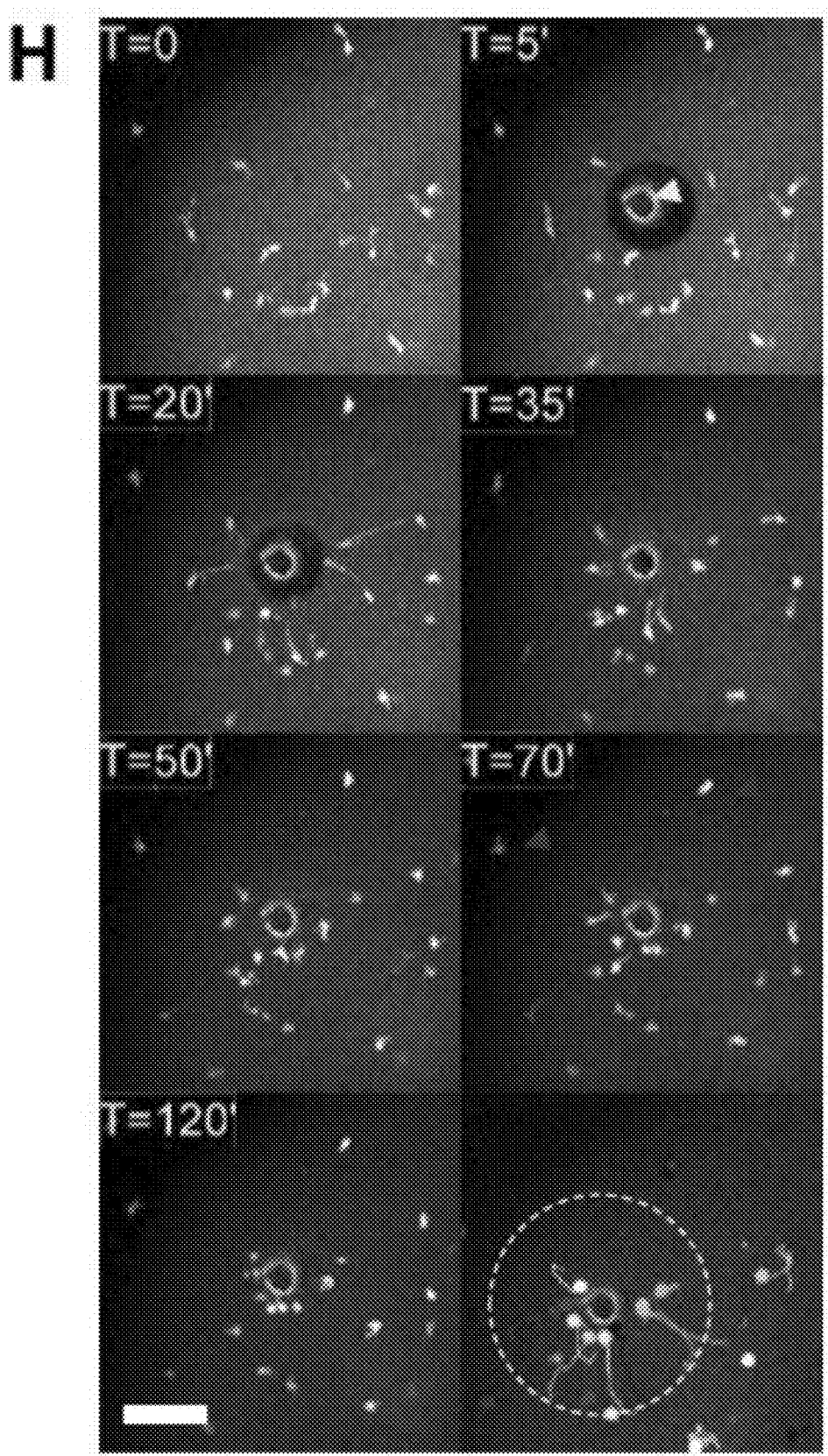
Figure 13:
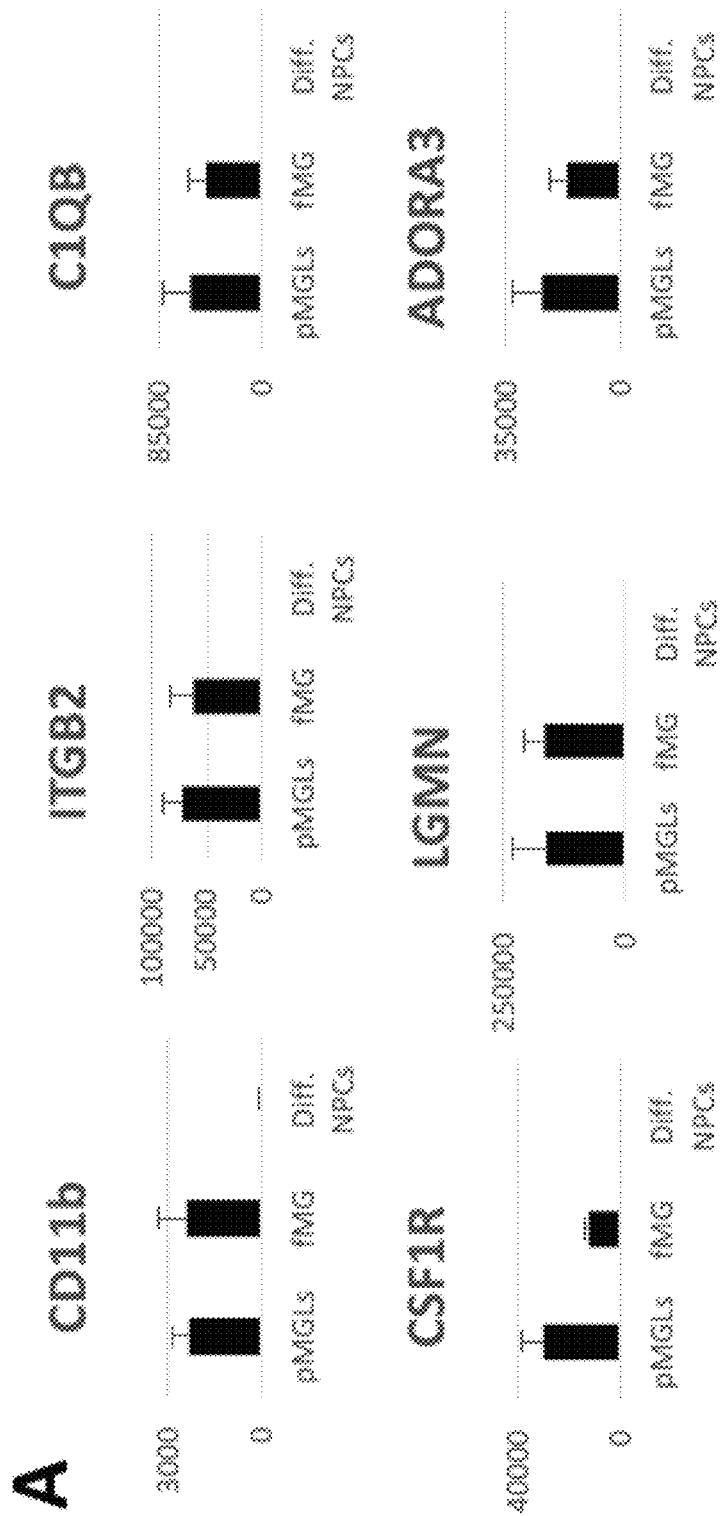
FIG. 13 shows expression levels from RNAseq dataset highlighting a panel of canonical microglial markers.
Figure 13:
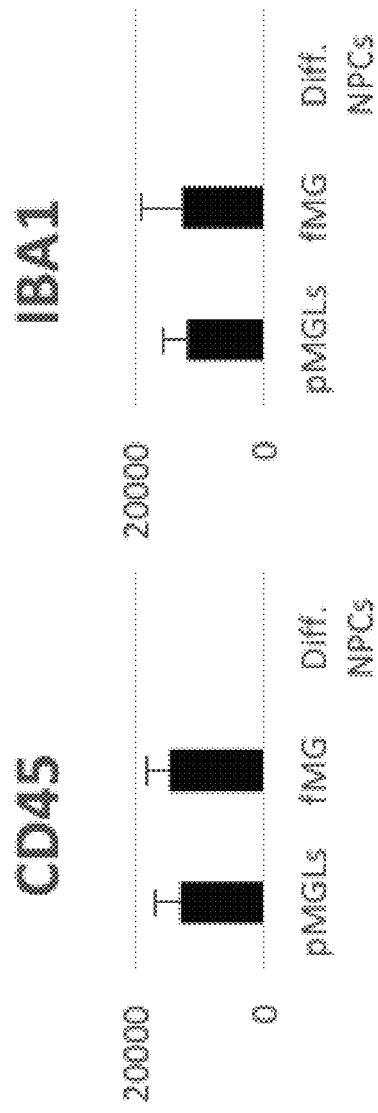
Figure 13:
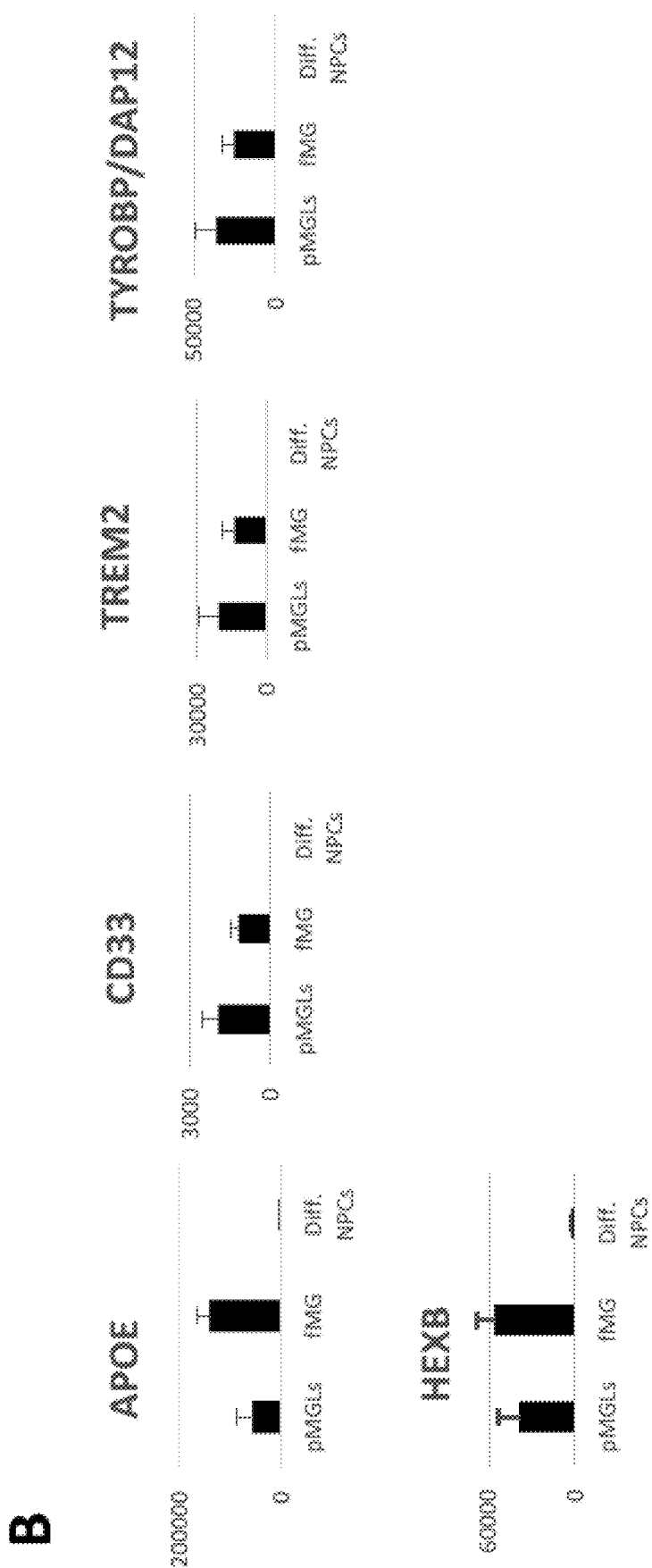
Figure 13:
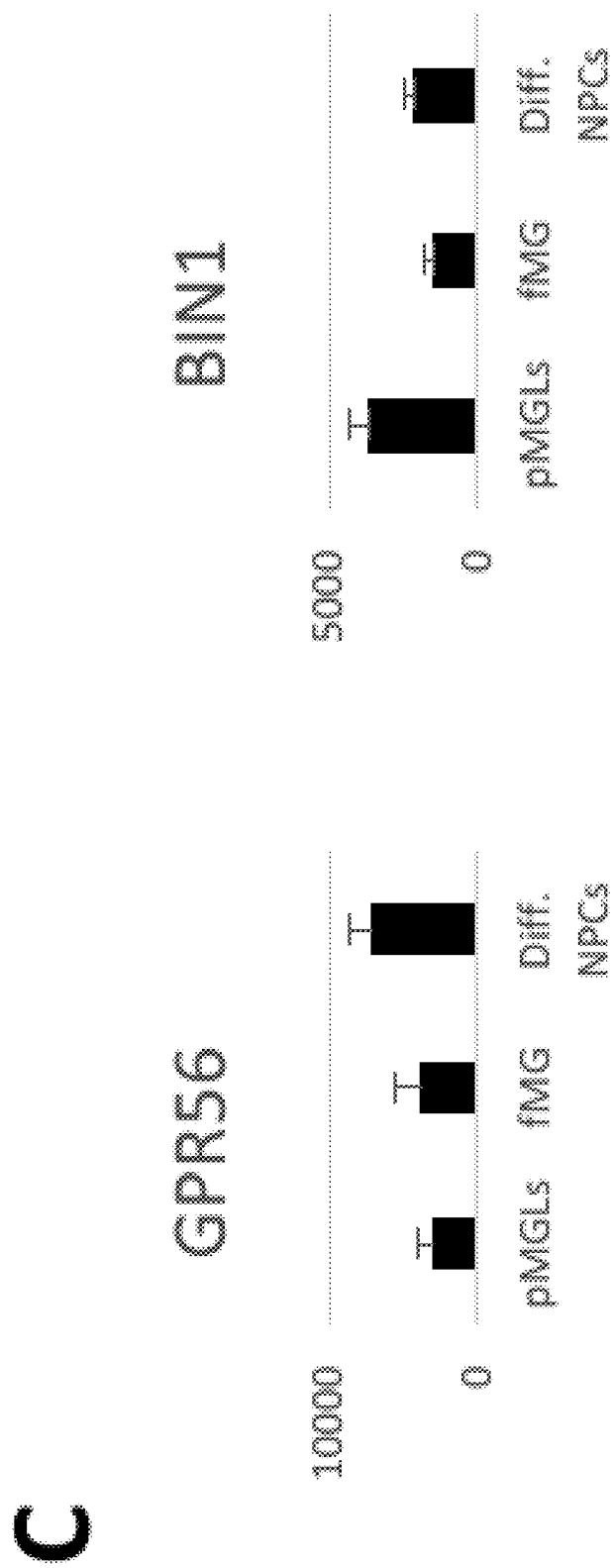
Figure 14:
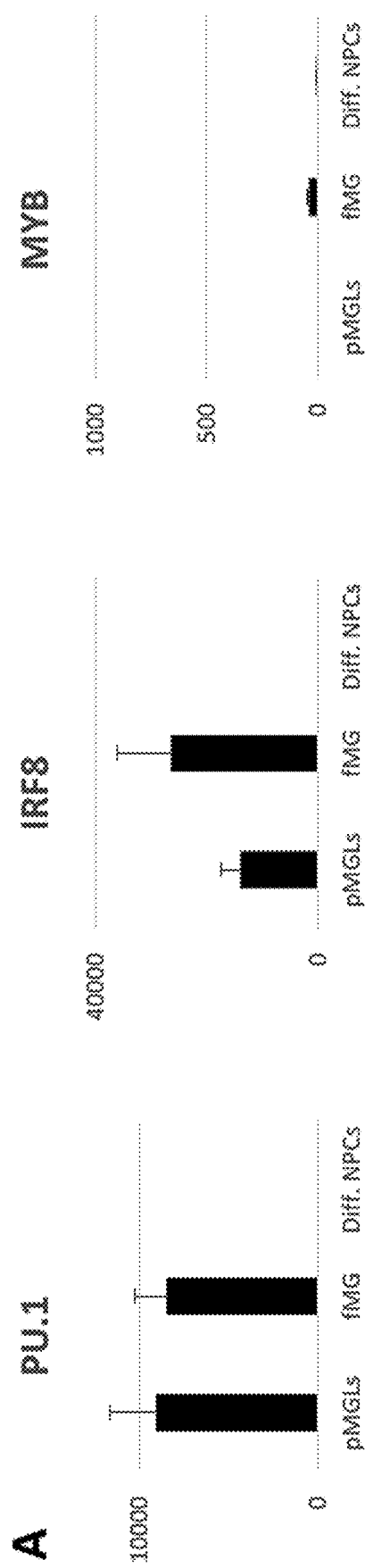
FIG. 14A shows pMGLs and fetal microglia express high levels of PU.1 and IRF8, but little to no MYB, consistent with microglial ontogeny.
FIG. 14B shows unbiased hierarchical clustering against parental iPS cells and primary and induced macrophages (HMDM 523 and IPSDM respectively). This analysis shows that while induced and primary myeloid cells broadly cluster with each other away from iPS cells and NPCs, primary microglia cluster with induced microglia (pMGLs), and macrophages cluster separately.
Figure 14:
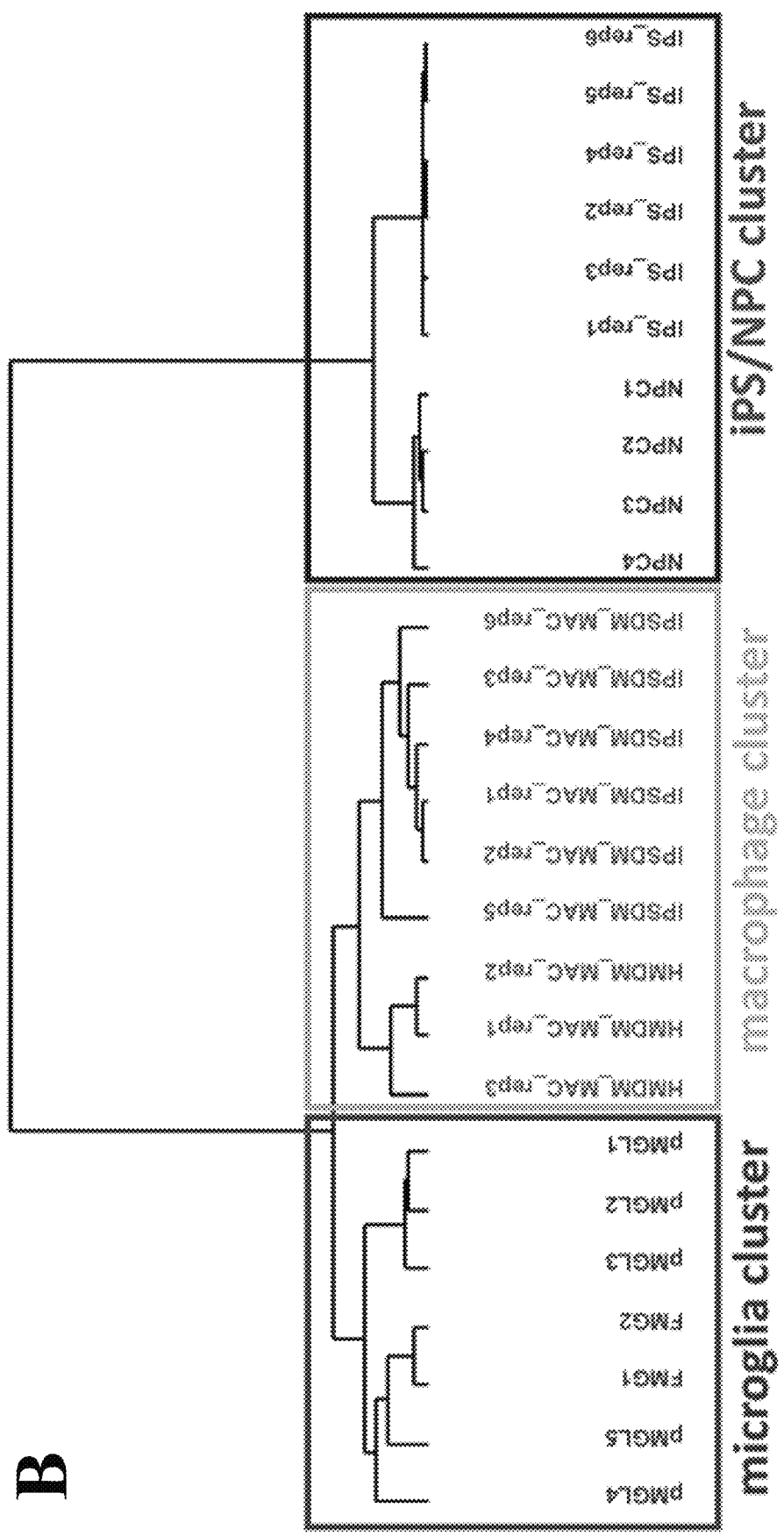
Figure 15:
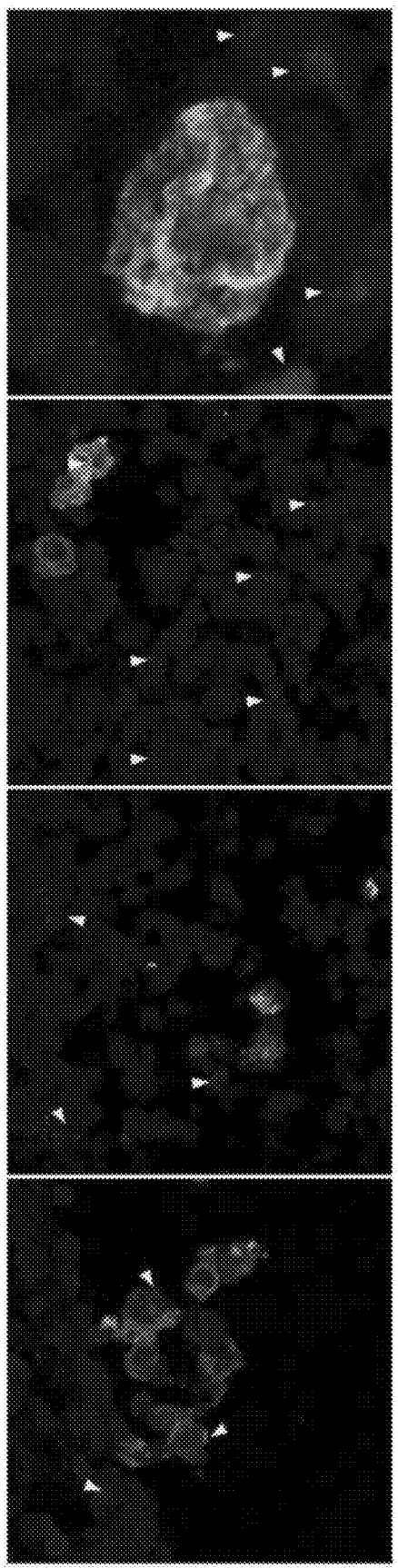
FIG. 15 shows in red the spread of Zika virus, from green microglia, invading a neural organoid in blue.
Figure 16:
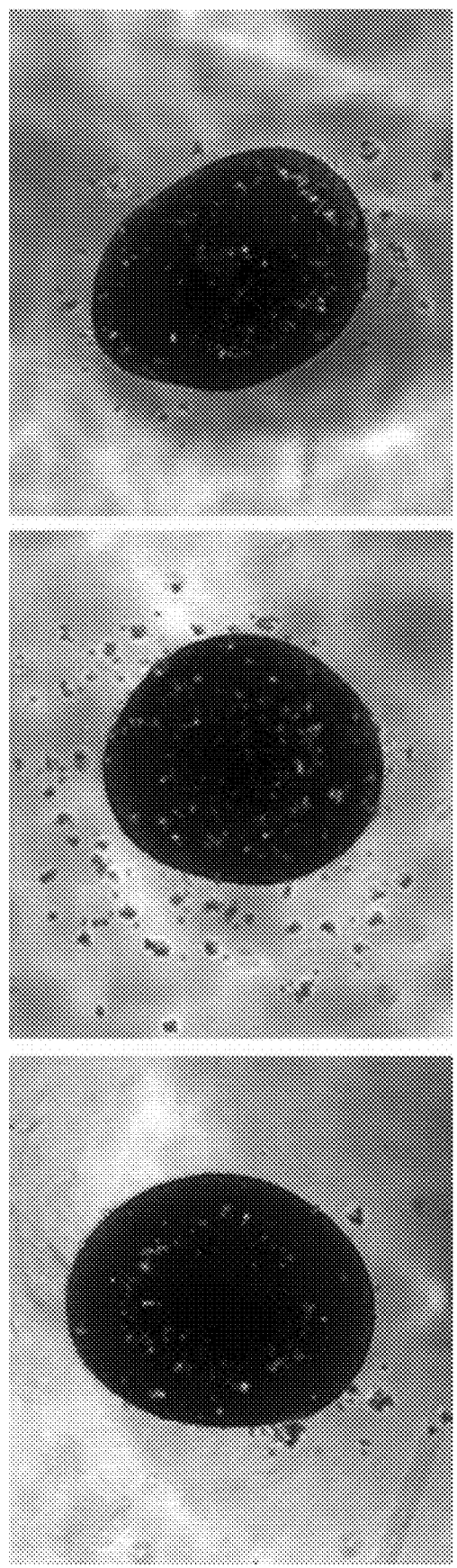
FIG. 16 shows GFP labeled microglia invading 3 organoids. Organoids are made from the Nbd medium as described herein, and are fully compatible with all the cells. They are formed from the reaggregation of 30000 early passage neural progenitor cells, grown for weeks in NBd+ growth factors.
Figure 17:
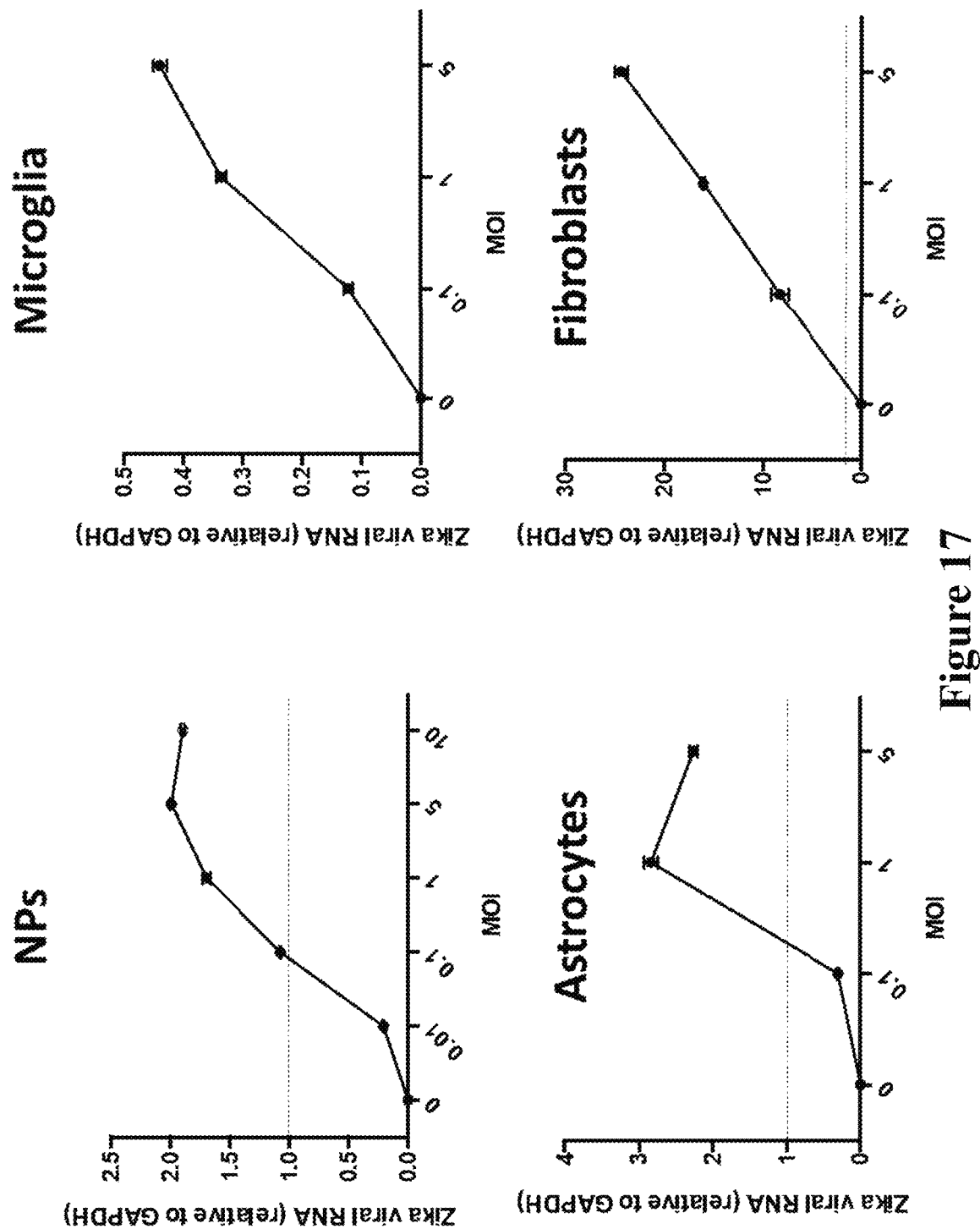
FIG. 17 shows Zika viral RNA detection (qPCR) in human microglial cells, NPCs, fibroblasts, and astrocytes.
Figure 18:
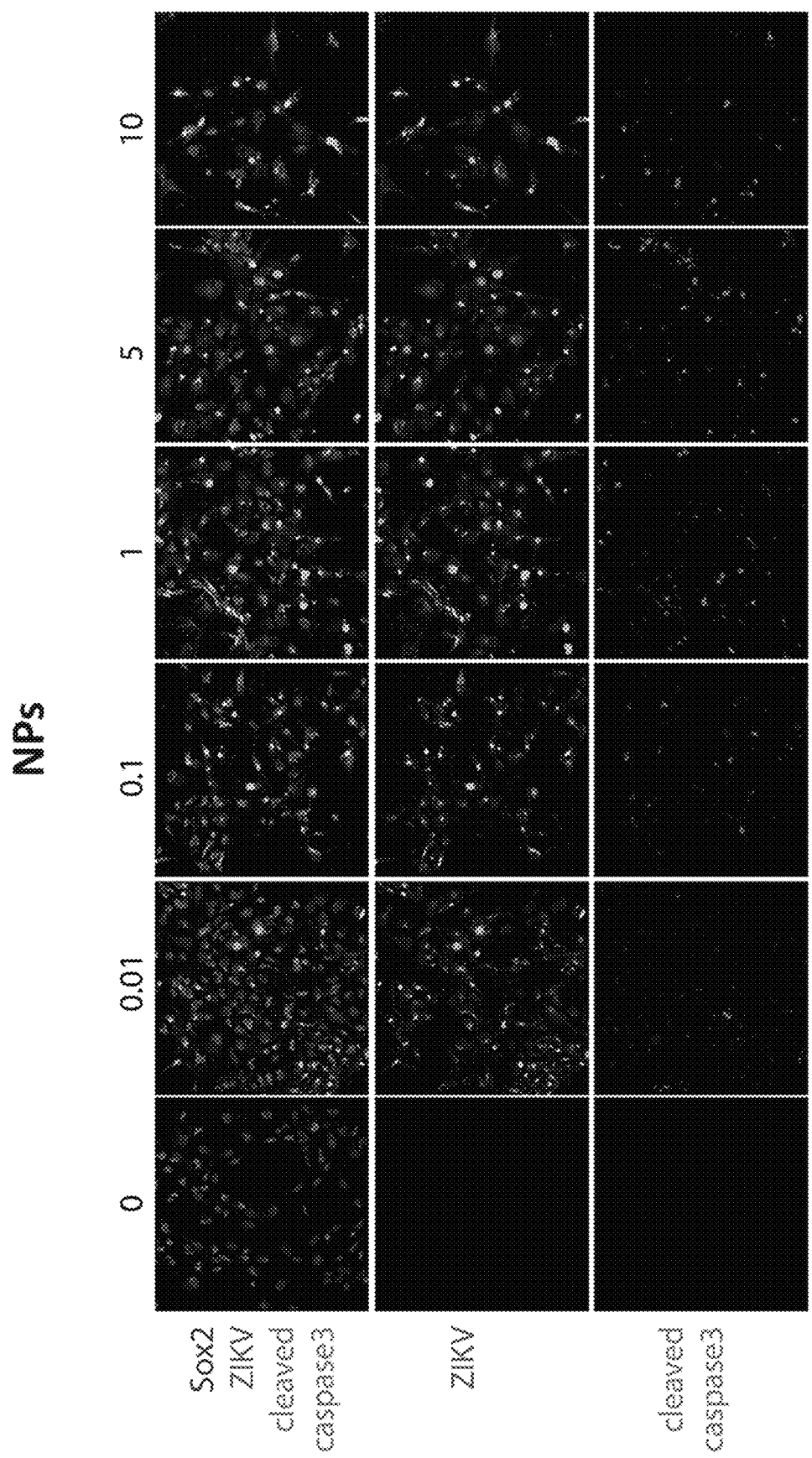
FIG. 18 shows Zika virus infection and replication in neural progenitor cells (NPCs), referred to here and in the figure itself as NP.
Figure 19:
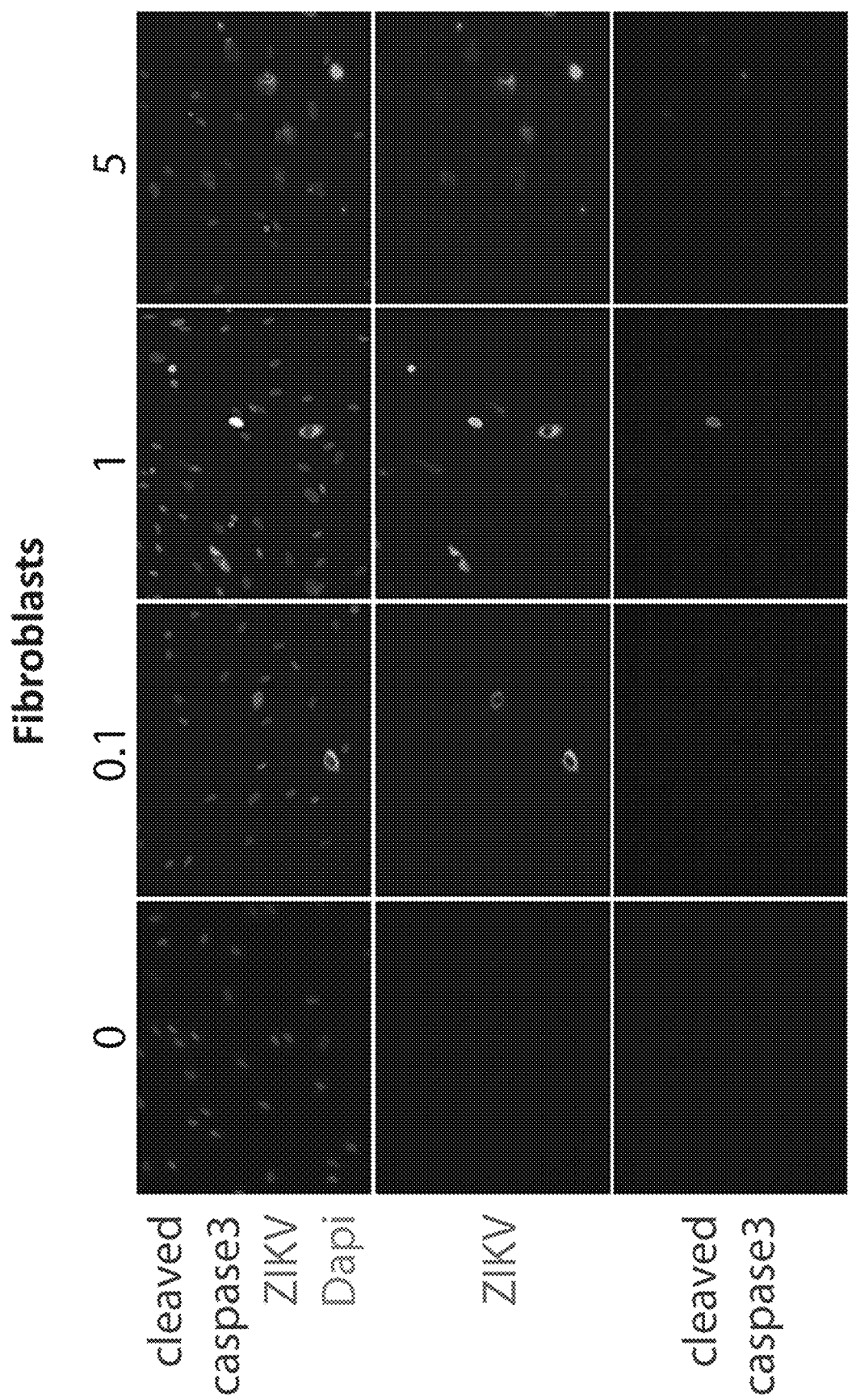
FIG. 19 shows Zika virus infection in human fibroblasts.
Figure 20:
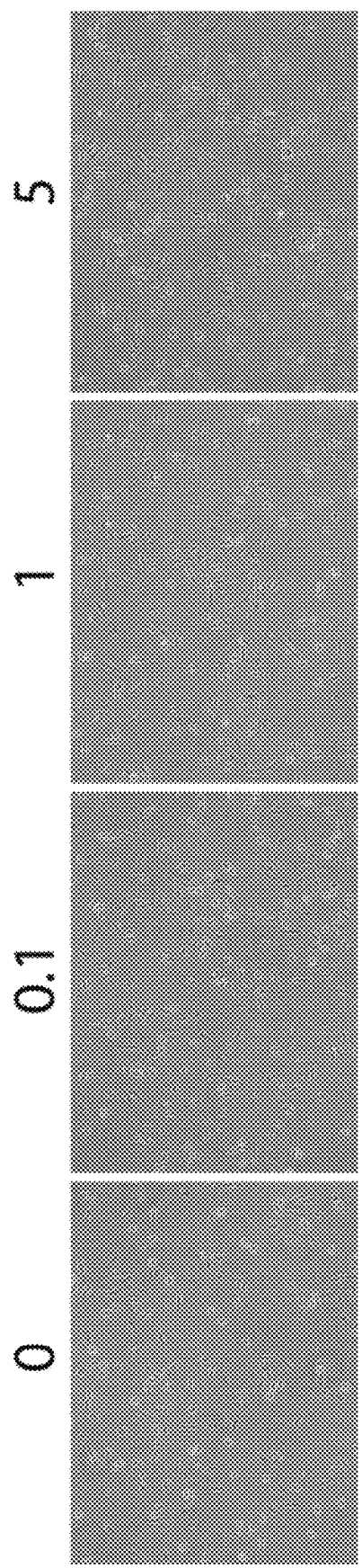
FIG. 20 shows Zika virus infection in human microglia cells. No obvious effects, such as changes in morphology or cell death, were observed. Cells were positive for viral genome by qPCR.
Figure 21:
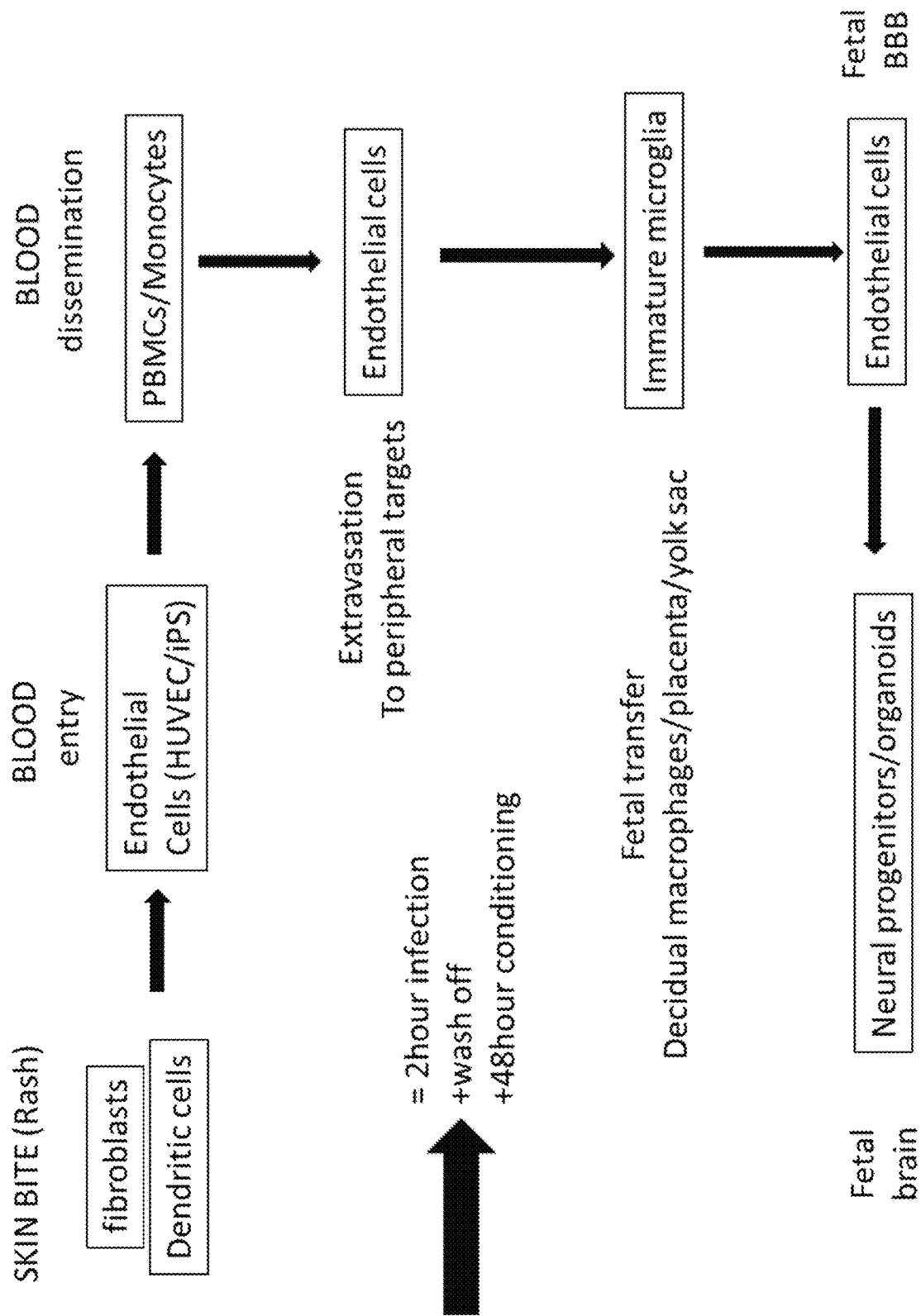
FIG. 21 is a schematic showing hematogenous dissemination in a dish.

These genes, whose transcripts are among the most abundant in pMGLs, have been identified as risk factors for sporadic forms of Alzheimer's disease. Likewise, HEXB, a causal gene for the lysosomal storage Sandhoff disease, was highly expressed in pMGLs, supporting the interest in microglial catabolism of GM2 ganglioside. NPCs derived from the same pluripotent stem cells and further differentiated into complex cultures of neurons and glia (Diff. NPCs, see FIG. 11) did not express any of these genes to significant levels (FIG. 10 and FIG. 13), highlighting the lack of overlap between these mesodermal and neuro-ectodermal lineages, despite their side-by side residence in the brain, in vivo. A consensus subset of genes was used that is highly expressed in microglia but poorly expressed in other macrophages, combining the most relevant genes of the microglial sensome, the unique TGFβ-dependent signature of microglia, and the microglial cassette found to be upregulated in TMEM119+ microglia during postnatal mouse development, to characterize pMGLs (see Table 3 for microglial genes compounded from Bennett et al. 2016). These include the purinergic sensors P2Y12/13, the proto-oncogene MERTK, the phospholipid binding protein PROS1, the putative synaptic tagging complement factor C1QA, the inhibitory receptor LAIR1, the GPCR GPR34, the ecto-nucleotidase ENTPD1, the transmembrane protein TMEM119, and the main TGFβ signaling partners TGFβ1 and TGFβR1. The expression of these markers appears to be positively correlated to maturation time in vivo, increasing exponentially in adult animals as compared to newborns. Conversely, their expression seems to be negatively correlated with time in culture, being highest in freshly isolated cells and lowest in maintained primary cells and transformed lines. Most of these genes are in fact expressed at higher levels in pMGLs than in primary human fetal microglia (FIG. 10A, FIG. 13), supporting their identity as in vitro generated microglia. Notably, these genes are expressed at low levels, if at all, in cultured macrophage cell lines as well as in previously described mouse ES-derived microglia. Conversely, genes such SLPI, SAA1/2, PRG4, CFP, CD51, CRIP1 are expected to be highly expressed in peripheral macrophages, and low in microglia: in accordance, these genes are in the lower expression quartile of the dataset. Genes such as GPR56 and BIN1 are expressed in microglia and in other CNS cell types, but have not been described in peripheral macrophages. Accordingly, FIG. 13C shows their very significant expression in pMGLs, fMG, as well as differentiated NPCs. Unbiased hierarchical clustering was performed on the data against previously published sequencing for primary and induced macrophages. As expected, all myeloid cells cluster away from parental iPS cells and NPCs. Strikingly, the pMGLs and primary fetal microglia cluster together, separately from other macrophages (FIG. 14B).

In the mouse, several microglia-specific genes appear to be upregulated in brain-resident microglia through early postnatal development. For example, SELPLG, CST3, TXNIP, P2RY13, OLFML3 are upregulated (respectively 16, 11, 9, 5 and 5-fold) between embryonic day 17 and postnatal day 60. As demonstrated in the data disclosed herein, SELPLG, CST3 and TXNIP are already expressed at high levels in both FMGs and pMGLs, while OLFML3 and P2RY13 are each 4-fold higher in pMGLs compared to FMGs. pMGLs also display high expression of both PU.1 and IRF8, but very low levels of MYB (FIG. 14A) consistent with microglia emerging from PU.1 and IRF8-dependent, but MYB-independent cells. Unbiased hierarchical clustering was performed on the data against previously published data on primary human brain cells isolated by immunopanning, including neurons, fetal and mature astrocytes, and adult microglia. It was found that pMGLs form a cluster with both fetal and mature primary microglia, while the NPCs cluster with other brain cells, close to fetal astrocytes (FIG. 10B).

Example 7: The pMGL Phenotype is Affected by Co-Cultivation with Neurons

Exposure to undifferentiated neural progenitor conditioned medium maintains the rounded phenotype of immature microglia and promotes their proliferation. It was tested whether maturation of pMGLs in the presence of human pluripotent stem cell-derived mature neural cells would further refine their molecular signature (FIG. 11A, top panel). Principal component analysis of the transcriptome revealed that primary fetal microglia and pMGLs cluster tightly together along PC1, and segregate away from differentiated neural progenitors cultured in the exact same conditions (FIG. 11B). Thus, the difference between NPs and pMGLs along PC1 may reflect the main myeloid vs neural identity, accounting for 80% of sample variance, while the variation along PC2 (5% of sample variance) may be refined by tissue residency, ECM and cell/cell interactions.

To directly test this notion, pMGLs were grown in conditioned medium from differentiating neural cultures (defined before conditioning, with no other variation in recombinant growth factor concentrations). FIG. 11B shows that, after 2 weeks, the pMGLs partially shifted their signature towards that of primary microglia along the PC2 axis, while primary microglia were unaffected by the exposure. In vivo, microglia are extensively ramified in the absence of exogenous stimulation by disease or injury. Cultured steady-state mature pMGL display a molecular signature close to that of in vivo cells, and exposure to secreted factors from neural cultures refines this signature. To test whether physical embedding and maturation of pMGLs in a 3D organotypic neuroglial environment would accentuate their branching patterns and allow us to observe their surveying behavior, immature pMGLs were transduced with a GFP lentivirus and the GFP-positive pMGLs were re-aggregated with pre-differentiated neural cultures, at a stage where neurons have already become post-mitotic and gliogenesis is ongoing (>4 weeks). The re-aggregates were either kept in spinning suspension cultures to maximize viability, or as 200 μm-thick cultures in transwells, so as to avoid triggering pMGL activation from hypoxia of the surrounding tissue and allow live observation. In this context, an entire spheroid or cellular stack is self-assembling, laying down its own extra-cellular matrix without need for additional scaffold (FIG. 11A, lower panel).

The neural progenitor cells progressively differentiated into neurons and macro-glia (astrocytes, oligodendrocytes), and would be devoid of any microglia without the exogenous addition of pMGLs. FIG. 11C shows that GFP-labeled pMGLs, which had adopted rounded to first-order ramified morphologies when cultured on plastic, integrated into the three-dimensional cultures, tiled the space, and projected highly branched ramifications (FIG. 11D). The 3D culture matrix is a cortex-like mesh of MAP2 positive neurites and GFAP positive astrocytic branches (FIG. 11E). Live Imaging of the GFP positive pMGL branches in situ showed rapid extension and retraction of filopodial arbor termini (FIG. 11F and FIG. 11G). These results suggest that pMGLs can integrate into organotypic neural cultures, and mature into what is currently defined as resting yet dynamically motile microglia. This magnitude of extension and retraction is not observed in 2D cultures on primaria or glass coverslips, where non-amoeboid pMGLs only display terminal ruffle movement, on a much smaller scale.

Example 8: Embedded pMGLs Rapidly Respond to Cellular Damage

One of the characteristics of microglia in vivo is their ability to survey the parenchyma from their static tiling positions, yet revert to an amoeboid and actively migrating state in response to injury. Migration towards a site of cellular damage is driven by purinergic receptors such as P2RY12/13, in response to ATP/ADP release from dying cells. The 3D culture system disclosed herein was used to model such localized damage and observe the behavior of microglia in real-time. FIG. 11H displays the timelapse reaction of embedded GFP+ microglia to a focal laser injury (yellow arrowhead at 5'). Microglia reacted within minutes by extending a single long process towards the injury center, making contact with the damaged zone. They then rapidly migrated their cell body to surround the damaged area. In contrast, microglia away from the injury site stayed in place. Colored traces represent the cumulative path of each individual cell, exemplifying the direct migration of microglia initially present within 100 μm of the wound, likely within a certain chemo-attractive concentration threshold of the purinergic gradient triggered by the release of cellular contents in the confined 3D structure.

Human ES and iPS Cell Cultures

Human ES cell line WIBR1/2/3 and hES-Rett were cultured in 5% 02 on mitomycin C-inactivated mouse embryonic fibroblasts (MEFs) in hESC medium, containing DMEM/F12 (Thermo), 15% fetal bovine serum (Hyclone), 5% knockout serum replacement (Thermo), 1% nonessential amino acids (Invitrogen), 1 mM glutamine (Thermo), 0.1 mM β-mercaptoethanol (Sigma) and 4 ng/ml bFGF (Thermo). Cultures were passaged manually or with 1 mg/ml collagenase type IV (Thermo) every 5-7 days. iPS-wt1/2/3, iPS-fAD2, iPS-AMN1/2/3 and iPS-ALD1/2/3/4 were reprogrammed from patient fibroblasts using the constitutive excisable STEMCCA lentivirus (OSKM) and maintained in the same conditions as WIBR1/2/3. iPS-wt4/5, iPS-fAD1/3 were reprogrammed using non-integrative Sendai virus (OSKML), and maintained on inactivated mouse embryonic fibroblasts in serum-free hES medium containing DMEM/F12 (Thermo), 20% knockout serum replacement (Thermo), 1% non-essential amino acids (Thermo), 1 mM glutamax (Thermo), 0.1 mM β-mercaptoethanol (Sigma) and 12 ng/ml bFGF (Thermo). All lines were maintained for over 50 passages, and verified for stable expression of Oct3/4, Nanog and TRA1-60.

Differentiation to Neural Progenitors and Maintenance

Differentiation of human ES and iPS cells to neural progenitors in 2-D adherent culture was performed as follows: 2 million human ES or iPS were passaged onto matrigel-coated dishes using PBS w/o Ca2+/Mg2+, filtered through a 40 μm mesh to remove mEFS, and cultured directly in NGD medium containing dorsomorphin (2.5 mM, Stemgent), bFGF (long/mL, Thermo) and Insulin (additional 10 ng/mL) for 3 days until super-confluent. bFGF and Insulin were subsequently removed, and NGD+ dorsomorphin was replaced every day for 10 days. Cells were subsequently passaged 1:1 with PBS–/– when rosette lawns were observed throughout the culture. Rho-associated protein kinase (ROCK) inhibitor Y27632 (10 mM, Stemgent) was added to the medium during each of the first 3 passages. Initial passaging at no more than 1:2 ratio, followed by 1:3 to 1:6 every 5 days. Neural progenitors were expanded and maintained in NGD medium with 10 ng/ml bFGF, and additional 10 ng/mL Insulin (NGM medium).

Differentiation Towards Neurons and Glia

NPCs were differentiated into neurons and glia by removing FGF and culturing in NGD base levels of insulin (5 ug/mL) without retinoic acid addition (NGD contains no additional retinoid). To initiate differentiation, NPCs were plated in a 35 mm dish on 1% matrigel at $5*10^5/cm^2$ and fed 5 mL of NGD every 2-3 days. At 4 weeks, neurons appeared in the culture and a final dissociation was performed. The culture was dissociated in the presence of 0.05% DNaseI by incubation with Accutase (Stem Cell Technologies) for 30' at 37 deg C. with gentle agitation (bacterial rotator), resuspended in chilled HBSS/0.1% BSA and filtered through a 40 μM mesh before being centrifuged through a cushion of 4% BSA to remove cellular debris. For 2D cultures and for medium conditioning, cells were re-plated at $5*10^5/cm^2$ on 0.1% PEI-coated plastic or glass. For re-aggregation with pMGLs, 3D cultures were initiated by plating $1.5\times10^6$ cells in a 0.3 cm$^2$ PET transwell with 0.4 mm pores coated with 0.1% PEI. Cells were mixed with transduced pMGLs in a 1:10 ratio. Spheroid formation was initiated by reaggregating 3*10$^4$ NPCs per well in 96-well ultra-low attachment plate (corning), mixed with pMGLs at 1:10 ratio.

Differentiation Towards pMGLs

Colonies were treated with collagenase IV (1.5 mg/mL) and mildly triturated to form a suspension of uniform clumps, transferred directly to 5 mL MGdM (NGD+10 ng/mL IL-34+10 ng/mL CSF1), in ultralow attachment 6-well plates (corning). 6 confluent wells (~3×10$^6$ cells) were pooled into one suspension well. Embryoid bodies were monitored for appearance of two main identifiable types. The first group was composed of compact phase-bright neuralized spheroids, the second group were large, expanding cystic bodies, YS-EBs. Every 5 days, EBs were gently triturated to shear off loose cells of interest, settled, and the supernatant placed in a single well of a primaria 6-well 593 plate. Unattached cells and small EBs are washed with fresh MGdM. Attached cells are monitored for morphological characteristics of microglia/microglial precursors (compact nucleus, vacuoles, membrane ruffles, motility), and wells from 6 consecutive productions (one month) were pooled to constitute one synchronized population. Further maintenance was performed in MGM (NGD+100 ng/mL IL-34+5 ng/mL CSF1). Cells are sensitive to passaging, but can be lifted with Accutase, or preferentially with ice-cold PBS with 5 ng/mL CSF1. Assays and imaging were performed 4-5 days after passaging or feeding.

Lentivirus Production and Transduction

FU-GFP-IRES-PURO-W lentivirus constructs were used for pMGL transduction. VSVG-coated lentiviruses were generated in HEK293 cells as previously described 39. Subconfluent HEK293 cells were transfected using X-tremeGENE 9 (Roche), with a mixture of lentiviral construct and second generation packaging plasmids. Culture medium was changed 12 hours after transfection and collected 96 hours later. Virus-containing medium was filtered through 0.45 μm filter and concentrated by ultracentrifugation (23 krpm, 90', 4 C). pMGLs cultured in MGdM were transduced at an MOI of 10 (titer assessed by p24 ELISA). Medium was replaced after 12 hours, and cells were left to recover. Expression was evaluated by fluorescence microscopy without additional selection.

EdU Click-It Assay

EdU (10 μM, Life Technologies) was added to MGdM medium for 24 hours, after which cells or tissues were fixed using ice-cold methanol. EdU click-it assay was performed on fixed cells per the manufacturer's instruction (Life Technologies), followed by fluorescent immunostaining and imaging. Counting was performed by automated particle counting with Fiji. Data is represented as a ratio of EDU positive to DAPI positive nuclei. 6 random fields were chosen at 100× magnification, and averaged between two biological replicates to generate SEM and TTEST values.

Imaging

Cells and tissues were fixed with ice-cold methanol or 4% paraformaldehyde in PBS. After PFA fixation, permeabilization was effected with PBS containing 0.3% triton. Fixed and permabilized cells were blocked with 3% normal donkey serum. Primary antibodies were against TREM2 (Abcam), CD11b (Abcam), TMEM119 (Sigma/Atlas), P2RY12 (Sigma/Atlas), PU.1 (cell signaling) and visualized by secondary antibodies conjugated with Alexa 488, 568, 594, 647 (Life Technologies), followed by counter-staining with DAPI. Phase contrast and Fluorescent images of immunostaining, as well as time lapse movies, were captured on a widefield Nikon Ti2000 mounted with a SPOT RT monochrome camera. For 3D embedded microglia, observation was performed in the culture transwell, placed on a 1.5 coverslip Matek glass-bottom 35 mm dish. Optical sectioning through 3D neural cultures was performed on a Zeiss LSM 700 at 20× magnification. Live imaging and wound assay in 3D culture was performed on Zeiss LSM710, photo-ablation was performed with 2-photon 780 nm laser at 20% power, acquiring a 25 um optical slice at 10×.

Flow Cytometry

Single cell suspensions of PMGLs were blocked with FcR blocking reagent, 1% BSA, to avoid nonspecific antibody binding, in NGD medium without phenol red. They were labeled with preconjugated anti-CD11B-FITC (StemCells Tech.), anti-CD45-AF647 (Biolegend), anti-CD14-AF647 (Biolegend), and unconjugated mouse anti-IBA1 (abcam) and Rabbit anti-TMEM119 (Sigma). Unconjugated primaries were followed by appropriate AF647 conjugated secondaries. Sorting was performed on a customized FACS Aria (BD).

Phagocytosis Assay

For qualitative assessment of phagocytosis, 1 μm polystyrene red-orange fluospheres (Thermo) were left to settle at a density of 10$^7$/cm$^2$ on PEI coated plastic. pMGLs were added the next day at a density of 1000/cm$^2$. Cells were observed after 6 hours, displaying their migration on the lawn and the cytoplasmic bead uptake. Alternatively, beads were added directly to a pMGL culture medium at a concentration of 10$^8$ beads/mL. Phagocytosis was observed in real time, highlighting the rapid active uptake.

Primary Mouse Microglia Preparation

All culture conditions were initially tested with mouse primary microglia. C57Bl/6 neonates were cold/CO2 anesthetized in a dry ice chamber following approved protocols and whole brains were harvested. After meningeal removal, cortical cups were isolated, minced on ice, and crudely triturated with a wide-bore fire-polished pipette in a solution of Accutase (Life). The preparation was incubated at 37 C with rotation for 10', followed by further trituration with a narrowed pipette. The suspension was further incubated for 10' at 37 C with DNaseI 0.1%. The final trituration was left to settle for 1 minute, and the supernatant was filtered through a 70 μm mesh, and spun through a 4% BSA cushion to remove cell debris. This preparation was plated directly on matrigel coated plate, and grown in complete Neurobasal with 5% serum. After a week, loosely adherent microglia were harvested and further used on different surfaces. Alternatively, MACS sorting (Miltenyi) for CD11b was applied to the cortical suspension, following the manufacturer's instructions. Flow-through was discarded while retained cells were eluted directly onto test surfaces and used accordingly.

Primary Fetal Human Microglia:

was obtained from first trimester aborted fetuses from Sciencell (#1900), and cultured on primaria in MGdM and MGM.

RNA Extraction, Reverse Transcription and Quantitative PCR

Cells and tissues were homogenized and total RNA extracted using the RNeasy Micro kit (Qiagen) following manufacturer's instructions. Total RNA concentrations were measured using NanoDrop ND-1000 spectrophotometer. For RNAseq, RNA was directly analyzed and quality checked before sequencing. RNA was reverse transcribed into cDNA using Superscript III reverse transcriptase (Invitrogen) with random hexamer primers. Transcript abundance was determined by quantitative PCR using SYBR Green PCR mix (Applied Biosystems), with primer pairs against IL6, TNFα and GAPDH.

RNAseq and Analysis

Samples were prepared using the SMART-Seq v4 Ultra Low Input RNA Kit for Sequencing (Clontech), according to manufacturer's protocols and using 10 ng of input. Final libraries were evaluated for size using a Fragment Analyzer (Advanced Analytical Technologies) and quantified using both Qubit (Thermo Fisher) and qPCR (Roche LightCycler 480, KAPA Illumina Library Quantification Kit) before sequencing. RNA-seq 75 bp paired-end reads from Illumina were checked with FastQC and fastq_screen. Reads were mapped to human genome hg19 using TopHat v 2.0.13 with Ensembl annotation (GRCh37.75) in gtf format. FeatureCounts was used to obtain gene counts with default option. The gene counts were normalized with DESeq, and PCA plot was created with plotPCA function. Bar charts represent the average normalized raw reads for different PSC lines and primary samples (FMG n=2, pMGLs n=3, Diff. NPCs n=4). Gene ontology differently selected top features for FMG, pMGLs and differentiated NPCs, ran on the online Gene Ontology Consortium tool (geneontology.org). Hierarchical clustering was performed on quantile normalized FPKMs from the different GEO datasets. For HMDM and iPSDM, GSE55536 was used. For the comparison to adult human microglia, and other brain cells, GSE73721 was used.

Cytokine Profiler 2 mL of NGD was added to 100 k pMGLs in a 35 mm well and allowed to condition for 24 hours. For IFNg/LPS stimulation, LPS was added at 100 ng/mL along with 20 ng/mL IFNg at the onset. 400 uL of this supernatant were added to a prepared cytokine antibody panel membrane, per the manufacturer's instructions (R&D Systems, kits ARY005 and replacement ARY005B). After incubation, the membranes were revealed with ECL reagent. Plots represent the average pixel greyscale intensity of 100 pixels-disk (technical duplicate for each cytokine), normalized to background. Ratios represent greyscale ratios in arbitrary units.

Table 1 below shows complete composition of NGD base medium, given for 1 L of medium. Defined components are from commercially available supplements such as Gem21 and Neuroplex N2 (Gemini Biosciences). A full complement of energetic substrates is combined into the base (D-Galactose, D-Glucose, Glutamine/Glutamax, Lactate, Pyruvate). Physiological osmolarity is achieved by addition of 5M NaCl to a final osmolality of ~295 mOsm; additional lipids are present as lipidated BSA (Albumax I). The main extracellular concentrations of the human cerebrospinal fluid are matched for sodium, chloride, calcium and magnesium, as is overall osmolarity.

TABLE 1

| For 1 L of ND | | |
|---|---|---|
| Protein carrier | Defined | Commercial Equivalent |
| BSA, fatty acid free Fraction V | 1250 mg | 20 mL Gem21 + 10 mL N2 |
| Hormones | | |
| Human Transferrin | 52.5 mg | |
| Human Recombinant Insulin | 24.5 mg | |
| Progesterone | 6.3 ug | |
| Corticosterone | 0.01 mg | |
| T3 (triodo-I-thyronine) | 1 ug | |

TABLE 1-continued

| For 1 L of ND | | |
|---|---|---|
| Protein carrier | Defined | Commercial Equivalent |
| Antioxidants | | |
| Glutathione (reduced) | 0.5 mg | |
| Catalase | 1.25 mg | |
| Superoxide Dismutase | 1.25 mg | |
| DL Alpha Tocopherol Acetate | 0.5 mg | |
| DL Alpha-Tocopherol | 0.5 mg | |
| Fatty acid metabolism | | |
| Linoleic Acid | 0.5 mg | |
| lipoic acid | 23.5 ug | |
| Linolenic Acid | 0.5 mg | |
| L-Carnitine HCl | 1 mg | |
| Essential precursors | | |
| Putrescine 2HCl | 16.1 mg | |
| Ethanolamine HCl | 0.5 mg | |
| Sodium Selenite | 7.2 ug | |
| Energetic substrates | | |
| D-Galactose | 7.5 mg | |
| lactic acid (85% syrup stock) | | 200 uL |
| Sodium Pyruvate (100 mM stock) | | 10 mL |
| glutamax (100x stock) | | 10 mL |
| Biotin | | 3.5 ug |
| lipidated BSA (Albumax I) | | 2 g |
| Ascorbic Acid | | 2.5 mg |
| Pen/Strep | | 10 mL |
| NaCl 5M | | 10 mL |
| Neurobasal | | qsp 1 L |

Table 2 below shows variability in deriving pMGLs from a panel of pluripotent stem cell lines. pMGLs were derived from 20 different human ES and iPS cell lines to assess variability and reproducibility of the differentiation protocol. Neural progenitor cells (NPCs) were derived in parallel cultures for most lines. The table indicates the genotype of the ES or iPS cell lines used and summarizes the time (between 2-4 weeks) and efficiency (+, ++, +++) of pMGL and NPC generation. Variations of pMGL induction were observed between individual lines but did not correlate either with reprogramming method, genotype, neuralization propensity or initial culture conditions. KSR=knockout serum replacer; lentivirus=excised inducible or constitutive polycistronic; AD=Alzheimer's disease; AMN=adrenomyeloneuropathy; cALD=cerebral Adrenoleukodystrophy; mEFs=mouse feeders. n/a=not applicable. n/d=not determined. For pMGLs: +/++/+++~0.1×/0.2×/0.4× of PSC input in 4 weeks of collection (e.g 2×10$^6$ iPS-ALD1 cells yields 8*10$^5$ pMGLs at 4 weeks, 8×10$^6$ at 8 weeks. For NPCs: +/++/+++~2.5×/5×/10× of PSC input after 2 weeks of dorsomorphin differentiation (e.g. starting with 10$^6$ WIBR3 hES cells yields 10*10$^6$ neural progenitor cells after 3-4 weeks).

TABLE 2

| Line | Disease Model | pMGLs onset (weeks) | PMGLs End (weeks) | pMGLs | NPCs | Reprogramming method | PSC culture conditions |
|---|---|---|---|---|---|---|---|
| hES-wibr1 | wt hES | 3 | 8 | ++ | + | n/a | Serum/KSR/mEFS |
| hES-wibr2 | wt hES | 4 | n/d | + | ++ | n/a | Serum/KSR/Mefs |
| hES-wibr3 | wt hES | 4 | n/d | + | +++ | n/a | Serum/KSR/mEFS |
| iPS-wt1 | wt | 3 | 8 | ++ | ++ | lentivirus | Serum/KSR/Mefs |
| iPS-wt2 | wt | 3 | 8 | ++ | +++ | lentivirus | Serum/KSR/Mefs |
| iPS-wt3 | wt | 4 | 8 | ++ | +++ | lentivirus | Serum/KSR/mEFS |
| iPS-wt4 | wt | 2 | 6 | +++ | n/d | Sendai | KSR/mEFs |
| iPS-wt5 | wt | 4 | n/d | + | n/d | Sendai | KSR/mEFs |
| iPS-fAD1 | AD | 2 | 8 | +++ | +++ | Sendai | KSR/mEFs |
| iPS-fAD2 | AD | 2 | 8 | +++ | n/d | lentivirus | Serum/KSR/mEFs |
| iPS-fAD3 | AD | 4 | n/d | + | n/d | Sendai | KSR/mEFs |
| iPS-AMN1 | AMN | 2 | 8 | +++ | ++ | lentivirus | Serum/KSR/mEFS |
| iPS-AMN2 | AMN | 3 | n/d | + | +++ | lentivirus | Serum/KSR/mEFS |
| iPS-AMN3 | AMN | 4 | 8 | ++ | +++ | lentivirus | Serum/KSR/mEFS |
| iPS-ALD1 | cALD | 2 | 8 | +++ | +++ | lentivirus | Serum/KSR/mEFS |
| iPS-ALD2 | cALD | 4 | n/d | + | +++ | lentivirus | Serum/KSR/mEFS |
| iPS-ALD3 | cALD | 2 | n/d | + | ++ | lentivirus | Serum/KSR/mEFS |
| iPS-ALD4 | cALD | 3 | 8 | ++ | +++ | lentivirus | Serum/KSR/mEFS |
| hES-RETT | MeCP2 null | 3 | 8 | ++ | + | n/a | Serum/KSR/mEFS |

Table 3 below shows gene ontology categories enriched in the top 300 features of RNAseq transcriptomes, in pMGLs and human fetal microglia. This table is restricted to GSEA scores above 5, comparing fetal microglia (n=3) and pMGLs (n=6). The list highlights the immune nature of these cells, and the largely overlapping functional categories (antigen processing and presentation, MHCII, and metabolic processes). Of note, the presence of an IFNγ signature in fetal cells not found in pMGLs, and presence of an ECM remodeling signature in pMGLs, not found in fetal cells.

TABLE 3

| PSC-derived pMGLs | GSE score | P-value | Human FETAL MG | GSE score | P-value |
|---|---|---|---|---|---|
| antigen processing and presentation (GO:0019882) | >5 | 7.61E-11 | antigen processing and presentation (GO:0019882) | >5 | 1.43E-14 |
| antigen processing and presentation of exogenous antigen (GO:0019884) | >5 | 3.96E-10 | antigen processing and presentation of exogenous antigen (GO:0019884) | >5 | 5.03E-13 |
| antigen processing and presentation of exogenous peptide antigen (GO:0002478) | >5 | 1.79E-10 | antigen processing and presentation of exogenous peptide antigen (GO:0002478) | >5 | 2.02E-13 |
| antigen processing and presentation of exogenous peptide antigen via MHC class I (GO:0042590) | >5 | 2.52E-05 | antigen processing and presentation of exogenous peptide antigen via MHC class I (GO:0042590) | >5 | 2.66E-02 |
| antigen processing and presentation of exogenous peptide antigen via MHC | >5 | 1.63E-04 | | | |

TABLE 3-continued

| PSC-derived pMGLs | GSE score | P-value | Human FETAL MG | GSE score | P-value |
|---|---|---|---|---|---|
| class I, TAP-dependent (GO:0002479) | | | | | |
| antigen processing and presentation of exogenous peptide antigen via MHC class II (GO:0019886) | >5 | 1.38E−03 | antigen processing and presentation of exogenous peptide antigen via MHC class II (GO:0019886) | >5 | 8.37E−10 |
| antigen processing and presentation of peptide antigen (GO:0048002) | >5 | 1.16E−09 | antigen processing and presentation of peptide antigen (GO:0048002) | >5 | 1.73E−12 |
| antigen processing and presentation of peptide antigen via MHC class I (GO:0002474) | >5 | 5.69E−06 | antigen processing and presentation of peptide antigen via MHC class I (GO:0002474) | >5 | 4.51E−03 |
| antigen processing and presentation of peptide antigen via MHC class II (GO:0002495) | >5 | 1.70E−03 | antigen processing and presentation of peptide antigen via MHC class II (GO:0002495) | >5 | 1.17E−09 |
| antigen processing and presentation of peptide or polysaccharide antigen via MHC class II (GO:0002504) | >5 | 2.54E−03 | antigen processing and presentation of peptide or polysaccharide antigen via MHC class II (GO:0002504) | >5 | 2.24E−09 |
| ATP hydrolysis coupled proton transport (GO:0015991) | >5 | 1.23E−04 | ATP hydrolysis coupled proton transport (GO:0015991) | >5 | 1.33E−04 |
| ATP metabolic process (GO:0046034) | >5 | 1.02E−04 | ATP metabolic process (GO:0046034) | >5 | 1.17E−04 |
| | | | carbohydrate catabolic process (GO:0016052) | >5 | 7.73E−03 |
| cellular iron ion homeostasis (GO:0006879) | >5 | 1.33E−03 | cellular iron ion homeostasis (GO:0006879) | >5 | 1.37E−04 |
| cellular respiration (GO:0045333) | >5 | 1.73E−04 | cellular respiration (GO:0045333) | >5 | 1.98E−04 |
| | | | cellular response to interferon-gamma (GO:0071346) | >5 | 4.49E−03 |
| | | | cellular response to type I interferon (GO:0071357) | >5 | 7.95E−03 |
| cellular transition metal ion homeostasis (GO:0046916) | >5 | 3.08E−03 | cellular transition metal ion homeostasis (GO:0046916) | >5 | 4.03E−04 |
| cotranslational protein targeting to membrane (GO:0006613) | >5 | 8.35E−03 | | | |
| electron transport chain (GO:0022900) | >5 | 1.76E−04 | electron transport chain (GO:0022900) | >5 | 2.54E−05 |
| endoplasmic reticulum unfolded protein response (GO:0030968) | >5 | 4.30E−02 | | | |
| energy coupled proton transmembrane transport, against electrochemical gradient (GO:0015988) | >5 | 1.23E−04 | energy coupled proton transmembrane transport, against electrochemical gradient (GO:0015988) | >5 | 1.33E−04 |
| energy derivation by oxidation of organic compounds (GO:0015980) | >5 | 4.56E−10 | energy derivation by oxidation of organic compounds (GO:0015980) | >5 | 3.69E−09 |

TABLE 3-continued

| PSC-derived pMGLs | GSE score | P-value | Human FETAL MG | GSE score | P-value |
|---|---|---|---|---|---|
| energy reserve metabolic process (GO:0006112) | >5 | 5.11E−03 | energy reserve metabolic process (GO:0006112) | >5 | 3.41E−02 |
| ephrin receptor signaling pathway (GO:0048013) | >5 | 1.11E−03 | ephrin receptor signaling pathway (GO:0048013) | >5 | 1.05E−02 |
| establishment of protein localization to endoplasmic reticulum (GO:0072599) | >5 | 1.27E−02 | | | |
| extracellular matrix disassembly (GO:0022617) | >5 | 1.37E−02 | | | |
| extracellular matrix organization (GO:0030198) | >5 | 2.24E−09 | | | |
| extracellular structure organization (GO:0043062) | >5 | 2.40E−09 | | | |
| | | | ferric iron transport (GO:0015682) | >5 | 1.03E−03 |
| generation of precursor metabolites and energy (GO:0006091) | >5 | 1.25E−09 | generation of precursor metabolites and energy (GO:0006091) | >5 | 1.62E−09 |
| hydrogen ion transmembrane transport (GO:1902600) | >5 | 2.41E−06 | hydrogen ion transmembrane transport (GO:1902600) | >5 | 2.37E−09 |
| hydrogen transport (GO:0006818) | >5 | 1.50E−05 | hydrogen transport (GO:0006818) | >5 | 2.96E−08 |

TABLE 4 below shows a gene list of the top 200 genes overexpressed in pMGLs over FMGs.
top 200 overexpressed pMGL vs FMG

| | | | |
|---|---|---|---|
| COMP | CD248 | MFAP2 | COL15A1 |
| RPS4Y1 | C3orf80 | MFAP4 | MMP23A |
| AC037459.4 | NDNF | THBS1 | COL21A1 |
| GDF10 | COL6A3 | WNT2B | LRRN4CL |
| FNDC1 | FAM177B | CTC-429P9.4 | NPY5R |
| H19 | RP11-136K7.2 | CTD-2203K17.1 | RERG |
| NTS | NAALAD2 | LOXL2 | TNFSF18 |
| APLNR | TRDN | FRZB | MEDAG |
| ZFY | TMEM132D | ALX1 | ECM2 |
| RP1-65P5.3 | ADAMTSL5 | KREMEN2 | COL1A2 |
| NALCN | PTGER3 | AOC2 | KIAA1462 |
| SFRP2 | BANK1 | PTX3 | COL26A1 |
| THBS4 | LGR5 | DPT | LHX9 |
| OSR2 | FEZF2 | AC098617.1 | RPL30P11 |
| LINC00960 | EFCC1 | PRR15 | TMEM215 |
| RSPO2 | RP11-122M14.1 | KRT19 | FGF7 |
| MAB21L2 | LRRC15 | CRLF1 | FAP |
| KCNK15 | TLL2 | LINC00968 | AC132217.4 |
| ASPN | PIEZO2 | ITGA4 | LINC00601 |
| GREM2 | NLGN4Y | C10orf90 | GJA3 |
| C1orf158 | IFITM1 | RP11-649A16.1 | OLFML2A |
| CPXM2 | IGFBP3 | RP11-655M14.13 | RP11-208N14.4 |
| PYGM | KCNN2 | LINC01088 | DYNLRB2 |
| CD34 | RP11-397A15.4 | KRT8 | PCDH12 |
| APCDD1L | AGR2 | RP11-517I3.1 | COL5A2 |
| AC072062.1 | COL23A1 | HAPLN1 | DMKN |
| TWIST1 | FCER2 | FAM216B | EMB |
| WISP2 | CILP | C11orf88 | NEFL |
| DKK1 | GDF6 | CDH13 | GPR116 |
| MKX | PLD5 | PGA4 | IL6 |
| AC004702.2 | CORIN | ZNF215 | SPAG6 |
| TWIST2 | EGFL6 | TGM1 | RP11-820L6.1 |
| TMEM74 | MGP | ALDH1L1-AS2 | PEBP4 |
| SIX1 | FBLN5 | POU6F2 | MYO3A |
| FGF18 | MTRNR2L1 | WNT11 | FOXA1 |
| SNED1 | MXRA5 | RP11-1084J3.4 | WDR49 |
| POSTN | ABI3BP | LUM | PGA5 |
| CHODL | AGTR1 | GSC | GATA6 |
| COL5A1 | C1QTNF3 | ICAM5 | RP4-665N4.4 |
| IRX5 | EFCAB1 | SVILP1 | PSG5 |
| COL12A1 | GXYLT2 | BTBD11 | MSX2 |
| MIR4500HG | LTBP2 | KIAA1199 | KCNK1 |
| GAS2 | TTC29 | TINCR | RP11-627D16.1 |
| FMO1 | PRSS12 | PIGR | CREB3L1 |
| ADAMTS2 | AQP1 | SEMA3D | ENDOU |
| ALDH1A3 | F2RL2 | MAB21L1 | CCK |
| STON1-GTF2A1L | CTD-2207P18.1 | RP11-92A5.2 | ENPP1 |
| RP11-385J1.2 | PITX1 | ITGA11 | VGLL3 |
| LOXL4 | ITGBL1 | MAPK15 | KLHL29 |
| NEFM | EPGN | CACNA1A | RP11-52B19.10 |

Table 5 below shows molecular function gene ontology giving gene enrichment from table 4. The list highlights that major differences between pMGLs and their primary counterpart invoke cell adhesion molecules and extracellular matrix interaction molecules.

TABLE 5

| GO molecular function complete | enrichment | p-value |
|---|---|---|
| cell adhesion molecule binding (GO:0050839) | 10.06 | 1.15E−07 |

TABLE 5-continued

| GO molecular function complete | enrichment | p-value |
|---|---|---|
| heparin binding (GO:0008201) | 11.18 | 1.34E−07 |
| sulfur compound binding (GO:1901681) | 8.54 | 2.73E−07 |
| glycosaminoglycan binding (GO:0005539) | 9.22 | 3.78E−07 |
| integrin binding (GO:0005178) | 13.01 | 3.51E−06 |
| collagen binding (GO:0005518) | 17.36 | 9.87E−06 |
| extracellular matrix structural constituent (GO:0005201) | 14.28 | 5.19E−05 |
| receptor binding (GO:0005102) | 2.87 | 5.70E−05 |
| fibronectin binding (GO:0001968) | 26.87 | 3.36E−04 |
| scavenger receptor activity (GO:0005044) | 16.72 | 5.17E−03 |
| growth factor activity (GO:0008083) | 6.97 | 1.90E−02 |
| calcium ion binding (GO:0005509) | 3.18 | 4.44E−02 |
| cargo receptor activity (GO:0038024) | 11.4 | 4.49E−02 |

Table 6 below shows biological processes enrichment for the top 200 genes upregulated in pMGLs compared to NPCs. Broadly confirming the innate immune nature of pMGLs, more specifically their myeloid genealogy.

TABLE 6

Processes UP in pMGL compared to NPCs

| GO biological process complete | enrichment | p-value |
|---|---|---|
| immune system process (GO:0002376) | 4.92 | 1.13E−33 |
| immune response (GO:0006955) | 6.7 | 2.41E−30 |
| regulation of immune system process (GO:0002682) | 5.13 | 5.42E−23 |
| positive regulation of immune system process (GO:0002684) | 6.53 | 1.02E−21 |
| defense response (GO:0006952) | 5.31 | 2.53E−21 |
| regulation of immune response (GO:0050776) | 6.53 | 3.63E−21 |
| response to stimulus (GO:0050896) | 1.98 | 1.38E−17 |
| innate immune response (GO:0045087) | 6.95 | 4.17E−16 |
| activation of immune response (GO:0002253) | 8.6 | 6.05E−16 |
| positive regulation of immune response (GO:0050778) | 6.9 | 2.21E−14 |
| adaptive immune response (GO:0002250) | 10.61 | 2.48E−14 |
| immune response-regulating signaling pathway (GO:0002764) | 8.13 | 1.80E−13 |
| immune response-activating signal transduction (GO:0002757) | 8.51 | 2.30E−13 |
| positive regulation of response to stimulus (GO:0048584) | 3.42 | 6.53E−13 |
| inflammatory response (GO:0006954) | 7.2 | 3.67E−12 |
| cell activation (GO:0001775) | 6.18 | 1.67E−11 |
| regulation of response to stimulus (GO:0048583) | 2.44 | 1.93E−11 |
| response to stress (GO:0006950) | 2.57 | 3.38E−11 |
| cell adhesion (GO:0007155) | 4.3 | 1.90E−10 |
| biological adhesion (GO:0022610) | 4.28 | 2.21E−10 |
| immune effector process (GO:0002252) | 6.44 | 5.90E−10 |
| cellular response to stimulus (GO:0051716) | 1.92 | 7.70E−10 |
| leukocyte activation (GO:0045321) | 6.78 | 1.94E−09 |
| cell communication (GO:0007154) | 2.01 | 5.19E−09 |
| leukocyte migration (GO:0050900) | 8.63 | 1.22E−08 |
| regulation of defense response (GO:0031347) | 4.75 | 1.35E−08 |
| endocytosis (GO:0006897) | 5.82 | 1.62E−08 |
| single organism signaling (GO:0044700) | 2 | 1.68E−08 |
| signaling (GO:0023052) | 2 | 1.74E−08 |
| signal transduction (GO:0007165) | 2.04 | 3.13E−08 |
| regulation of leukocyte proliferation (GO:0070663) | 9.66 | 3.39E−08 |
| immune response-regulating cell surface receptor signaling pathway (GO:0002768) | 7.37 | 5.04E−08 |
| positive regulation of defense response (GO:0031349) | 6.82 | 6.08E−08 |
| immune response-activating cell surface receptor signaling pathway (GO:0002429) | 7.73 | 7.87E−08 |
| regulation of lymphocyte proliferation (GO:0050670) | 9.6 | 1.62E−07 |
| regulation of mononuclear cell proliferation (GO:0032944) | 9.5 | 1.88E−07 |
| cell surface receptor signaling pathway (GO:0007166) | 2.7 | 5.56E−07 |
| phagocytosis (GO:0006909) | 9.59 | 7.18E−07 |
| regulation of response to wounding (GO:1903034) | 5.95 | 7.31E−07 |
| regulation of inflammatory response (GO:0050727) | 7.22 | 8.37E−07 |
| positive regulation of biological process (GO:0048518) | 1.91 | 9.76E−07 |
| biological regulation (GO:0065007) | 1.43 | 1.12E−06 |
| single-organism process (GO:0044699) | 1.35 | 1.64E−06 |
| single organismal cell-cell adhesion (GO:0016337) | 5.64 | 1.92E−06 |
| regulation of response to external stimulus (GO:0032101) | 3.82 | 2.60E−06 |
| single organism cell adhesion (GO:0098602) | 5.37 | 4.58E−06 |

TABLE 6-continued

Processes UP in pMGL compared to NPCs

| GO biological process complete | enrichment | p-value |
|---|---|---|
| regulation of T cell proliferation (GO:0042129) | 10.4 | 5.10E−06 |
| myeloid leukocyte activation (GO:0002274) | 13.07 | 1.07E−05 |
| regulation of biological process (GO:0050789) | 1.43 | 1.20E−05 |
| regulation of cell activation (GO:0050865) | 5.05 | 1.34E−05 |
| innate immune response-activating signal transduction (GO:0002758) | 8.53 | 1.36E−05 |
| response to external stimulus (GO:0009605) | 2.72 | 1.53E−05 |
| immune system development (GO:0002520) | 4.53 | 1.64E−05 |
| regulation of leukocyte activation (GO:0002694) | 5.16 | 2.37E−05 |
| activation of innate immune response (GO:0002218) | 8.15 | 2.42E−05 |
| hemopoiesis (GO:0030097) | 4.85 | 2.69E−05 |
| regulation of cytokine production (GO:0001817) | 4.6 | 2.94E−05 |
| locomotion (GO:0040011) | 3.28 | 4.78E−05 |
| leukocyte cell-cell adhesion (GO:0007159) | 6.89 | 6.01E−05 |
| regulation of cytokine secretion (GO:0050707) | 9.53 | 6.13E−05 |
| positive regulation of response to external stimulus (GO:0032103) | 6.29 | 6.57E−05 |
| lymphocyte activation (GO:0046649) | 5.81 | 7.01E−05 |

Table 7 below shows biological processes enrichment for the top 200 genes downregulated in pMGLs compared to NPCs. Broadly highlighting the neuroectodermal nature of NPCs, highlighting terms focusing on CNS development.

TABLE 7

Processes DOWN in pMGLs compared to NPCs

| GO biological process complete | enrichment | p-value |
|---|---|---|
| forebrain development (GO:0030900) | 6.89 | 5.05E−03 |
| central nervous system development (GO:0007417) | 5.4 | 1.70E−06 |
| brain development (GO:0007420) | 5.37 | 3.56E−04 |
| behavior (GO:0007610) | 5.22 | 2.69E−02 |
| head development (GO:0060322) | 5.08 | 7.58E−04 |
| neuron differentiation (GO:0030182) | 4.14 | 1.10E−02 |
| generation of neurons (GO:0048699) | 3.6 | 1.97E−03 |
| neurogenesis (GO:0022008) | 3.38 | 5.45E−03 |
| nervous system development (GO:0007399) | 3.26 | 2.22E−05 |
| cell differentiation (GO:0030154) | 2.4 | 4.70E−03 |
| cellular developmental process (GO:0048869) | 2.25 | 2.08E−02 |
| system development (GO:0048731) | 2.23 | 2.66E−03 |
| multicellular organism development (GO:0007275) | 1.99 | 3.41E−02 |
| anatomical structure development (GO:0048856) | 1.91 | 4.70E−02 |
| multicellular organismal process (GO:0032501) | 1.78 | 1.93E−02 |
| Unclassified (UNCLASSIFIED) | 0.45 | 0.00E+00 |

Table 8 shows a composite list of 300 genes specific of microglia or important to microglial physiology. This list is used in the hierarchical clustering of FIG. 10B and Supplementary FIG. 14B.

TABLE 8

| | | | | | | |
|---|---|---|---|---|---|---|
| 0610007C21Rik | cd53 | Fam105a | il7rptxdc1 | olfml3 | slc25a4 | trn4rl1 |
| 0610009O20Rik | cd68 | fam110a | itga6 | ophn1 | slc29a3 | trpv2 |
| 0610040J01Rik | cd74 | fcer1g | itga9 | orai1 | slc2a5 | tspan3 |
| 1500011K16Rik | cd79b | fcer2b | itgam | osm | slc37a2 | tspan7 |
| 1810006K21Rik | cd80 | fcgr1 | itgb2 | p2rx7 | slc39a1 | ttr |
| 2310016M24Rik | cd81 | fcgr3 | itgb3 | p2ry12 | slc40a1 | tyrobp |
| 4632428N05Rik | cd83 | fcrl1 | itgb5 | p2ry13 | slc46a1 | ubash3b |
| 6230427J02Rik | cd84 | fcrls | itm2b | p2ry6 | slc7a7 | upk1b |
| 9330133O14Rik | cd86 | fermt3 | itpripl1 | p2ryx4 | slc7a8 | x99384 |
| abca9 | cfh | fscn1 | kcnk13 | pdgfb | slco2b1 | zfp658 |
| abcc3 | clec4a2 | g6pc3 | kcnk6 | plekho1 | slco4a1 | zfp691 |
| abcg2 | cmklr1 | gal3st4 | kctd11 | pmepa1 | smad1 | zfp715 |
| abhd15 | cmtm6 | gas6 | kctd12 | pnp | snn | |
| acp2 | cmtm7 | gm | klhl21 | polr2g | sparc | |
| acvr1 | cnr2 | gm10790 | lag3 | pros1 | srfsf9 | |
| adi1 | commd8 | gm14023 | lair1 | ptafr | srgap2 | |
| adora3 | commd9 | gm5086 | lap3 | ptprc | stab1 | |
| adr2b | comt | gm885 | lcam1 | ptxdc2 | stau1 | |
| AF251705 | cpr84 | gna15 | lcosl | ptxnb2 | stx8 | |
| ang | crl1 | golm1 | ldhb | pvrl4 | syngr1 | |
| arhgap12 | cryba4 | gp9 | leprel1 | pycard | tanc2 | |
| asb2 | crybb1 | gpr155 | lgals9 | rab3il1 | tbcb | |
| asph | csf1r | gpr157 | lgmn | rapgef5 | tfpi | |
| b2m | csf2rb | gpr160 | lhfpt2 | rcan1 | tgfa | |
| b4galt4 | csf2rb2 | gpr165 | liph | rgs10 | tgfb1 | |
| bin1lrrc3 | csf3r | gpr183 | lman1 | rnase4 | tgfbr1 | |
| blnk | ctsd | gpr34 | lpar6 | rps27l | tgm2 | |

TABLE 8-continued

| | | | | | |
|---|---|---|---|---|---|
| BV004004 | ctsf | gpr65 | lrrc33 | rtn4rl1 | thrsp |
| c1qa | ctso | gpr77 | ltc4s | sdmap2 | tlr1 |
| c1qb | cxcl16 | H2-D1 | lxdc2 | selplg | tlr12 |
| c1qc | cxxc5 | H2-Dma | ly6e | sepp1 | tlr13 |
| C330006A16Rik | cyb5 | H2-dmb1 | ly86 | serinc3 | tlr2 |
| c3ar1 | cysltr1 | H2-K1 | ly96 | serpinf1 | tlr4 |
| casp8 | D15Ertd621e | H2-M3 | mas4a6b | sft2d1 | tlr5 |
| ccl12 | dctpp1 | H2-Oa | mef2c | sft2d2 | tlr6 |
| ccl2 | dnajb4 | H2-Ob | mertk | sgce | tlr9 |
| ccl3 | dpm3 | H2-t3 | mpi | sgk1 | tmem106a |
| ccl4 | dusp7 | havcr2 | mrc1 | siglece | tmem119 |
| ccl6 | dynlrb1 | hexb | ms4a6c | siglech | tmem14c |
| ccl9 | ebi3 | Hfe | ms4a6d | sirpa | tmem173 |
| ccr5 | ecscr | hmga2-ps1 | mylip | slamf8 | tmem185b |
| cd14 | eif2s1 | ifnar2 | nckap1l | slamf9 | tmem204 |
| cd164 | elmo1 | ifngr1 | ndufa3 | slc02b1 | tmem37 |
| cd180 | emr1 | ifngr2 | ndufa7 | slc10a3 | tmem55b |
| cd276 | eng | IL10ra | ndufc2 | slc11a1 | Tnfaip8l2 |
| cd300a | entpd1 | il10rb | ndufs3 | slc15a3 | tnfrsf11a |
| cd34 | epb4.1/2 | il1a | notch2 | slc16a10 | tnfrsf17 |
| cd37 | etv5 | il21r | npp5d | slc16a3 | tnfrsf1b |
| cd48 | fl1r | il4ra | numb | slc16a6 | tpcn1 |
| cd52 | fam102b | il6ra | olfml2b | slc17a9 | trem2 |

REFERENCES

1. Napoli, I, et al. *Glia* 2009; 57(15): 1660; and Beutner, C. et al. *Nat. Protoc.* 2010; 5(9): 1481.
2. Bennett, M. L., et al. *Pro Natl Acad Sci USA* (2016), New tools for studying microglia in the mouse and human CNS. E1738-1746.

All cited references, US and foreign patents or patent publications, are incorporated herein by reference. It should be understood that where the instant invention discloses a medium, the invention provides methods of making the medium, kits containing the medium, methods comprising culturing cells in the medium, cells cultured in the medium, and methods of using the cells.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A method of deriving a microglial cell or microglia-like cell from at least one human pluripotent stem cell, comprising:
   a) contacting at least one human pluripotent stem cell with a passaging reagent;
   b) incubating the human pluripotent stem cell of step a) in the presence of a culture medium that comprises one or more amino acids; one or more vitamins; one or more inorganic salts; glucose or galactose; buffering agent; serum albumin; transferrin; sodium chloride; a pyruvate salt; glutamine; biotin; ascorbic acid; lactic acid, or a salt thereof; corticosterone; linoleic acid; linolenic acid; progesterone; DL-α-Tocopherol and/or DL-α-Tocopherol acetate; lipoic acid; L-carnitine HCl; ethanolamine HCl; D-Galactose (anhydrous); putrescine dihydrochloride; sodium selenite; catalase; glutathione (reduced); insulin; human-holo-transferrin; superoxide dismutase; T3; Interleukin-34 (IL-34); and macrophage colony-stimulating factor (M-CSF), wherein the osmolarity of the medium is at least 275 mOsm, wherein the at least one human pluripotent stem cell is a plurality of human pluripotent stem cells and wherein incubating is for a time sufficient to generate cystic embryoid bodies comprising immature microglial or microglia-like cells; and
   c) harvesting immature microglial or microglial-like cells that delaminate from said cystic embryoid bodies; thereby deriving a microglial cell or microglia-like cell from the pluripotent stem cell.

2. The method of claim 1, wherein the human pluripotent stem cell is a human embryonic stem cell or a human induced-pluripotent stem cell.

3. The method of claim 1, further comprising d) plating said harvested immature microglial or microglial-like cells that delaminate from said cystic embryoid bodies formed through said incubating of the plurality of human pluripotent stem cells to thereby allow attachment of said cells to a plate.

4. The method of claim 3, wherein said plating comprises using plastic plates.

5. The method of claim 4, wherein said plastic comprises polystyrene.

6. The method of claim 1, wherein the method comprises triturating said cystic embryoid bodies to promote shedding of at least one immature microglia-like cell from said cystic embryoid bodies.

7. The method of claim 6, further comprising maintaining said harvested immature microglia-like cell for a time sufficient for maturation of said at least one immature microglia-like cell into said microglial cell or microglia-like cell.

8. The method of claim 7, wherein said medium further comprises a conditioned medium obtained from a differentiating neural or neuro-glial culture.

9. The method of claim 1, wherein the serum albumin is bovine serum albumin or human serum albumin.

10. The method of claim 1, wherein the serum albumin is bovine serum albumin fraction V or lipidated bovine serum albumin.

11. The method of claim 1, wherein the osmolarity of the medium is at least 290 mOsm.

12. The method of claim 1, wherein the osmolarity of the medium is between 290 mOsm and 300 mOsm.

* * * * *